US007476517B2

(12) United States Patent
Hunt

(10) Patent No.: US 7,476,517 B2
(45) Date of Patent: Jan. 13, 2009

(54) VIRUS LIKE PARTICLES, THEIR PREPARATION AND THEIR USE PREFERABLY IN PHARMACEUTICAL SCREENING AND FUNCTIONAL GENOMICS

(75) Inventor: Nicholas Hunt, Neu-Wulmstorf (DE)

(73) Assignee: Evotec AG, Hamburg (DE)

( * ) Notice: Subject to any disclaimer, the term of this patent is extended or adjusted under 35 U.S.C. 154(b) by 202 days.

(21) Appl. No.: 11/025,650

(22) Filed: Dec. 30, 2004

(65) Prior Publication Data
US 2006/0046291 A1   Mar. 2, 2006

Related U.S. Application Data

(63) Continuation of application No. 09/750,185, filed on Dec. 29, 2000, now abandoned, which is a continuation-in-part of application No. 09/673,257, filed as application No. PCT/EP00/06144 on Jun. 30, 2000, now abandoned.

(60) Provisional application No. 60/141,268, filed on Jun. 30, 1999.

(30) Foreign Application Priority Data

| Jun. 30, 1999 | (EP) | 99112451 |
| Mar. 21, 2000 | (EP) | 00106109 |
| May 15, 2000 | (EP) | 00110363 |

(51) Int. Cl.
  *C12N 15/00* (2006.01)
(52) U.S. Cl. ............... 435/69.1; 435/320.1; 435/91.4; 424/207.1
(58) Field of Classification Search ............ 435/320.1
See application file for complete search history.

(56) References Cited

U.S. PATENT DOCUMENTS 5,885,808 A  3/1999  Spooner et al.

FOREIGN PATENT DOCUMENTS

| DE | 195 43 553 A1 | 5/1997 |
| EP | 0 959 135 A1 | 11/1999 |
| EP | 0 960 942 A2 | 12/1999 |
| EP | 0 972 841 A1 | 1/2000 |
| WO | WO 88/03563 | 5/1988 |
| WO | WO 93/01833 | 2/1993 |
| WO | WO 94/02173 | 2/1994 |
| WO | WO 94/20621 | 9/1994 |
| WO | WO 96/30523 | 10/1996 |
| WO | WO 96/35798 | 11/1996 |
| WO | WO 98/02548 | 1/1998 |
| WO | WO 98/28004 | 7/1998 |
| WO | WO 98/49195 | 11/1998 |
| WO | WO 99/29723 | 6/1999 |
| WO | WO 99/50424 | 10/1999 |
| WO | WO 00/09157 | 2/2000 |
| WO | WO 00/32227 | 6/2000 |
| WO | WO 01/02551 | 1/2001 |

OTHER PUBLICATIONS

Chackerian et al. P.N.A.S. USA 1999, vol. 96, pp. 2373-2378.*
Tripet et al. Protein Eng. 1996, vol. 9, pp. 1029-1042.*
Schuber et al. J. Virol. 1992, vol. 66, pp. 1579-1589.*
Tice et al. Proc. Natl. Acad. Sci. USA, 1999, vol. 96, pp. 115-1420.*
Li et al. B. B. R. C. 1995, vol. 216, No. 1, pp. 110-118.*
De Haan et al., "Assembly of the Coronavirus Envelope: Homotypic Interactions between the M Proteins", *Journal of Virology*, 74, 4967-78 (2000).
Loisel et al., *Nature Biotechnology*, 15, 1300-1304 (1997).

* cited by examiner

*Primary Examiner*—Bruce Campell
*Assistant Examiner*—Bao Qun Li
(74) *Attorney, Agent, or Firm*—Jacobson Holman PLLC

(57) ABSTRACT

The invention relates to virus like particles, their preparation and their use in pharmaceutical screening and functional genomics. The invention further provides a variety of assay formats to be used with said virus like particles.

13 Claims, 25 Drawing Sheets

Fig. 9

Figure 1:
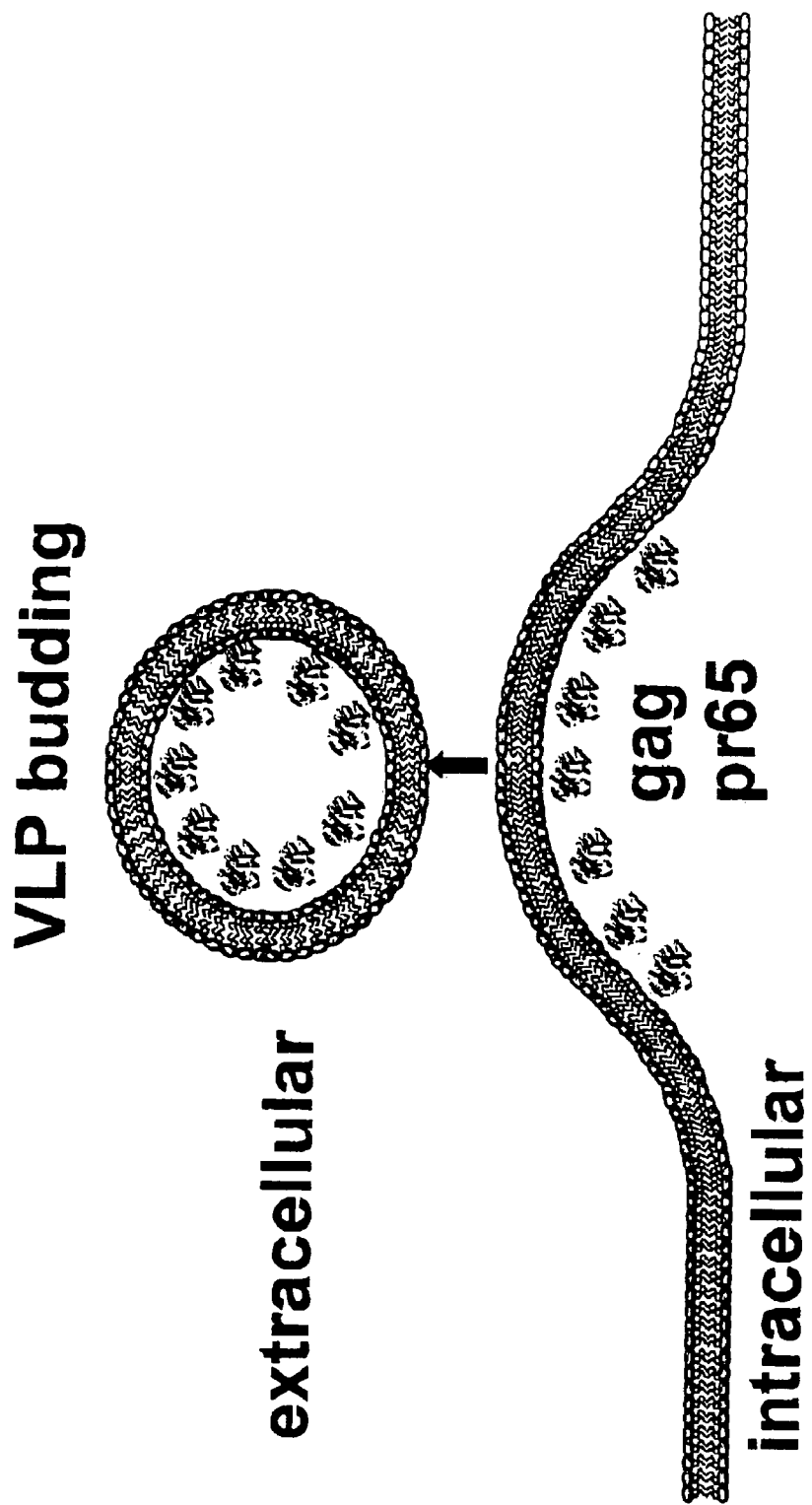

Binding of TAMRA-labeled Endothelin-1 to Human ET Receptor on Membrane Vesicles and VLPs

VLP based reporter assay

− forskolin

+ forskolin

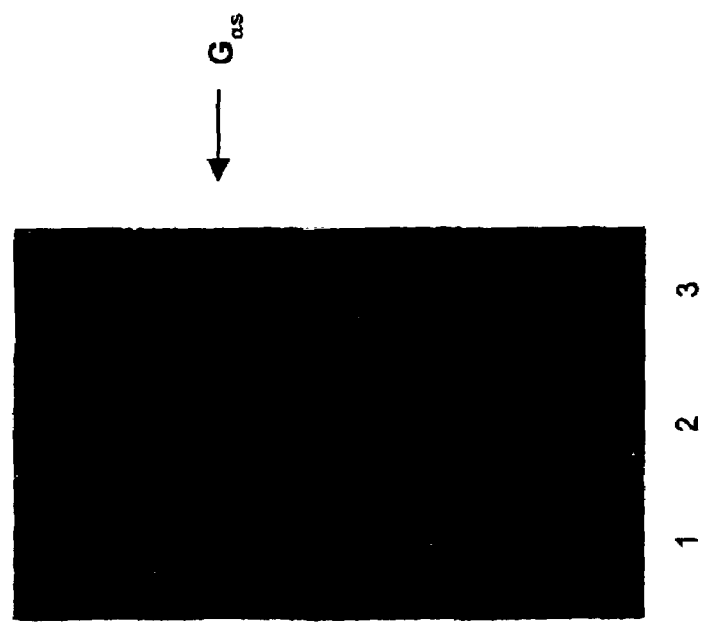
Fig. 25 G-protein ($G_{\alpha s}$) expression in VLPs carrying the Human Endothelin A Receptor

VIRUS LIKE PARTICLES, THEIR PREPARATION AND THEIR USE PREFERABLY IN PHARMACEUTICAL SCREENING AND FUNCTIONAL GENOMICS This is a continuation of Ser. No. 09/750,185, filed 29 Dec. 2000, abandoned, which is a continuation-in-part of Ser. No. 09/673,257, filed 2 Oct. 2001, abandoned, which is a 371 of PCT/EP00/06144, filed 30 Jun. 2000, which claims the benefit of U.S. Provisional Application No. 60/141,268, filed Jun. 30, 1999, the disclosures of which are incorporated herein by reference.

The invention relates to virus like particles, their preparation and their use preferably in pharmaceutical screening and functional genomics. The invention further provides a variety of assay formats to be used with said virus like particles.

The analysis of functional integral membrane proteins can be performed in a number of state of the art systems and environments. Receptors can be analysed for ligand interactions directly on the cells in which they are either endogenously expressed or in a recombinant cell system in which they are usually over-expressed. However, although these molecules are usually functional in such an environment their analysis is hampered, as a result of the high background levels, by the presence of a large number/concentration of contaminating functionally similar or related proteins. Thus, the sample is very heterogeneous even if the particular protein or endogenous receptor of interest is expressed at high copy numbers already, or over-expressed under a strong recombinant promoter.

Furthermore however, binding domains, whether being a receptor, an adhesion molecule or catalytic molecules can be analysed after enrichment or purification of the respective molecule to homogeneity from a source in which the original activity was detected. However, such purification steps often result in the removal of the respective proteins from their normal lipid/lipid-protein environment which can result in the loss of either partial or complete function due to denaturing effects after removal of the specific molecule of interest from its native environment. This usually results in the necessity of requiring extensive quantities of starting or recombinant material in order to purify (or concentrate at least) respective amounts of the target of interest.

Various methodological formats applied in ultra high throughput screening (uHTS), including assays based on homogeneous time-resolved fluorescence (HTRF) or confocal detection techniques, e.g. Fluorescence Correlation Spectroscopy (FCS), utilise specific membrane fractions such as vesicles in which the integral or membrane associated protein of interest is present in high concentrations. However, similar problems with background signals are also experienced with such preparations and usually extensive quantities of cells are required to prepare sometimes minimal amounts of sample. Again such preparations are usually heterogeneous with respect to their quality and integrity thus resulting in appreciable inter-assay variations.

As mentioned above standard assay systems employing either whole cells or enriched membrane preparations thereof (vesicles) suffer a number of disadvantages in that even in recombinant engineered cell systems in which the molecule of interest is over-expressed there is still a considerably high degree of background (see above). In some applications, this problem of high background can be partly reduced by using a methodology for the ligand induced specific labelling of seven transmembrane receptors (7-TMRs, patent DE 197 09 168 C1 and the international patent application PCT/EP 98/01229).

Thus one aim is to, in which all of the above mentioned problems are solved, express the respective protein (e.g. a biologically active 7-TMR or other integral membrane protein) in a stable and preferably its natural environment (e.g. the plasma membrane) and devoid of contaminating proteins, in a convenient and economical fashion resulting in the production of sufficient quantities of high quality material amenable for high throughput screening.

A methodology is needed which enables one to, for example, obtain large amounts of a specific recombinant integral membrane protein in a stable environment in which the specific function Is not diminished and in which the proportion of otherwise contaminating interfering membrane proteins is preferably <10%. (These contaminating proteins might either be non-specifically encapsulated by or within the membrane during the preparation or might represent accessory proteins whose affinity and proximity is such that they are not segregatable during their respective biological or experimental application). Such a system should preferably allow one to apply optical detection technologies, such as single molecule or single particle based detection systems (e.g. described in EP 0 679 251 B1), to monitor the functional interaction of a known or unknown ligand with a selected target protein for example in a receptor-ligand binding assay. It is of particular interest to find novel agonists and antagonists for the vast number of orphan-type receptors, as described in the patent DE 197 09 168 C1 and the international patent application PCT/EP 98/01229 in combination with a preferably homogeneous optical assay which is dependent upon definitive and precise signals as compared to Western Blots which tolerate a variety of background signals as long as they are spatially separated from a specific signal of interest. However, the latter methodology is not amenable to high throughput screening and thus a technique has to be employed which is adaptable to screening. For this purpose a homogeneous assay, i.e. a mix-and-measure-assay which does not rely on separation steps to e.g. distinguish receptor-bound and free ligands, would be of great advantage. Such an assay regimen would be of utmost interest and importance to the pharmaceutical industry which is constantly searching for a functional assay approach; applicable to the vast number of receptors being discovered by numerous functional genomics programs. Secreted proteins and outer membrane proteins are economically until now the most important class of therapeutic targets. Approx. 64% of all drugs known are currently directed against the family of 7-transmembrane receptors. In addition, reagents for the conductance of the above mentioned assays are needed.

These problems are solved by the invention which provides different virus like particles and assay formats in which these virus like particles can be applied.

Virus like Particles, their Preparation and Detection.

In a first aspect the invention provides a method to selectively incorporate or encapsulate proteinaceous target molecules into virus like particles (VLPs). Target molecules are co-expressed in recombinant cells together with signal molecules. Each target molecule and each signal molecule comprises a first and a second amino acid sequence. The second amino acid sequence of the signal molecule confers on the signal molecule the ability to assemble into virus like particles which are preferably released into an extracellular environment in which they can easily be detected. The first amino acid sequences of said signal molecules are chosen in such a way that they are able to functionally operate in a non-covalent manner with said first amino acid sequences of said target molecules. By virtue of this interaction, a second amino acid sequence of interest, e.g. a receptor or binding domain, is incorporated into or encapsulated by the virus like particle. The first amino acid sequences of said signal molecules preferably-functionally operate with said first amino acid sequences of said target molecules by non-covalent forces such as van der Waals forces, electrostatic forces, stacking interactions, hydrogen bonding or steric fit. Preferably these forces have a binding constant of $K_{ass} \geqq 10^{-6}$ M.

The strategy described by this invention preferably uses a generic tagging strategy so that all proteins can be modified using the same components resulting in a standard operating procedure for all of the proteins to be validated.

It is possible to generate a homogeneous population of VLPs in which a functional target protein of choice is expressed either within the lipid bilayer of an enveloped VLP or within the capsid of a naked or enveloped VLP. It is also possible to encapsulate target proteins within the VLP. These reactions are mediated by the specific interaction with a signalling protein. The incorporation/encapsulation of the respective target proteins is preferably achieved by utilization of a signal molecule with a specific concatameric protein sequence which interacts specifically and with high affinity with a complementary concatameric tag located at either the carboxyl or amino terminal end of the respective target protein. When both of these modified proteins (signal and target) are expressed within the same host cell, then the expressed protein products associate with one another via the specific tags. This interaction results in a preferred embodiment in the translocation of the respective complexes to the cell membrane in high concentrations where they are extruded from the cells via a budding process similar to the release of mature virus particles. Most enveloped virus like particles acquire their membrane or "envelope", a lipid bilayer and associated target proteins, by budding through an appropriate cellular membrane—the plasma membrane in many cases, the ER, Golgi, or nuclear membranes in others. Details of budding processes are known in the prior art (for a general review see e.g. Fields et al. "Fundamental Virology", Chapter 3, 3rd edition, Lippincott-Raven, 1996). Virus like particles might however also be released from the cell by exocytosis or lysis.

In many cases, said second amino acid sequence of said target molecule is heterologous to the virus like particle. It might be of interest to choose as a second sequence a receptor, an ion channel, an enzyme, an adhesion molecule, a component of a membrane pore, an antigen, or fragments or derivatives of the foregoing. It is particularly preferred to choose a transmembrane receptor, in particular a G-protein coupled receptor, which is incorporated into an envelope of a virus like particle by a budding process on the basis of the present invention. However, also cytosolic or nuclear receptors can be incorporated into or encapsulated by a protein capsid of a naked or enveloped VLP. For the conductance of the below described different assay formats, it might also be suitable to choose as a second amino acid sequence of said target molecules a luminescent peptide or protein.

With respect to the second amino acid sequence of the signal molecule, it is preferred that it comprises at least a fragment of a virus capsid or envelope protein, or a precursor of a virus capsid or envelope protein, or a mutant of a virus capsid or envelope protein. It might however also comprise at least a fragment of a capsid or envelope protein of a virus like particle, or a precursor of said capsid or envelope protein, or a mutant of said capsid or envelope protein. Capsid or envelope proteins might be chosen from a variety of virus families including, but not limited to, retroviruses, picornaviruses, reoviruses, polyomaviruses, papillomaviruses, parvoviruses, nodaviruses, coronaviruses, herpesviruses, hepadnaviruses, baculoviruses and bacteriophages. It is e.g. also possible to utilize a second amino acid sequence of said signal molecule which is encoded by at least a fragment of a retrotransposon, in particular a Ty element in yeast, a copia element in insects, a copia-like element in insects, VL 30 in mice, or an IAP gene in mice. A list of particularly suitable sequences is given in the following table,

| Virus family | Self assembling capsid or envelope component | Example | Literature (the contents of which are herein incorporated by reference) |
|---|---|---|---|
| Retroviridae | Components encoded by the gag gene, polyprotein precursor of Gag, or truncated Gag. | Moloney Murine Leukaemia Virus (MoMULV) gag Pr65 | Delchambre et al., EMBO J 8, 2653-2660, 1989; Luo et al., Virology 179, 874-880, 1990; Royer et al., Virology 184, 417-422, 1991; Morikawa et al., Virology 183, 288-297, 1991; Zhou et al., J. Virol. 68, 2556-2569, 1994; Gheysen et al., Cell 59, 103-112, 1989; Hughes et al., Virology 193, 242-255, 1993; Yamshchikov et al., Virology 214, 50-58, 1995. WO 96/30523, Applicant: H. Wolf. WO 94/20621, Applicant: British Biotechnology LtD. WO 96/35798, Applicant: Introgene B.V. EP 0972841 A1, Applicant: Introgene B.V. EP. . EP 0960942 A2, Applicant: Introgene B.V. EP. . EP 0959135 A1, Applicant: Introgene B.V. EP. |
| Picornaviridae | Capsid components derived from polyprotein precursor | Poliovirus VP0, VP1 and VP3 | Fundamantal Virology (third edition) Edited by Fields et al. 1996. Chapter 16. Picornaviridae. 477-522. |
| Reoviridae | Structural capsid components encoded by RNA segments | Rotavirus VP2, VP1/2, VP1/2/3, VP2/3, VP2/6, VP2/6/7, VP2/4/6/7, VP1/2/3/6 | Fundamantal Virology (third edition) Edited by Fields et al. 1996. Chapter 24. Reoviruses. 691-730. |
| Polyomavirinae | Structural capsid proteins | Polyoma Virus VP1, VP2 and VP3 | Fundamantal Virology (third edition) Edited by Fields et al. 1996. Chapter 28. Polyomaviridae. 917-945. DE 19543553 A1, Applicant: Deutsches Primaten Zentrum. |
| Papillomavirinae | Structural capsid proteins | Human papillomavirus L1 and | Fundamantal Virology (third edition) Edited by Fields et al. 1996. Chapter 29. Papilomavirinae. 947-978. WO 00/09157, Applicant: Merck & CO. Inc. WO 99/50424, Appli- |

-continued

| Virus family | Self assembling capsid or envelope component | Example | Literature (the contents of which are herein incorporated by reference) |
| --- | --- | --- | --- |
| | | L1/L2 | cant: M. Stanley. WO 98/02548, Applicant: The government of the united states of America. |
| Parvoviridae | Structural capsid proteins | Adeno associated virus VP1, VP2 and VP3 | Fundamantal Virology (third edition) Edited by Fields et al. 1996. Chapter 31. Parvoviridae. 1017-1041. |
| Herpesviridae | Structural capsid proteins | Herpes simplex virus, VP5, VP19C, VP23, VP26 | Fundamantal Virology (third edition). Edited by Fields et al. 1996. Chapter 32. Herpes Simplex viruses and their replication. 1043-1107, |
| Hepadnaviridae | Structural capsid protein | Hepatitis virus S protein | Fundamantal Virology (third edition) Edited by Fields et al. 1996. Chapter 35. Hepadnaviridae andtion their replic. 1199-1233. WO 98/28004, Applicant: The crown in the right of the Queensland department of health. |
| Nodaviridae | Stuctural capsid protein | Flock house virus, Protein Alpha | Fundamantal Virology (third edition) Edited by Fields et al. 1996. Chapter 13. Insect viruses. 401-424. WO 99/29723, Applicant: Pentamer Pharmaceuticals. |
| Coronaviridae | Structural proteins | Mouse hepatitis virus M and E proteins | Fundamantal Virology (third edition) Edited by Fields et al. 1996. Chapter 18, Coronaviridae. 541-559. WO 98/49195, Applicant: Universitiet Utrecht. |
| Retrotransposons | Retrotransposon coding region | Protein encoded by Yeast retrotransposon Ty, Insect copia and copia-like elements, Murine VL30 and IAP genes. | WO 88/03563 |

However, it is particularly preferred to use as said second amino acid sequence of said signal molecule a structural protein encoded by the gag-gene of retroviruses. The invention will be described mostly with respect to utilization of Gag-protein. This illustration is not intended to limit the scope in any way.

Artificial constructs derived from retroviruses can be used to e.g. selectively display a protein of interest such as a receptor or receptor subunit on the outer surface of a virus like particle. In the following the current status of knowledge of the organisation of retroviruses Is summarized.

Retroviruses have a protein capsid which contains among other constituents the viral genetic material and the reverse transcriptase complex. Outside the capsid is a lipid bilayer derived from the host cell plasma membrane in which viral envelope glycoproteins are embedded. During the infection cycle these envelope glycoproteins initiate an infection by recognising and binding specific receptors on the surface of a host cell and inducing fusion of the viral and cell membranes. After intracellular genome replication and its integration into the cell chromosome, viral RNAs encoding structural proteins are produced and nascent virions are assembled. Newly synthesised viral capsids specifically incorporate viral glycoproteins from the plasma membrane during viral budding while, for the most part, excluding the cellular proteins. This retroviral assembly process is an important aspect of the basic molecular biology of retroviruses. The complexity of this process of viral capsid formation and release from the host cell by the budding process is described in more detail below.

The genome of all retroviruses codes for principally three major gene products, notably the gag gene coding for structural proteins, the pol gene coding for reverse transcriptase and associated proteolytic polypeptides, nuclease and integrase associated functions, and env whose encoded glycoprotein membrane proteins are detected on the surface of infected cells and also on the surface of mature released virus particles. The gag gene of all retroviruses analysed so far have an overall structural similarity and are conserved particularly at the amino acid level within each group. The gag and the pol genes can be grouped together for both products and are synthesised as a simple high molecular weight precursor polyprotein e.g. Pr65$^{Gag}$ (for the Murine leukaemia virus, MuLV) or Pr200$^{Gap\text{-}Pol}$ which is subsequently cleaved to give rise to the mature proteins. The Gag proteins give rise to the core proteins excluding the reverse transcriptase. For MuLV the Gag precursor polyprotein is Pr65$^{Gag}$ and is cleaved into four proteins whose order on the precursor is NH$_2$-p15-pp12-p30-p10-COOH. It appears that these cleavages are mediated by a viral protease. The MuLV Gag protein exists in a glycosylated and a nonglycosylated form The glycosylated forms are cleaved from gPr80$^{Gag}$ which is synthesised from a different inframe initiation codon located upstream from the AUG codon for the non-glycosylated Pr65$^{Gag}$. Deletion mutants of MuLV that do not synthesise the glycosylated Gag are still infectious, thus raising the question over the importance of the glycosylation events. The post translational cleavage of the HIV-1 Gag precursor of 55 000 Da (pr55$^{Gag}$) by the virus coded protease yields the N-myristoylated and internally phosphorylated p17 matrix protein (p17MA), the phosphorylated p24 capsid protein (p24CA), and the nucleocapsid protein p15 (p15NC), which is further cleaved into p9 and p6.

Translation of the MuLV pol gene is achieved by a ribosomal-1 frame shift close to the end of the gag gene. The translation frame shift allows the synthesis of a 160 kD polyprotein consisting of a truncated Gag fusion protein fused to the product of the pol reading frame. However, the level of the GagPol fusion protein production is only 5-10% of the level of production of Gag protein (Jacks et al., Cell 55, 447-458, 1988; Wilson et al., Cell 55, 1159-1169, 1988).

The pol gene encodes the viral enzyme protease, reverse transcriptase, and integrase which are cleaved from the precursor by the viral protease (Lightfoote et al., J. Virol. 60, 771-775, 1986; Oroszian and Luftig Curr Top Microbiol Immunol 157, 153-185,1990; Peng et al., I. Virol. 65, 2751-2756, 1991).

The env gene encodes the surface glycoproteins of the virion that are necessary for initiating an infection cycle.

Because of their location and role the env products determine both the host range and the neutralisation antigens of the virion. Although not closely related to one another the env genes of different groups show a great deal of structural similarity. The amino terminal sequence of the env product encodes a signal peptide which is cleaved off as a consequence of transmembrane processing of the Env precursor. The env gene product of MuLV Pr90$^{Env}$ is glycosylated and cleaved to gp70 and p15E, which remain bound to each other via a disulphide linkage. P15E is a transmembrane protein with its carboxyl terminus located internal to the lipid membrane and its amino terminus located external to the membrane. In electron micrographs p15E represents the spikes on the viral envelope while the gp70 is the knob that surmounts the spike. As already described the larger amino terminal protein contains determinants to specify host range. The smaller carboxyl terminal protein always contains, near its carboxyl terminus a hydrophobic domain of 20 amino acids or more, constituting a transmembrane anchor region, followed by a basic amino acid and a cytoplasmic domain of varying size, which is presumably involved in the recognition of capsid proteins.

Assembly of retroviruses takes place by a budding process at the cellular plasma membrane. Studies with several retroviruses have demonstrated that the Gag poly-protein expressed in the absence of other viral components is self sufficient for particle formation and budding at the cell surface (Wills and Craven AIDS 5, 639-654, 1991; Zhou et al., J. Virol. 68, 2556-2569, 1994; Morikawa et al., Virology 183, 288-297, 1991; Royer et al., Virology 184, 417-422, 1991; Gheysen et al., Cell 59, 103-112, 1989; Hughes et al., Virology 193, 242-255, 1993; Yamshchikov et al., Virology 214, 50-58, 1995). Form ation of retrovirus like particles upon expression of the Gag precursor in insect cells using a Baculovirus vector has been demonstrated by several groups (Delchambre et al., EMBO J. 8, 2653-2660, 1989; Luo et al., Virology 179, 874-880, 1990; Royer et al., Virology 184, 417-422, 1991; Morikawa et al., Virology 183, 288-297, 1991; Zhou et al., J. Virol. 68, 2556-2569, 1994; Gheysen et al., Cell 59, 103-112, 1989; Hughes et al., Virology 193, 242-255, 1993; Yamshchikov et al., Virology 214, 50-58, 1995). These Gag particles resemble immature lentivirus particles and are efficiently assembled and released by budding from the insect cell plasma membrane. In contrast to the expression in mammalian cells inclusion of the protease region in Gag expressing vectors in the Baculovirus system leads to over expression of the protease and early processing of the Gag precursor into mature structural proteins within insect cells which prevents particle formation and release (Morikawa et al., Virology 183, 288-297, 1991; Hughes et al., Virology 193, 242-255, 1993). Immature particles undergo a process of maturation by the viral protease involving cleavage of the Gag precursor into the structural proteins, matrix, core and nucleocapsid proteins (Wills and Craven AIDS 5, 639-654, 1991).

It has been reported that the amino terminal region of the Gag precursor is a targeting signal for transport to the cell surface and membrane binding which is required for virus assembly (Yu et al., J. Virol. 66, 4966-4971, 1992; an, X et al., J. Virol. 67, 6387-6394, 1993; Zhou et al., J. Virol. 68, 2556-2569, 1994; Lee and Linial J. Virol. 68, 6644-6654, 1994; Dorfman et al., J. Virol. 68, 1689-1696, 1994; Facke et al., J. Virol. 67, 4972-4980, 1993). The mechanism of specific incorporation of envelope protein into the plasma membrane derived envelope of the virus particles is not understood, but interaction of Env with the matrix protein seems to be important (Yu et al., 3. Virol. 66, 4966-4971, 1992; Dorfman et al., J. Virol. 68, 1689-1696, 1994; Gallaher et al., AIDS Res Hum Retroviruses 11, 191-202, 1995; Bugelski, P. J. et al., AIDS Res Hum Retroviruses 11, 55-64, 1995). The human immunodeficiency virus type 1 HIV-1 belongs to the Lentivirus group of retroviruses. Like other retroviruses HIV-1 assembles its mature core particle from two polyprotein precursors encoded by the gag and pol genes. The env gene encodes the envelope glycoprotein of the mature virus particle (Takahashi et al., J Exp Med 170, 2023-2035,1989). In HIV the structures and functions of the gag and pol gene products have been studied extensively to understand their roles in the viral morphogenetic process. This has led to a description of the virus particle as consisting of the nucleocapsid protein complex within a hydrophobic core of p24 which is surrounded by a matrix layer of p17. The core together with the matrix layer is enveloped by the host cell membrane containing the viral Env glycoprotein. The nucleoprotein complex consists of the viral RNA genome together with the p9 protein and the viral enzymes required for replication and integration of the viral genome (Gelderblom, AIDS 5, 617-637, 1991; Wills and Craven AIDS 5, 639-654, 1991). A second protein, p6, which is encoded by the 3' region of the gag gene has been suggested to be located between the core and the envelope regions although neither the role nor the precise location of the protein has been defined.

Assembly of recombinant HIV like particles that contain Gag structural proteins as well as Env glycoproteins gp120 and gp41 has been reported using a vaccinia virus expression system (Haffar et al., J. Virol. 66, 4279-4287, 1992). It has been reported that these particles induce HIV specific humoral and cellular immunity in rabbits (Haffar et al., J. Virol. 66, 4279-4287, 1992) and can inhibit virus production in latently infected peripheral blood mononuclear cells from HIV-1 sero-positive donors (Haffar et al., J. Virol. 66, 4279-4287, 1992).

The expression patterns of envelope glycoproteins of retroviruses in the Baculovirus system also have several unusual features in comparison to expression in mammalian cells. These proteins are cleaved very inefficiently and are mainly cell associated (Rusche et al., Proc. Natl. Acad. Sci. USA 84, 6924-6928, 1987; Wells and Compans Virology 176, 575-586, 1990; Hu et al., Nature 328, 721-723, 1987). However HIV-1 Env proteins produced in insect cells are immunologically and biologically active, as demonstrated by their ability to react specifically with immune serum (Hu et al., Nature 328, 721-723, 1987; Wells and Compans Virology 176, 575-586, 1990) and to induce syncytium formation upon co-cultivation with HeLa T4 cells (Wells and Compans Virology 176, 575-586, 1990).

The method to selectively incorporate or encapsulate proteinaceous target molecules into virus like particles in one specific embodiment according to the present invention is based upon observations that when one expresses specific structural gene components of retroviruses (the gag gene, or structural protein components from other virus families) as an unprocessed polyprotein in host cells then this gene alone is able to and is responsible for the formation and release of VLPs into the extracellular milieu via a process of budding from the plasma membrane. This observation has been adapted and developed accordingly into a novel methodology in which peptides or polypeptides are incorporated selectively into or encapsulated within host cell derived defined vesicular particles. The specificity of the incorporation/encapsulation of the respective target protein within the VLPs Is the result of a strong specific noncovalent interaction (including van der Waals forces, electrostatic forces, stacking interactions, hydrogen bonding and steric fit) of a molecular peptide tag covalently attached to the signal protein with a complementary specific peptide tag associated with the target of interest. In some cases it might however be preferred to use a covalent fusion of the signal protein with the target protein/peptide of interest.

The signal fusion protein comprising a tag is co-expressed in a cellular system with the respective target molecule of interest which also carries a specific peptide tag either within the molecule or at either the N- or C-terminus. This tag is the complementary partner to that found on the signal protein (and is usually heterologous to both the signal and the target molecule) and interacts specifically and with high affinity with it. The interacting peptides are preferably specifically designed to form hydrophilic charged alpha helices as monomers and interact with one another to form either a parallel or anti-parallel coiled-coil structure when co-expressed. Preferably, the binding constants of the coiled-coil interaction are in the low nM (1-10 nM) range and are specific for the designated pairs. Expression of the modified signal protein (for example the Gag protein from retroviruses) in the respective host cells results in the accumulation of the Gag protein at the plasma membrane due to signals present within the N-terminal portion of the Gag protein. High concentrations of this protein at the plasma membrane are usually a prerequisite for the budding process in which these VLPs are released into the extracellular milieu. If the target protein (for example an enzyme) carrying the complementary tag is expressed in the same cell and is concentrated in the intracellular compartments then the specific interaction with the tagged Gag protein results in the co-transport of the target to the plasma membrane and subsequent incorporation into the released VLPs. Furthermore if the target protein is a soluble cytoplasmic protein (such as an enzyme or a luminescent peptide or polypeptide heterologous to the cell) then it may be fused covalently by standard molecular biology methodology to the C-terminus of the Gag protein. Expression of this fusion protein results in the synthesis of a protein product which is then transported to and concentrated at the plasma membrane of the host cells and subsequently packaged within VLPs via the process of budding and then released into the extracellular milieu. If the target protein is an integral membrane protein (such as a receptor, an ion channel, adhesion molecule or membrane pore complex) then the specific interaction via the coiled-coil tags results after co-localisation and concentration at the plasma membrane in subsequent release of the chimeric VLP containing primarily the tagged Gag protein and target protein of interest. In all cases the resulting VLPs released into the extracellular mileu form composite structures in which functional target proteins/peptides are either encapsulated within or integrated within the enveloped membranous vesicle. As described above, the peptide or polypeptide target may be fused to the signal structure. In a further embodiment, the peptide or polypeptide is non-covalently bound to the signal structure, preferably by interacting tags of binding constants $K_{ass} > 10^6$ $M^{-1}$. The interaction might preferably be based on a complex formation, such as a peptide/peptide interaction, preferably a coiled coil, a peptide ligand interaction or a chelating interaction.

In a further aspect the invention provides virus like particles comprising proteinaceous target molecules incorporated/encapsulated thereinto. These are obtainable by co-expressing in cells said target molecules comprising a first amino acid sequence and a second amino acid sequence together with signal molecules. These signal molecules comprise a first amino acid sequence and a second amino acid sequence, the latter of which confers on the signal molecules the ability to assemble into virus like particles and preferably to be released into an extracellular environment. First amino acid sequences of said signal molecules functionally operate in non-covalent manner with first amino acid sequences of said target molecules whereby said target molecules are incorporated into or encapsulated by said VLPs. These VLPs are preferably released into an extracellular environment where they can easily be detected and or separated. The invention further provides a reagent kit comprising these VLPs and medicaments comprising said VLPs. It might be preferred that the VLPs further comprise molecules integrated into or attached to the capsid of a naked or enveloped VLP or to the envelope of an enveloped VLP, said molecules having the function to direct said medicament to its area of influence. VLPs according to the present invention can e.g. be used for preparation of a medicament or a precursor thereof for treating or preventing genetic diseases, tumor diseases, autoimmune or infectious diseases. They are however also of particular interest and a valuable tool for performing certain assays, e.g. for idendification and characterisation of interactions between target molecules incorporated into distinct populations of VLPs, e.g. for identification and characterisation of interactions between target molecules and further molecules of interest, in particular molecules bound to the surface of cells or beads, in particular beads with molecules attached thereto by means of combinatorial chemistry, or molecules soluble in aqeuous medium, in particular molecules of intracellular functional location. They will become an indispensable tool in identification of potentially pharmaceutically active substances, in identification of analytes in diagnostic applications, and in functional genomics.

This aspect of the present invention also provides a new form of a drug delivery system to cells, resulting in the production of an intracellularly active protein. The protein is produced in a producer cell line with a fusion to a tag interacting with e.g. Gag which is co-expressed by the same cell, resulting in the packaging and exclusion from the producer cell as a VLP. This fraction can easily be purified with the bioactive native and properly processed protein. If the VLPs are at the same time engineered so that they get properly targeted they will recognise their respective target cells in an organism resulting in the uptake of the respective VLP together with the bioactive protein. If necessary the protein to be applied could be incorporated into the VLP in a precursor form which can only be correctly processed after introduction into the respective host cells where it may obtain its full active state. Such VLPs can be applied locally or systemically.

Such an inventive system is also applicable as a reporter system for both the transcription or functional translation of a known or unknown protein and/or a reporter system for the analysis of molecular interactions within cells. Compared to other state of the art methods there is no need For innercellular accumulation of high concentrations of reactants and there is a reduced background signal as compared to assays in which enzymatic reactions are involved to create a non-linear signal amplifying the primary molecular interaction of interest. It offers a number of advantages over two-hybrid systems used to analyse protein-protein interactions as the methodology stands. A number of these advantages include the system can be applied to a wide variety of protein classes as the proteins do not have to be imported into the nucleus. The assay is homogeneous and does not employ complicated selection regimes thus resulting in lower numbers of false positives. Toxicity of the system is reduced due to the continual extrusion of the products from the host cells. The system lends itself as a universal reporter system which can be analysed continuously without the need to prepare cell extracts from the cells of interest. This means that kinetics can easily be followed and cells can be synchronised if desired.

The technology is also suited to pick up any molecule of interest within a cell besides proteins provided there is an attachment/interacting site to the Gag-protein or any other suitable signal molecule. It can be used to attach coding sequences such as DNA or RNA if the transforming DNA or coding RNA can be attached to a tag which can be recognised by a Gag fusion. Decoding of signalling chains is possible by e.g. shot gun expression of a cDNA-library transformed into a strain expressing a protein of interest, in order to pick up its interacting partner proteins, whereby the protein of interest interacts or is bound to the signal structure.

The linkage between e.g. Gag and the protein of interest is managed by and is mediated by direct fusion or non-covalent interactions like protein/protein, peptide/protein or peptide/peptide interactions formed inside a producing cell. Examples are coiled-coil peptide interactions, PDZ domains etc. or any evolutionary evolved e.g. coil coil interaction.

The incorporation of target proteins into VLPs by non-covalent protein-protein interactions has significant advantages over the incorporation by direct, covalent fusion of the target protein with the signal molecule. The incorporation of transmembrane proteins into VLPs requires a specific protein-protein interaction and cannot be accomplished merely by fusion with the Gag signal molecule. Previous accomplishments in the field of utilizing VLPs for pharmaceutical purposes have concentrated on incorporating foreign antigenic molecules into VLPs which have then been used for immunization purposes. In this methodology the foreign protein/peptide sequence have been fused to the C-terminus of a variety of Gag proteins where it has been demonstrated that such a fusion does not interfere with the functioning of the Gag molecule with respect to the formation, maturation and release of VLPs into the extracellular environment. This construction is restricted to the C-terminus because the integrity of the N-terminus is required for the functioning of the Gag protein as signals involved with the processing and membrane transport and interaction are located in this region. In particular the glycine at position two in the protein are required for post-translational modifications which target the protein to the membrane (a fact that has been demonstrated in the literature) and replacement or structural modification at this region demolishes the functionality. Thus a fusion at the N terminus has a detrimental effect. Thus although one could envisage fusing a integral membrane protein to the N-terminus of Gag and indeed this protein could be expressed and transported to the membrane without possible loss of function, the functioning of Gag as a signal molecule responsible for the maturation and release of VLPs Is diminished, However fusion of the integral membrane protein to the C-terminus would result in a fusion protein where Gag remains functional but where the incorrect topology of the membrane protein is impaired resulting in the lack of correct incorporation into the resulting VLP. Thus the only alternative to Incorporate such molecules Into VLPs whereby the functionality of the two respective proteins (Gag and the integral membrane protein) is assured is by synthesizing the two individual proteins independent of one another and complex them at the cell membrane via a specific protein-protein interaction assured by the engineering of the specific tags into the respective molecules.

VLPs based on non-covalent interaction between signal and target molecules according to the present invention as well as prior art VLPs utilizing fusion between signal and target molecules can be used in the following assay formats. These VLPs can either be naked or enveloped, depending on the mode of release from the cell (exocytosis, lysis or budding through an appropriate cell membrane) The target molecule of interest can be incorporated into the protein capsid or into the envelope. It can also be encapsulated within the lumen of the VLP.

Summarized, examples of incorporation/encapsulation of target molecules, although by no means an exhaustive list, include:
  enclosure of target molecules within the confines of the capsid structure of a naked or enveloped virus like particle,
  integration of target molecules into, or attachment to, or physical association with the capsid structure of a naked or enveloped virus like particle,
  integration of target molecules into, or attachment to, or physical association with the membrane of enveloped virus like particles.

Examples of cells to be used according to the present invention include in particular human cells, other mammalian cells, or other eukaryotic cells such as insect cells.

It is generally preferred that all of the following assay formats will be conducted in a homogeneous manner, i.e. in a mix-and-measure mode without the use of any separation steps e.g. to distinguish bound/unbound ligand in a screening process for interaction with a predefined target molecule. Because of new synthesis technologies such as combinatorial chemistry and automated synthesis, the numbers of new molecules available for screening have exploded in the past few years. Furthermore, a growing number of new targets have begun to emerge from genomics efforts. Therefore, the following assays will often be used in a high throughput mode.

Over the years, several fluorescence methods have been developed to address a wide range of biological assays. It is preferred to use these techniques with the following assay formats. Though by no means an exhaustive list, it is recommended to apply fluorescence correlation spectroscopy, fluorescence cross-correlation spectroscopy, fluorescence intensity distribution analysis, fluorescence lifetime measurements, fluorescence resonance energy transfer, or combinations thereof. Particularly, confocal microscopy and spectroscopy techniques can be applied due to their high sensitivity and low background. However, in some cases it might also be suitable to rely on classical microscopic set-ups or to use light scattering techniques. To detect VLPs or analyze their properties one might e.g. also rely on impedance or dielectrophoresis measurements. All of the assay regimens disclosed in the present patent application, can also make use of non-fluorescent, non-optical read out technologies such as radiometric read outs. It might e.g. be particularly preferred to use scintillation proximity assays or filter techniques.

Examples of assay formats which can be studied according to the invention include:
  Assays for the elucidation of ligand/receptor Interactions
  Assays for the elucidation of receptor/receptor interactions
  Assays for the elucidation of intracellular interactions in situ including protein-protein, polypeptide-polypeptide, protein-DNA, protein-RNA and low molecular weight ligand-protein interaction
  Assays involving known/known, unknown/known, unknown/unknown partner interactions
  Assays for the elucidation of
    Cell/cell interactions (including cell adhesion molecules)
    Transcriptional activation based assays, including hormone, CAMP, serum and growth factor responsive DNA elements e.g. CRE, ERE etc.

Assays of innercellular targets
　　Enzymatic systems/enzymatic detection systems attached inside of the VLP to study mediators of such an enzyme activity provided the mediator is able to pass the membrane
　　Innercellular interactions to pick up new interacting proteins and accordingly use the same system as an assay system to enhance the interaction strength or lower it.

It is also preferred to use VLPs produced according to the present invention in an assay described in PCT/EP00/01787, the contents of which are herein incorporated by reference.

The VLPs and assays disclosed herein can optimally be used in combination with, but not restricted to, optical detection systems based on confocal fluorescence detection which is able to follow and measure single molecules or complexes or particles such as VLPs based on translation diffusion, fluorescence anisotropy/polarisation, molecular fluorescence brightness, fluorescence cross-correlation/coincidence, fluorescence lifetime. Such methods are described in EP 0 679 251, European patent application 97 945 816.3, PCT/EP 98/03509, PCT/EP 98/06165, European patent application 97 951 990.7, German patent 197 02 914 and European patent application 99 112 104.7, the contents of which are herein incorporated by reference.

The VLPs and assays disclosed herein can also be applied with handling and sorting technologies such as described in European patent applications 96 939 933.6, 97 953 804.8, 97 952 938.5, PCT/EP 97/07218, PCT/EP 98/08370, PCT/EP 99/02380, PCT/EP 99/04469 and PCT/EP 99/04470 (the contents of which are herein incorporated by reference).

In the following, different assay formats will be described in which the above disclosed VLP types—including those prepared according to one aspect of the present invention as well as those disclosed in the prior art—and detection methods are amenable.

Cell-based Reporter Assays.

In this assay principle a specific effector molecules (e.g. a hormone, or a growth factor, or a low-molecular weight molecule) interacts with a specific molecule on the surface of a cell (e.g. a plasma membrane receptor, or an ion chanel or a pore complex) or is able to traverse the plasma membrane either actively or passively where it is then able to interact with its specific intracellular binding partner (a cytoplasmic or nuclear receptor, or another interacting partner). This interaction stimulates a cascade of specific signalling events within the cell which results in the transcriptional activation of a number of genes within the cell characterised as being under the control of specific transcription factors which interact with specific DNA sequences found in the promoter region of the respective responsive genes. In an engineered cell—where the responsive DNA promoter sequences have been placed so as to control the transcription of a specific reporter gene heterologous to the host cell—upon stimulation of the specific target gene, the transcription of the reporter gene is up- or down-regulated and can be quantified. The quantification of this reporter gene then gives a direct measurement of the activation status of the molecule under study. In an assay format to analyse the activation of the integral membrane protein found on the surface of the cell, compounds are added to the culture which either stimulate or inhibit the activation of this molecule which results in an elevation or decrease of the levels of the reporter molecule being synthesised within the cell (as compared to control cells), the quantification of which is a direct correlation with the influence of the compounds on the molecule under study. According to the invention VLPs can be applied in this assay regime. It is preferred to use as signal molecules fusions between proteins which are capable of assembling into VLPs and a specific molecule which confers a specific property to the VLPs enabling their detection and quantification. These VLPs are preferably released from the cell into an extracellular medium. Thus modulation of the molecule under study by addition of either agonists, antagonists or compounds to the culture medium of such engineered cells results in a modulation of the quantities of VLPs released which can be quantified in accordance with the detectable moiety present in such VLPs. The advantages conveyed by the use of VLPs as a detection system for the analysis of cell based reporter assays include: the sampling and analysis of the assay read out is non-invasive, that is the cells themselves are not destroyed to generate data points with only samples being removed from the cell culture medium in which the VLPs accumulate over time, thus meaning that kinetic measurements are possible. The physico-chemical stability of the VLPs in the extracellular medium also means that the VLPs do not have to be quantified immediately. When using intrinsic properties (luminescence of the fused detectable moiety) of the released VLPs for the quantification, then the presence of high concentrations of test compounds or metabolites thereof will not interfere with the detection of such particles. The quantification of the released particle can be performed in a homogeneous format utilizing intrinsic properties of the VLPs.

Cell Based Reporter Assays with Respect to Functional Genomics.

The assay described defines principles whereby the introduction of specific DNA molecules (under the transcriptional control of either a strong constitutive or inducible promoter) encoding for gene products of either known or unknown function are introduced into recombinant cells performing a certain function, whereby the assay readout gives a direct indication as to whether these gene products are able to modulate this specific function. A specific example of such an assay format would be to analyse the effect of the introduction of a specific DNA sequence which when translated results in a protein product that is able to modulate the down-stream signalling activity of an activated integral membrane protein. In this assay principle a specific effector molecules (e.g. hormone or growth factor or small molecule) interacts with a specific molecule on the surface of a cell (e.g. a plasma membrane receptor, ion channel or pore complex) or is able to traverse the plasma membrane either actively or passively where it is then able to interact with its specific intracellular binding partner (a cytoplasmic or nuclear receptor or interacting partner). This interaction stimulates a cascade of specific signalling events within the cell which results in the transcriptional activation of a number of genes within the cell characterised as being under the control of specific transcription factors which interact with specific genomic DNA sequences found in the promoter region of the respective responsive genes. In an engineered cell where the responsive DNA promoter sequences have been placed so as to control the transcription of a specific reporter gene heterologous to the host cell being used then upon stimulation of the specific target gene, the transcription of the reporter gene is up- or down-regulated and can be quantified. The quantification of this reporter gene then gives a direct measurement of the activation status of the molecule under study.

In an assay format to detect peptide or polypeptide molecules which are able to modulate the down-stream signalling capability of the integral membrane protein found on the surface of the cell, then DNA molecules (under the transcriptional control of either a strong constitutive or inducible promoter) encoding for either peptides or poly-peptides of either known or unknown function are introduced into the cells. These are expressed together with the transcriptionally regulated reporter molecule fusion (preferably Gag-luminescent protein). Cell clones are then selected for the uptake and stable integration of the newly introduced DNA construct by positive selection procedures. These cell clones are then analysed individually or in pools for the release of detectable and quantifiable VLPs released Into the cell culture medium after the addition of effector molecules which are able to positively stimulate the molecule under study. The release of detectable, quantifiable VLPs from control cells expressing the studied molecule and containing the transcriptionally regulated reporter (preferably Gag-luminescent peptide or polypeptide) but containing no exogenously added DNA are compared with the VLPs released from cell clone/pools containing exogenous DNA. If a difference is detected then this effect can be attributed to the function of the protein encoded by the exogenousely applied DNA construct. This effect can be explained by a number of, although not exhaustive, possibilities:

The peptide or polypeptide is able to interact directly (a direct protein-protein interaction) with one or more molecules involved in the signal transduction cascade utilized in conveying the stimulus acting on the receptor through to the transcriptionally regulated reporter molecule and its subsequent release from the cell incorporated within a VLP, The peptide or polypeptide is able to influence the function of the molecules involved in the signal transduction cascade by modifying chemically (e.g. phosphorylation, myristolation, acetylation etc) one or more molecules.

A number of other explanations are possible which have no effect on the signal transduction pathway but which interfere with the translation of the reporter gene RNA or maturation and release of the VLPs which will be detected in the primary screening but which can be disregarded in a secondary analysis by including the appropriate controls.

A further assay format would use the system described above with the difference being that no effector molecules are added to the extracellular medium to activate the respective molecule. Thus one would assay for exogenous DNA molecules that encode for proteins that are able to stimulate the signal transduction cascade pathway in the absence of agonist.

Cell Based Assay for the Detection of Compounds Influencing Viral Maturation and Release.

Viral pathogens pose a challenge to the pharmaceutical industry to develop drugs which intervene in the life cycle of these obligate pathogens., as such drugs have to demonstrate in most cases high specificity towards the virus without detrimental effects on the host cell. The stages where one can intervene are restricted mostly to the replication cycle and spread of the virus within the organism. Thus the processes of viral maturation and release are processes which one could envisage developing small molecule inhibitors. The prior art assay formats used to analyze these processes are relatively time consuming and usually involve either the pathogens themselves or attenuated variants thereof in quantifying the release of virions. The VLP methodology provides an alternative methodology to analyze these processes in a format that is amenable to uHTS. The expression of a variety of different viral capsid proteins, precursor molecules or variants thereof in the absence of other virally encoded proteins results in a number of cases in the maturation of viral capsid structures and subsequent release of immature protein particles or VLPs from the host cell into the extracellular medium. Processes leading to the extrusion of the VLPs into the external environment include budding from the plasma membrane, budding from cytoplasmic or nuclear membrane compartments and subsequent release from the cell by exocytosis or by lysis of the host cell. In an application utilizing such capsid proteins, preferably the Gag protein of Retroviruses, then expression of the Gag precursor protein in cells results in the formation and release of VLPs into the extracellular milieu. Furthermore expression of a precursor Gag-reporter fusion molecule in cells results in the subsequent release of detectable luminescent VLPs which can be quantified preferably using confocal detection technologies. This assay format can thus be applied to screening for compounds which interfere with the maturation and release of VLPs into the extracellular medium. Compounds are added to the cells constitutively expressing e.g. the Gag-reporter gene product and the release of detectable quantifiable VLPs is compared to control cells not treated with the compound, thus an assessment of the inhibition of virus maturation and release can be made.

Assays for Identifying Modulators of Cell Surface Protein-mediated Activity.

In yet another aspect, the invention discloses a method for identifying compounds that modulate cell surface protein-mediated activity by detecting intracellular transduction of a signal generated upon interaction of the compound with the cell surface protein. This methodology comprises comparing the amount of reporter gene product expressed in a first recombinant cell in the presence of the compound, with the amount of reporter gene product in the absence of the compound, or with the amount of reporter gene product in a second recombinant cell. In principle the first recombinant cell contains a reporter gene construct and expresses the cell surface protein of interest. The second recombinant cell is identical to the first recombinant cell, except that it does not express the cell surface protein or expresses the cell surface protein at a predefined level. The reporter gene construct contains a transcriptional control element that is responsive to the intracellular signal generated by the interaction of an agonist with the cell surface protein as well as a reporter gene that encodes a translational signal molecule and is in operative association with the transcriptional control element. The translational signal molecules are able to assemble into virus like particles which are preferably released into an extracellular environment.

Preferably, the method further comprises selecting compounds that influence the amount of reporter gene product expressed in the first recombinant cell in the presence of the compound compared to the amount of reporter gene product in the absence of the compound, or compared to the amount of reporter gene product in the second recombinant cell. In one embodiment, said compound is an agonist of said cell surface protein or in another embodiment said compound is an antagonist of said cell surface protein. In the latter case, the method comprises comparing, prior to or simultaneously with, the difference in the amount of a reporter gene product, after contacting the recombinant cell with an agonist that activates said cell surface protein, whereby said translational signal molecule is expressed.

The cell surface protein can e.g. be a cell surface receptor, an adhesion molecule, a membrane pore, or an ion channel. Preferably, said detectable translational signal molecule further comprises a luminescent polypeptide, in particular green fluorescent protein or mutants thereof, or further comprises an entity which acts as a tag for subsequent labelling with a detectable reagent, or further comprises an enzyme which creates by an enzymatic reaction a suitable read-out parameter. In a preferred embodiment, the transcriptional control region includes at least one regulatory element selected from the group consisting of serum responsive elements, cyclic adenosine monophosphate responsive elements, and elements responsive to intracellular calcium ion levels.

With respect to this assay format, the invention also provides recombinant cells comprising: (i) DNA that encodes a cell surface protein whose activity is modulable by extracellular signals; and (ii) a reporter gene construct containing a reporter gene in operative linkage with one or more transcriptional control element that is regulated by said cell surface protein. The reporter gene encodes a translational signal molecule. These signal molecules are able to assemble into virus like particles which are preferably released into an extracellular medium. Suitable transcriptional control elements, detectable moieties within said signal molecules and types of cell surface proteins are disclosed in the paragraphs above of this chapter. The invention also provides reagent kits comprising these recombinant cells.

Modulators of Receptor- or Ion Channel-mediated Activity.

In still another aspect, the invention provides an approach with particular regard to functional genomics.

A method for identifying substances that modulate receptor-, or membrane pore- or ion channel mediated activity by detecting intracellular transduction of a signal generated upon interaction of an agonist or substance with said receptor or ion channel is provided, said method comprising:

comparing the amount of reporter gene product expressed in a recombinant cell in the presence of the substance with the amount of product in the absence of the substance; wherein the first recombinant cell contains a reporter gene construct and expresses the receptor or ion channel; and the reporter gene construct contains:

(a) a transcriptional control element that is responsive to the intracellular signal generated by the interaction of an agonist with the receptor or ion channel;

(b) a reporter gene that encodes a translational signal molecule and is in operative association with the transcriptional control element;

wherein the translational signal molecules are able to assemble into VLPs which are preferably released into an extracellular environment.

The amount of reporter gene product expressed in the recombinant cell in the presence of the agonist or substance might be compared with the amount of reporter gene product in the absence of the agonist or a different substance. Preferred substances to be screened applying this assay format comprise cDNAs, genomic DNA fragments, mRNAs, vectors, peptides and proteins, It is particularly preferred that said substance is a cDNA or a cDNA expression library. Instead of transfecting said cells with a cDNA, It is also possible to transform the cell with other types of nucleic acids, such as genomic DNA fragments or mRNAs, or to introduce peptides or proteins into the cell.

This assay regimen allows the identification of gene products interfering with signal cascades within a cell. A transformed cell line expresses a reporter construct under the control of a specific promoter. When the signal cascade connected to this reporter is stimulated then the release of VLPs can be monitored and quantified. Transfection of such cells with either a single or plurality of cDNA molecules capable of expressing a protein product results in influencing the release of VLPs in a stimulated cell if this additional protein product is capable of modulating said signal transduction pathway. Different read-out scenarios are possible:

1. Interaction of the introduced cDNA product with an element involved in the signal transduction cascade stimulated by an agonist results in the abrogation of production and release of detectable VLPs.
2. Interaction of the introduced cDNA product with an element involved in the signal cascade stimulated by an agonist results in an enhancement of production and release of detectable VLPs.
3. Interaction of the Introduced cDNA product with an element involved in the signal cascade in the absence of an agonist results in a stimulation of production and release of VLPs.

Still further if the cDNA molecules introduced are from different sources or material which has been treated differently (e.g. cDNAs from stimulated and non-stimulated cells) then differences with respect to the release of VLPs can also be detected. A transformed cell line expresses a reporter construct under the control of a specific promoter. When the signal cascade connected to this reporter is stimulated then the release of VLPs can be monitored and quantified. Transfection of such cells with either a single or plurality of cDNA molecules capable of expressing a protein product results in influencing the release of VLPs in a stimulated cell if this additional protein product is capable of modulating said signal transduction pathway. One cell line carrying the above constructs is transfected with single or plurality of cDNAs from a specific tissue or stimulated sample. One cell line carrying the above constructs is transfected with a single or a plurality of cDNAs from another specific tissue or stimulated sample to be compared. The influence of the introduced cDNA product on the release of the detectable VLPs under various conditions (stimulated, non-stimulated, induced, constitutive etc) is compared between the two cell populations. A further application relates to screening of subtractive libraries generated from experiments outlined above.

In a further aspect, a recombinant cell is provided which comprises:

DNA that encodes a receptor, or membrane pore, or ion channel; and

A reporter gene construct containing a reporter gene in operative linkage with one or more transcriptional control element that is responsive to an intracellular signal generated by an interaction of an agonist with said receptor, or membrane pore, or ion channel, wherein:

Said reporter gene encodes a translational signal molecule, and

Said translational signal molecules are able of assembling into virus like particles which are preferably released into an extracellular environment.

In a further aspect, the invention also provides reagent kits comprising these recombinant cells. Suitable transcriptional control elements include serum responsive elements, cyclic adenosine monophosphate responsive elements, and elements responsive to intracellular calcium ion levels. The translational signal molecules preferably comprise luminescent polypeptides such as GFP, or enzymes, or entities which act as tags for subsequent labelling with detectable reagents.

Binding, Competition, and Enzymatic Assays, Assays for Determining the Capability of Compounds to Enter into a VLP.

In still another aspect, the invention provides a preferably homogeneous assay for screening a plurality of compounds to determine the degree of inhibition or stimulation of a ligand/binding domain interaction or of an enzyme catalysed reaction by said compounds, or to determine the degree of binding of said compounds to a target molecule. It is also possible to determine the capability of said compounds to enter into a VLP. This assay comprises a step selected from the group consisting of contacting said compounds to be tested with said ligand and said binding domain, contacting said compounds to be tested with said enzyme and substrate for said enzyme, contacting said compounds to be tested with said target molecule, and contacting said compounds with a virus like particle. The binding domain, or enzyme, or target molecule is incorporated into or encapsulated by virus like particles according to any of methodologies described above. Inhibition, stimulation, binding by or entrance of one or more of said compounds causes a change in the amount of an optically detectable label bound to or encapsulated by said virus like particles present in said assay and/or causes a change in a further property of said virus like particles. Amounts of optically detectable signal bound to or encapsulated by individual VLPs are measured through use of optical methods. Alternatively or in addition, the further properties of VLPs are measured (e.g. in an electric field). The degree of Inhibition, stimulation, binding or entrance can be determined by comparing said amounts of said optically detectable signal bound to or encapsulated by individual virus like particles with an amount of back-ground signal in said assay caused by label that is not bound to or encapsulated by said virus like particles. In addition or alternatively, a step of comparing said further property of said virus like particle under study with the property of a reference virus like particle is conducted. The optical methodology preferably comprises methods of confocal microscopy or spectroscopy. Said optically detectable label preferably is a fluorescent ligand, or fluorescent substrate, or fluorescent product of an enzymatic reaction, and said optical methodology comprises fluorescent techniques, in particular fluorescence correlation spectroscopy, fluorescence cross-correlation spectroscopy, fluorescence intensity distribution analysis, fluorescence lifetime measurements, fluorescence anisotropy measurements, fluorescence resonance energy transfer, or combinations thereof. Further properties of said VLP can be e.g. determined by electrical methodologies comprising impedance or dielectrophoresis measurements. Binding domains, or enzymes, or target molecules can be incorporated Into or encapsulated by said virus like particles through fusion to constituents of said VLP, in particular through fusion to capsid or envelope constituents, as explained in detail in the corresponding chapter above. They can however also be incorporated/encapsulated through non-covalent physical forces between constituents of said VLPs and said binding domain, enzyme, or target molecule.

An example of a binding assay, is the measurement of the interaction between a membrane associated receptor molecule and its respective ligand. In this assay the interaction between an excess of labelled ligand either of natural or synthetic origin and a low concentration of its respective functional receptor is quantified by determining the concentration of free (in solution) and bound ligand after an incubation period in which equilibrium between the two constituents has been established. In a heterogeneous assay the free from bound ligand is separated from one another by physical or chemical processes and thus the extent of binding can be calculated. Addition of compounds or molecules capable of interfering with this interaction can be detected by the reduction in the detectable proportion of labelled ligand bound to the receptor. In a homogeneous assay format the free from bound ligand is not separated from one another as the detection system being used to read out the assay can distinguish these populations from one another based upon physical or chemical properties of the ligand or ligand/receptor complexes. Single molecule fluorescence detection methodologies such as fluorescence correlation spectroscopy (FCS) are ideally suited to such assay regimes. In this context the preparation of VLP populations which carry the specific functional target molecule incorporated into the lipid envelope free from contaminating proteins (as compared to vesicle isolated from cells) represents the ideal reagent to perform ligand binding studies. The target is homogeneous and is in its native conformation and environment thus proving to be an ideal material for receptor ligand binding analysis. As compared to other materials used for the analysis of receptors, such as either purifed receptor or enriched receptor in membrane vesicle preparations, both sources of which suffer from the difficulties and disadvantages as described above, then the VLPs carrying a functional integral membrane receptor offer a number of distinct advantages:

Homogeneous material with respect to the number of target molecules on the surface of each particle.

The target molecules are presented in an enriched and purified form with minimal amounts of contaminating proteins thus reducing the background as compared to complex mixtures found in membrane preparations.

The VLPs are easily harvested and separated from the cells producing them.

Because of the nature of their synthesis and production they are extremely stable reagents.

The binding assay principle can also be applied to other types of integral membrane proteins whose normal function is not that typified by a receptor. In this context a large number of integral membrane proteins which function as channels controlling the influx and efflux of small inorganic ions and complexed substances can also be assayed according to this principle. A number of small molecules or peptide mimetics have been characterised which bind with high affinity to the portions of the channel responsible for the pumping of the respective ions either out of or into the cellular compartment and thus function as antagonistic ligands. As described for ligand receptor interactions small molecules interacting with the channels can thus be detected again in either a heterogeneous or a homogeneous format by the quantification of the inhibition of the binding of the labelled ligand. Again preparations of VLPs expressing such target molecules on the surface of these enveloped particles in their correct conformation and chemical milieu results in optimal reagents for such analysis.

This principle for the binding of a specific ligand to a more complex interacting partner is not restricted to receptors or ion channels found as integral membrane proteins but is also applicable to such molecules isolated as a soluble functional protein away from their natural lipid environment in a soluble aqueous environment.

Furthermore this assay principle is also applicable to soluble cytoplasmic or nuclear proteins which either function as a receptor (e.g. nuclear hormone receptors) or have an enzymatic activity, in which case again either labelled ligands for the receptor or a labelled non-hydrolysable enzyme substrate can be used to detect compounds which interact with the protein in question. Quantification of this interaction in either a heterogeneous or homogeneous format forms the basis for an assay in which compounds interacting with the target under experimentation can be detected. In this context the target molecules under study can be incorporated specifically into enveloped VLPs and thus represent a reagent whereby the target molecule is encompassed by a natural cellular boundary, the plasma membrane. Molecules which interact with this target (especially those small molecules of pharmaceutical relevance) normally have to traverse this barrier, an aspect which is not assayed for directly when utilising binding assays on purified components in an aqueous environment. However when using VLPs in this assay format then not only is one able to determine the competing interaction of a small compound for a ligand binding to its cognate receptor (or a substrate interacting with an enzymatic activity) but also Its property to traverse the plasma membrane, a natural biological barrier thus adding value to the analysis.

VLP Solid Phase Interactions

In a further aspect, the invention relates to measurement of the interaction between a membrane associated protein (e.g. an integral membrane receptor, ion-channel, adhesion molecule or a pore complex) and a compound attached to a solid phase, in particular a bead. With the development of combinatorial chemistry and in particular solid phase combinatorial chemistry, assays which are capable of detecting the interaction between a target molecule and beads coated with a pharmaceutically relevant small molecules are of great interest. However such assay formats have until now mostly been limited to the use of purified soluble target molecules associated with a detectable label (for example a fluorescence label) required for analysis and quantification of the interaction. The use of more complex integral membrane proteins in this application is hampered by this requirement due to the reasons described in other chapters of the present patent application. The use of VLPs displaying such an integral membrane molecule incorporated into the lipid envelope makes the development of such assays possible as described below. VLPs displaying the target molecule of interest can be stained with membrane permeable dyes which make the detection and quantification of the VLPs by optical methods possible. When such VLPs are added to a mixture of beads coated with a plurality of chemical substances, which represent potential binding partners, and are allowed to incubate to equilibrium then binding partners can be detected by the subsequent direct labeling of the beads due to interaction with the labeled VLP molecules. In combination with specific, preferably confocal, detection and single positive bead isolation methodologies then compounds can be detected which interact specifically with integral membrane proteins. A further embodiment includes the direct labeling of the VLP in which the target molecule of interest has been incorporated by the fusion of the target molecule directly with a luminescent peptide or polypeptide thus enabling the direct detection and quantification of the VLP without the usage of membrane permeable dyes. A further embodiment of the methodology would be to use fluorescent conjugates which covalently bind to reactive thiol groups either on the surface or in the interior VLP carrying the target molecule of interest to specifically label the VLP thus enabling the detection of the interaction between the VLP and the respective bead as described above.

Interaction Between Target Molecules Incorporated into VLPs

In yet another aspect, the invention discloses an assay for screening a plurality of compounds to determine the degree of inhibition or stimulation of an interaction between at least two target molecules, in which the said assay comprises adding a liquid suspension of first target molecules incorporated into first virus like particles and a liquid suspension of second target molecules incorporated into second virus like particles to a plurality of containers. The assay further comprises, adding a plurality of compounds to be screened for said inhibition or stimulation individually or in combination to said plurality of containers and incubating said target molecules incorporated into said virus like particles and said compounds. The assay is analysed by measuring at least one property of said virus like particles and determining the degree of inhibition or stimulation of said interaction between said target molecules by one or more of said compounds. It is preferable that said target molecules are incorporated into said virus like particles through fusion to capsid or envelope constituents of said VLPs or according to the above disclosed method in a noncovalent manner. Preferably an optically determinable property of said VLP is measured, e.g. by methods of confocal microscopy or spectroscopy, by the above disclosed fluorescent techniques (such as fluorescence cross-correlation spectroscopy, fluorescence Intensity distribution analysis, fluorescence lifetime measurements, fluorescence anisotropy measurements, fluorescence resonance energy transfer, or combinations thereof), light scattering, or a further property by impedance measurements, dielectrophoresis measurements, or otherwise. In a preferred embodiment, said signal molecules comprise a reporter entity, preferably a luminescent reporter, in particular green fluorescent protein or mutants thereof.

Cell-cell interactions or cell matrix interactions assays are of great importance in the areas of immunology and inflammation where the interaction between cells and cell matrix interfaces is of great importance. Difficulties associated with this assay regime are usually associated with the difficulties in utilising viable cells in a uHTS screening background, as such an undertaking is extremely time consuming and expensive with inter-assay variation making the statistical analysis and quality control difficult to standardise. It is possible to use purified constituents from recombinant cell populations which over-express the interacting partners although this approach usually results in the reduced affinity of the system. This reduction in affinity (which of course does not reflect the physiological state) has a number of causes, e.g. conformational changes after removal of the constituents from their natural environment (e.g. a lipid bilayer). In a number of cases such binding partners (target molecules) are not single molecular entities but are complexes of either homologous or heterologous constituents which make their purification difficult if not impossible. The use of alternative materials such as membrane preparations imposes limitations on the assay design and detection, If at all feasible. The use of VLP methodology alleviates a number of these problems and thus represents a progress in the design and performance of such assays. In principle if one population expressing one target molecule or target complex (composed of either homologous or heterologous constituents) is incubated with a second population of VLPs expressing the interaction partner target molecule (composed of either homologous or heterologous constituents) and the interaction is allowed to proceed to equilibrium, then aggregates of interacting VLPs will be generated. Utilisation of detection technologies which can differentiate between single VLPs and aggregates of VLPs either by physical attributes of these populations (for example light scattering properties) or specific design of reporter molecules incorporated into the two different VLP populations which can be differentiated from each other (e.g. luminescent proteins or membrane dyes) results in a sensitive detection and quantification of the different populations represented in this mixture. This principle forms the basis for an assay format applicable to uHTS, in that addition of compounds which interfere with the interacting partners on the different VLP populations will Influence the proportion of aggregated VLPs as compared to controls.

Intracellular Protein-protein interactions.

A further assay format of great interest in the search for new pharmaceuticals is that of influencing protein-protein interactions with small molecules. This can be approached in a number of ways, one of which has been described above in the rubric ligand-receptor interactions of purified constituents in an aqueous environment. However, a more physiological environment for the analysis of protein-protein interactions would be of great benefit as compounds isolated in the above assay have to be tested and evaluated usually in cellular systems. Such cellular systems represent a number of challenges as compared to the more simple binding assay resulting in the failure of a large number of potential modulators to be further developed as promising drug candidates. One such limitation again is the ability of such compounds to traverse the natural boundary of the cell represented by the plasma membrane. Analysis of protein-protein interactions in eukaryotic cells has been restricted at the uHTS level due to the complexity of the system and has only received attention in yeast where the two-hybrid-system has been used extensively as an assay system to identify and clone protein partners involved in protein-protein interactions, with very little application in pharmaceutical drug, screening. Although very useful as a methodology for the applications mentioned above the system does suffer from a number of limitations. Firstly the analysis is performed in yeast which in some respect makes experimentation easier but of course certain biochemical reactions are different from those in higher eukaryotes, thus introducing a certain degree of redundancy. Secondly the interacting partners have to be transferred to the nucleus and can in some instances thus reduce the analysis of the respective proteins down to fragments or domains of the respective targets. This may reduce the affinity and specificity of the system resulting in a loss of information from the analysis. Finally the system also suffers from the high level of background resulting in a large percentage of false positives. In this assay format the VLP methodology offers a number of advantages over the above described methodology. The assay is based upon the following format in which the signal molecules comprise two amino acid sequences: one which confers on the signal molecules the ability to assemble into VLPs which are preferably released into the extracellular environment and fused to it is a first interacting molecule of choice. The target molecule of choice comprises also two amino acid sequences: one which interacts specifically with the first interacting molecule and another fused thereto which is a reporter molecule. This reporter is detectable and quantifiable in either a heterogeneous or homogeneous assay after incorporation into a VLP. Expression of these two fusion molecules in the same host cell results in the synthesis of two chimaeric molecules which interact specifically with one another. If this is the case then a complex will be formed consisting of signal-target. Thus the two functional entities, signal and target are brought together resulting in the incorporation of the reporter Into preferably released VLPs due to the property of the signal molecule to induce the formation of and become incorporated into VLPs which are subsequently released into the extracellular environment. A cell expressing these constituents thus forms the basis for an assay format which can be used to analyse protein-protein interactions with the respective protein molecule pairs of interest. In a control experiment the release of detectable VLPs over a certain period of time is quantified and compared to the release of detectable VLPs from a cell culture which has been treated with a compound potentially capable of traversing the plasma membrane and modulating the specific protein-protein interaction of the respective protein molecules localised in a compartment within the cell. Thus the assay delivers a direct read out measured external to the cell but reflecting interactions occurring in a physiological environment within the cell.

In more general terms, the invention provides an assay for determining intracellular protein-protein interactions, said assay comprising:
(a) co-expressing in recombinant cells (i) target molecules comprising a first and a second amino acid sequence, the latter of which is a preferably luminescent reporter, and (ii) signal molecules comprising a first and a second amino acid sequence, the latter of which confers on the signal molecules the ability to assemble into VLPs which are preferably released into an extracellular environment;
(b) measuring the presence or absence of said reporter within said VLPs; and thereby
(c) determining the degree of protein-protein interaction between the first amino acid sequence of a target and the first amino acid sequence of a signal molecule.

In even a more general terms the invention provides an assay for determining intracellular protein-protein interactions, in which the said assay comprises providing a recombinant cell which comprises a first DNA that encodes a first fusion protein consisting of at least two entities, wherein the first entity is a molecule capable of inducing the formation and preferably release of virus like particles into an extracellular environment, and the second entity is a protein under study as well as a second DNA that encodes a second fusion protein consisting of at least two entities, wherein the first entity is a preferably luminescent reporter and the second entity is another protein under study. In a further variant, the recombinant cell comprises a first DNA that encodes a molecule capable of inducing the formation and preferably release of virus like particles into an extracellular environment; a second DNA that encodes a protein under study, wherein both said molecule and said protein under study are adapted to functionally operate in a non-covalent manner with each other; and a third DNA that encodes a fusion protein consisting of at least two entities, wherein the first entity is a preferably luminescent reporter and the second entity is another protein under study. In another variant, the recombinant cell comprises a first DNA that encodes a fusion protein consisting of at least two entities, wherein the first entity is a molecule capable of inducing the formation and preferably release of virus like particles Into an extracellular environment, and the second entity is a protein under study; a second DNA that encodes a preferably luminescent reporter; and a third DNA that encodes another protein under study, wherein both said preferably luminescent reporter and said another protein are adapted to functionally operate in a noncovalent manner with each other. In a final variant, the recombinant cell comprises a first DNA that encodes a molecule capable of inducing the formation and preferably release of virus like particles into an extracellular environment; a second DNA that encodes a protein under study, wherein both said molecule and said protein are adapted to functionally operate in a non-covalent manner with each other; a third DNA that encodes a preferably luminescent reporter; and a fourth DNA that encodes another protein under study, wherein both said preferably luminescent reporter and said another protein are adapted to functionally operate in a non-covalent manner with each other. In this assay the components are expressed and the degree of protein-protein interaction is determined by measuring the presence or absence of said preferably luminescent reporter within said virus like particles preferably released into the extracellular environment. This assay is preferably homogeneous. The presence or absence of said preferably luminescent reporter within said virus like particles is preferably measured by confocal microscopy or spectroscopy, in particular by the use of fluorescent techniques, such as fluorescence correlation spectroscopy, fluorescence cross correlation spectroscopy, fluorescence intensity distribution analysis, fluorescence lifetime measurements, fluorescence anisotropy measurements, fluorescence resonance energy transfer, or combinations thereof.

Preferably, this assay principle comprises contacting said recombinant cells with compounds/substances to be screened for their capability to interfere with said protein-protein interaction. Compounds/substances to be screened include cDNA expression libraries, genomic DNA fragments, mRNAs, peptides, proteins and low molecular weight substances. In a preferred embodiment, this assay regimen can be used for the identification of gene products interfering with protein-protein interactions within the cell. Before addition of the cDNA library, a transformed cell expresses the above mentioned constructs. The interaction of these proteins results in the release of detectable VLPs. By transfecting the cell with a single or plurality of cDNA molecules capable of expressing a third protein product then this additional protein product when capable of interacting with one of said primary or second protein molecules will affect the release of detectable VLPs. In this way, molecules capable of influencing this interaction between the first and the second protein molecule can be identified. These molecules might only interfere with the binding between first and second protein molecule, or they might constitute even new binding partners for one of said first or second protein molecules. Included in this model are a number of scenarios:

a) The introduced cDNA codes for a protein that interacts with the protein molecule fused to the reporter molecule thus inhibiting the interaction between the signal fusion and the reporter fusion. The result is that VLPs are released that do not carry a reporter molecule. Nevertheless, these VLPs can be distinguished from VLPs carrying the reporter molecule.

b) The introduced cDNA codes for a protein that interacts with the protein molecule fused to the signal molecule thus inhibiting the interaction between the reporter fusion and the signal fusion. The result is that VLPs are released that do not carry a reporter molecule but encapsulate the introduced gene product of said cDNA, whose presence or activity can be assayed for directly in the released population of VLPs. These VLPs can also be distinguished from VLPs carrying the reporter molecule.

c) There is no interaction between the introduced cDNA product and either the signal or the reporter fusion products. Thus the release of VLPs carrying a detectable reporter is not hindered.

Instead of transfecting said cells with a cDNA, it is also possible to transform the cell with other types of nucleic acids, such as e.g. genomic DNA fragments or mRNAs, or to introduce peptides or proteins into the cell.

Assays on transport/Translocation Polypeptides.

A further application of the VLP methodology involves the identification of sequences which are able of targetting or translocating proteins to the plasma membrane. Such sequences could include specific signalling sequences responsible for the translocation of polypeptide molecules from the cell into the extracellular medium of cultivated cells in vitro or for the translocation of proteins in vivo. In this application a mutant of a specific signal protein is utilised (in particular the retroviral Gag protein) which—although it is synthesised In the host cells—the protein is defect in its ability to translocate the protein to the plasma membrane where it then induces the formation and release of VLPs. The mutation in the Gag protein which leads to this defect is preferably encoded by a Glycine residue at position two in the polypeptide chain and is adjacent to the Methionine start codon. In this application DNA sequences derived from the 5' ends of cDNA molecules are fused to the defective gag gene using standard molecular biological methodologies. These constructs are then transfected into cells and if the fusion is in the correct reading frame and the added 5' sequence then codes either for a secretory protein possessing sequences responsible for the translocation of the native protein to the plasma membrane or indeed if the native protein encoded by the cDNA is itself an integral membrane protein then the defect in the mutated Gag protein will be alleviated. Thus the result of this rescue will be that the defective Gag protein would be transported to the plasma membrane where it could induce the formation and subsequent release of VLPs into the extracellular medium. In a further embodiment if the Gag protein is modified to comprise a reporter polypeptide fusion at its C-terminus (such as a luminescent protein) then this molecule will be encapsulated into the VLP thus enabling the efficient detection of the released VLP.

Consequently, an assay for identifying nucleic acid sequences which encode intracelullar transport polypeptides or membrane associated translocation polypeptides is provided, said assay comprising:

(a) providing a recombinant cell which comprises a DNA that encodes a fusion protein comprising a first and a second amino acid sequence, wherein said first amino acid sequence confers on the fusion proteins the ability to assemble into VLPs and wherein said first amino acid sequence does not confer on the fusion proteins the ability to be transported to a cellular membrane and/or wherein said first amino acid sequence does not confer on the VLPs the ability to be released into an extracellular environment by a budding process through said cellular membrane, and said second amino acid sequence is a polypeptide under study;

(b) expressing said fusion proteins;

(c) measuring the presence or absence of VLPs in said extracellular environment; and thereby (d) identifying DNA sequences which encode intracellular transport polypeptides or membrane associated translocation polypeptides.

Preferably a library of DNA molecules is screened in a plurality of recombinant cells. The first amino acid sequence is preferably covalently linked to the C-terminus of said second amino acid sequence. This fusion protein preferably comprises a luminescent reporter covalently linked to the C-terminus of said first amino acid sequence. The reporter is e.g. GFP or a mutant thereof. The first amino acid sequence is preferably encoded by a mutant gene coding for a virus capsid or envelope protein, or by a mutant gene coding for a precursor of a virus capsid or envelope protein. It might however alternatively be encoded by a mutant gene coding for a capsid or envelope protein of a VLP, or by a mutant gene coding for a precursor of said capsid or envelope protein. Preferably, said first amino acid sequence is a structural protein encoded by a mutant of the gag-gene of retroviruses, in this case, the mutant results preferably from the replacement of a specific amino acid at a specific position in the polypeptide chain of the signal molecule. Preferably the position two after the initiation codon methionine is changed to any residue which codes for an amino acid that cannot be modified by myristoylation.

Again said assay is preferably homogeneous. Once again the presence or absence of virus like particles in said extracellular environment is e.g. measured by optical methods, preferably confocal microscopy or spectroscopy. In particular, the presence or absence of virus like particles in said extracellular environment is measured by use of fluorescent techniques, in particular fluorescence correlation spectroscopy, fluorescence cross-correlation spectroscopy, fluorescence intensity distribution analysis, fluorescence lifetime measurements, fluorescence anisotropy measurements, fluorescence resonance energy transfer, or combinations thereof.

Modulators of signalling Pathways or Physiological Status of Cells, Further Functional Genomics Aspects.

A large number of diseases or physiological statuses are associated with well defined phenotypes which are reflected by certain molecules and their concentration or an interaction of such molecules as surrogate markers. These markers can act as well as surrogates for various other additional concentrations or interactions of molecules upstream and downstream in such a signalling cascade or signalling network. As described above, all these molecules or interactions of molecules can be considered as molecular targets for the discovery of interfering pharmaceutical or otherwise bioactive molecules. Such interfering molecules might be low molecular weight compounds, pharmaceutical proteins or even molecules based on interacting cells or transforming genes. They might be considered as candidates for novel hits, leads or drugs or to identify natural agonistic or antagonistic mediators.

Marker molecules or interactions of marker molecules or changes in concentration or changes of interactions of these marker molecules can particularly be used to identify a new gene's activity with formerly undiscovered biological function. Tools to easily identify biological functions of unknown novel genes or gene products are of utmost importance in so called functional genomics applications to decipher the biological role of novel genes and their potential as drug targets or drugs themselves. Such an approach would be applicable, if an activity of a genetic material or gene derived product within a cell would for example act upstream of such a marker molecule as to affect these molecules or interactions of such molecules. A robust read-out technology for characteristic cell based physiological endpoints applicable to large arrays of transiently or stably transformed cells would be of utmost advantage to discover orphan gene functions individually or for larger arrays thereof. Orphan genes are often generated by differential display analysis of mRNAs or genome sequencing. They could also be a complete bank of expression clones.

With the results of mass sequencing such as from the sequencing the human genome, orphan genes need to be tested whether their products are of importance for certain signalling pathways within cells. Unknown genes after transfer into cells can thus be elucidated as to whether they influence such a biological endpoint if VLPs indicate for example the biological signalling endpoint which could be the induction of apoptosis or the secretion of surface antigens as differentiation factors or the secretion of Aβ42-peptides as indicators for Alzheimer-pathogens or the induction of stress genes or indicators of toxicity to mention a few physiological endpoints. Generating such information on unknown genes is considered as functional genomics.

The above mentioned generation or modification of detectable VLPs from recombinant cells as a result of the cell's interaction with bioactive compounds can preferably be applied as a signal to indicate the influence of one or more genetic elements or their antisense products or the influence of a protein or protein binding entity following the uptake by such by a cell or population of cells. Genes or gene products such as peptides or proteins or sense or antisense RNA or correspondingly reacting molecules such as PNAs or neutralizing antibodies can be transported inside cells by various well known procedures such as infection with suitable vector systems, using cellular transport mechanisms, DNA transformation, conjugation or injection.

Such an approach to functional genomics becomes possible due to efficient technologies to introduce genetic material or gene derived products such as mRNA, processed mRNA, truncated and modified forms of RNA such as partial RNA sequences or antisense DNA or RNA sequences or polymers which interact with such sequences like PNAs or proteins or polypeptides or modified forms thereof. Efficient and miniaturized transformation technologies, injection technologies such as gold associated Introduction of nucleic acids, microinjection of mRNA in fertilized oocytes, technologies of infecting cells with infectious agents such as recombinant viruses or endocytotically mediated uptake or the uptake of reagents to specifically knock out genetic functions on the protein level such as selective and or reactive antibodies or peptide binders as well as handling technologies of single cells and small populations of cells as described in European patent applications 96 939 933.6, 97 953 804.8, 97 952 938.5 or International patent applications PCT/EP 97/07218, PCT/EP 98/08370, PCT/EP 99/02380, PCT/EP 99/04469 and PCT/EP 99/04470 (the contents of which are herein incorporated by references) in combination with assay technologies such as those described in this patent application allow to functionally decode the effect of functionally unknown genetic material or gene derived products. In individual or parallelized experiments, such genetic material or gene derived products or knock-out reagents at the level of proteins are introduced in single cells or populations of cells. If the respective genetic material or gene derived product is capable of inducing a detectable VLP signal as a response to a cellular signalling pathway such a function can be assigned to such a genetic material or gene derived product.

Often new genetic information can be identified via the function of its encoded protein, for example a protease, a kinase or phosphatase. In addition, information on the type of tissue and physiological condition of expression might be known. This, however, is not sufficient an information to validate such a target. The technology according to the present invention is an important tool in the discovery of novel molecular targets to treat a disease or to Interfere with another cellular property such as in crop design to improve its economical value.

With respect to functional genomics and drug screening, the technology according to the present invention also discloses a method for identifying substances which specifically modulate signaling pathways and/or a physiological status of a cell by influencing members of such signaling pathways, said method comprising:

comparing the amount and/or properties of a reporter gene product expressed in a recombinant cell in the presence of the substance with the amount and/or properties of product in the absence of the substance; wherein said cell contains a marker or surrogate marker of said signaling pathway, and the production and/or properties of said reporter gene product or its release from the cell is responsive to the properties and/or amount of said marker or surrogate marker or to an intracellular signal generated by said marker or surrogate marker, and said reporter gene product comprises (i) a signal molecule and optionally (ii) a detectable moiety, wherein said signal molecules are able to assemble into virus like particles which are preferably released into an extracellular medium.

It is particularly preferred that the reporter gene product is encoded by a reporter gene construct which contains a transcriptional control element that is responsive to the properties and/or concentration of said marker or surrogate marker or to an extracellular signal generated by said marker or surrogate marker. Preferably the transcriptional control element includes at least one regulatory element selected from the group consisting of serum responsive elements, cyclic adenosine monophosphate responsive elements, and elements responsive to intracellular calcium ion levels.

In a preferred embodiment, said substance is selected from the group consisting of low molecular weight compounds, nucleic acids, peptides/proteins, or PNAs. The nucleic acid might be chosen from the group consisting of genomic DNA, cDNA, mRNA, antisense sequences, or a fragment or modified nucleic acid of the foregoing. Said protein is preferably an antibody.

Another application of the VLP-technology according to the present invention is to study the induction of expression of novel genes or processing of posttranscriptional signals derived from novel genes as a result of the activity of a lead compound or other molecules on a cell line or as a result of a transformation process of a cell line by uptake of defined regulatory molecules, genes, antisense molecules or mRNAs or selective reagents acting on the protein level.

One possibility is to use an expression library of cells with fusion proteins expressing detectable signals in VLPs after activator deactivation of such genes. A direct way to observe all the genes co-expressed upon action of a specific stimulus is important to follow in order to pick additional drug target candidates to selectively activate certain biological function by selective upstream intervention within a signalling chain.

A physiological endpoint can also be a stress response which is examined in biosafety or bioavailability testing, such as those tests described as early ADME/tox assays.

VLPs produced according to the present invention can e.g. also be used for the functional analysis of ion channels or components of ion channels. For example the Glutamate receptor can be located in the membrane of VLPs loaded with Ca indicating dyes such as Fura-dyes and influx of free Ca2+ can be monitored in presence or absence of antagonists or agonists.

VLP-based Orphan Receptor Assays.

According to the present invention, VLP technology can also be applied in combination with a technique for a specific molecular tagging of GPCRs which is necessary if the natural ligand is unknown (details of this techniques are disclosed in WO 98/39660 the contents of which are herein incorporated by reference). Upon interaction with either a putative or a synthetic ligand the GPCR changes its conformation resulting in the exposure of reactive thiol groups which are then capable of reacting with a specific dye. This ligand-induced response can be used to screen for compounds which activate or modulate the receptor either as agonists or antagonists. Applications of this competitor-free assay technology include:

Identification of agonists for an orphan receptor from a ligand library
Identification of the presence of a receptor for a putative ligand
Discrimination between agonists and antagonists
Detection of antagonists (either anti-receptor or anti-antagonist) by inhibition of agonist-induced labeling Complexing of Molecules in Virus like Particles.

It has been shown for many families of cell surface receptors that the formation of multi-unit complexes, i.e. homo- or heterodimers or oligomers, is an essential requirement for the formation of structurally and functionally active units, adding further complexity to cellular signalling processes. This complexity has important implications for the design of screening strategies for new drugs. Very recently, this concept has also been recognized to be relevant for the single largest family of cell surface receptors, the G-protein coupled receptors (Salahpour et al., Trends Endocrinol Metabol 11, 163-168, 2000). For instance, individual subtypes of the somatostatin receptor assemble as functional homo- and heterodimers (Rocheville et al., J. Biol. Chem. 275, 7862-7869, 2000). Further, receptors for dopamine and somatostatin are capable of forming hetero-oligomers with enhanced functional activity (Rocheville et al., Science 288, 154-157, 2000). Yet another example is the interaction of m- and d-opioid receptors to form oligomers, with the generation of novel pharmacological and G-protein coupling properties (George et al., J. Biol. Chem. 275, 26128-26135, 2000). Further, if one considers for example a defined GPCR in the cell membrane of a particular cell, then in its normal high affinity state this individual protein Is associated (complexed) with a variety of other protein units involved in the signaling processes stimulated after interaction of an agonist with the said receptor. These proteins (the so called G-proteins of which there are $\alpha$, $\beta$ and $\gamma$ subunits) interact with the respective receptors with such high affinity and specificity that they can be enriched for and isolated by Immune precipitating the said receptor in membrane lysed cells.

Thus, it would be of considerable practical benefit to Incorporate, or encapsulate, or otherwise physically associate into virus like particles not only single, individual target molecules, but to assemble therein whole functional complexes of target molecules. These complexes may consist of, but are not limited to, different subunits or subtypes of an individual target molecule, or different target molecules, such as different classes of GPCRs, or target molecules and their different accessory, ancillary, or other associated factors, in particular effector proteins such as G-proteins.

The present invention provides a method which achieves this goal by-tagging one of the complexing components, hereinafter referred to as the first component, and thus inducing the interaction with a tagged signal molecule and effecting the subsequent incorporation or encapsulation into VLPs, or association with VLPs. Due to the formation-of homo- or heterodimers, or homo- or hetero-oligomers of the tagged first component of a target molecule complex with an untagged component, hereinafter referred to as the second component, either endogenously present in the host cell, or co-expressed, one is able to incorporate specific interacting partners operating in a complex unit into a virus like particle. This was examined for the human Endothelin A receptor which was co-expressed in its tagged form with a tagged Gag protein molecule. The resulting VLPs which were released into the cell culture supernatant were demonstrated by western blot analysis to contain at least the endogenous insect $\alpha$ G-protein subunit (see FIG. 25).

The same priniciples which have been described with regard to the production and uses of virus like particles having Individual target molecules also apply to virus like particles with target molecule complexes.

Use of Virus like Particles for the Concentration, Isolation and Purification of Recombinant Molecules A further application of the VLP methodology involves the specific incorporation or encapsulation into, or physical association with VLPs and the subsequent release of such VLPs into the cell culture supernatant, whereby the VLPs can then be used as biochemical material in the first step in a purification protocol.

In a preferred example an integral membrane protein of interest is incorporated into the VLP according to the methodology described earlier. In the initial step the said molecule is thus incorporated into an environment which is similar to that in which it is usually found as a functional entity, that is the plasma membrane. This specific incorporation also results in a concentration step in which each VLP carries only a small proportion of endogenous integral membrane proteins as compared to the concentration of the membrane protein of interest. Assuming that the protein of interest is expressed at copy numbers of 1000 per eukaryotic cell, then their respective concentration within the cellular volume of approximately 1 pl is approximately 1 nM. At high cell densities of 1000 cells per pl within the medium, the concentration is approximately 1 pM within the total sample. If such proteins, however, are expressed on particles of 100 nm diameter in copy numbers of approximately 100 per particle, their local concentration is enhanced to approximately 1 mM. VLPs released to the medium by exocytosis, lysis, budding or related mechanism can easily be concentrated to 10 pM, meaning the protein of interest is about 10 nM, just as the physiological concentration within a cell. With the technology according to the present invention, target molecules can be concentrated on the surface or within homogeneous VLPs. Subsequent isolation and concentration of the VLPs thus constitutes the first step in a purification protocol in which the target molecule of interest can then be further purified by standard biochemical means. This initial purification concentration step (incorporation in a VLP) can be utilized for both integral membrane proteins and also soluble cytoplasmic proteins which can be encapsulated within the VLP after interaction with the gag protein via the specific complementary coiled coil sequences. This methodology can also be applied as a genomics strategy in which gag can be fused to a target protein of interest either covalently or non-covalently and introduced into a plurality of cells either expressing a plurality of cDNA fusions or endogenous proteins coding potentially for partners which are capable of interacting with the target of interest fused to gag. If this interaction is specific and of considerable affinity then interaction partners can be incorporated into the VLPs and subsequently enriched and purified by standard biochemical methods. This methodology offers a number of advantages as a purification strategy; Over-expression of some recombinant proteins in cells can result in increased toxicity to the host cell. Where cells are continuously incorporating the recombinant protein into VLPs, which are being continuously released from the cells then the recombinant protein in question is present at a lower concentration in the cell which may reduce the toxic effects. Due to the fact that the target proteins are incorporated specifically into the VLPs as compared to other contaminating proteins (found at lower concentrations as compared to whole cells) the VLP strategy enriches the target of interest in one step.

Further Aspects of the Present Invention.

With the VLP technology according to the invention, unique assay systems based on cell-like particles have been developed providing a native cellular envionment but avoiding the pitfalls of cellular assays. VLPs released from cells contain e.g. functional GPCRs integrated into a cellular membrane. VLPs, being small, fairly homogeneous particles whose behaviour is similar to that of individual molecules, are a perfect biological match to preferably confocal single-molecule detection platforms. One VLP carries up to 100 molecules of a target—such as a specific GPCR—resulting in the simultaneous enrichment of the respective target and amplification of the read-out. VLPs are a means to one-step production, concentration and purification of a target, and function additionally as stable storage system. VLP technology provides unprecedented speed in the adaptation of cell-based assays to screening. This speed, comparable to that typically achieved with soluble receptor or biochemical assays, is combined with improved robustness and accuracy of data generated.

Advantages of the VLP assay technology according to the present invention are the following:

Cassette-based assay set-up→fast assay development

High concentration of target molecule→increased read-out intensity

Selective target Incorporation/encapsulation→low background & high precision

Native cellular assay environment→functional analysis of transmembrane receptors such as GPCR Inducible target-VLP production→target on demand Target production, concentration & purification in a single step→rapid & simple assay procedures Homogeneous assay system→mix-and-measure procedure Highly sensitve→large dynamic range Averaging over representative cell population per data point→low number of false-positives/-negatives Miniaturized assay formats→save precious compounds & reagents Stable storage system for targets→easy re-screenability Application of confocal detection technologies, preferably fluorescence technologies→high performance screening The technology has the capacity to physiologically concentrate proteins of otherwise low concentration within a cell or in the respective cell culture medium and at the same time enrich a certain type of molecule of interest by orders of magnitudes compared to other cellular constituents from an otherwise very complex matrix.

Weak, or low-affinity interactions between proteins, or other molecules play an important role in cellular signalling processes. These types of interactions are often made possible by the maintanance of a locally high concentration of the interacting partners in subcellular compartments, particles, or membrane domains. An advantage of the methodology according to the present invention is the conservation of the locally high in vivo concentrations of interacting molecules during the release of the virus like particles into the cell culture medium. Assuming that the protein of interest is expressed at copy numbers of 1000 per eukaryotic cell, then their respective concentration within the cellular volume of approximately 1 pl Is approximately 1 nM. At high cell densities of 1000 cells per μl within the medium, the concentration is approximately 1 pM within the total sample. If such proteins, however, are expressed on particles of 100 nm diameter in copy numbers of approximately 100 per particle, their local concentration is enhanced to approximately 1 mM. VLPs released to the medium by exocytosis, lysis, budding or related mechanism can easily be concentrated to 10 pM, meaning the protein of interest is about 10 nM, just as the physiological concentration within a cell. With the technology according to the present invention, target molecules such as GPCRs can be concentrated on the surface or within homogeneous VLPs, resulting in a signal enhancement with respect to read-out techniques (e.g. confocal fluorescence measurements).

The method can also be used to display molecules with cellular toxicity, such as ion channels, or molecules with a high tendency for aggregation, denaturation or precipitation in producer cells. The product synthesised is continuously exported from cells thus preventing accumulation to levels which are toxic to the cell.

The continuous or induced production of said VLPs allows one to run kinetic assays over longer time-frames of in vitro cultivation of cells.

VLP reagents or drugs can be stored easily and conveniently over longer periods of time without measurable loss of biological activity.

Selection of antibody producing cells and preparation of antibody and Fab producing VLPs is rendered possible according to the invention.

The system can be applied for the study of regulated protein/protein interactions in signal transduction pathways. Signal transduction pathways are often regulated by selective protein/protein interactions, which can be considered as targets for therapeutic interaction whereby the affinity of the interaction is regulated by protein induction
selective protease cleavage/differential cleavage
mRNA processing/maturation
phosphorylation/dephosphorylation
electrophysiological control
myristoyation, glycosylation and other modifications.

While innercellular protein/protein interactions are difficult to intervene with due to often large areas of protein/protein interactions, the regulatory steps rendering the proper constitution and conformation of one interacting partner can well be subject of effective therapeutic intervention, e.g. by kinase inhibitors.

The method described herein refers to cell based functional assay system reporting on the proper read out of the innercellular protein/protein interaction. The effective protein/protein interaction under physiological conditions is indicated by VLPs. One interacting partner is linked e.g. by the inventive technique to the Gag-signal protein. The presumably interacting protein is expressed and innercellularly labelled as a direct fusion or in a non-covalent way to a detectable marker e.g. a fluorescent protein or peptide. If both or one interacting partner is properly processed by the regulatory modification system mentioned above both proteins will interact physiologically, be packaged and exported from the cell. The distribution of labelling of VLPs or the ration of labelled or unlabeled VLPs will report on the functionally status of the modifying cellular system. This mode of detection has the advantage, that the signal reports linearly on the effect of regulation and "freezes" the status once the VLP is released into the medium.

A variation of this detection system can be applied for the detection of processing steps for secreted proteins, which will not be encapsulated. One example for such a detection system refers to the secretion of C-terminally differentially processed peptides such as Aβ40 and Aβ42 created by two different types of secretase activities. Both peptides can be N-terminally linked to the modified signal sequence as described for outer-membrane receptors or linked to an extracellular C-terminus provided by a protein which is linked to a signal sequence. With differentially labelled antibodies recognising the two variant C-termini of the Aβ peptides, the released VLPs can be analysed to measure the differentially activities of both secretases activities.

The following drawings form part of the present specification and are included to further demonstrate certain aspects of the invention. The invention may be better understood by reference to one or more of these drawings in combination with the detailed description of specific embodiments presented herein, FIG. 1 is a diagrammatic representation of the principle of VLP budding from host cells, Assembly of retroviruses takes place by a budding process at the cellular plasma membrane. Studies with several retroviruses have demonstrated that the Gag poly-protein expressed in the absence of other viral components is self sufficient for particle formation and budding at the cell surface as depicted in this figure. It has been reported that the amino terminal region of the Gag precursor is a targeting signal for transport to the cell surface and membrane binding which is required for virus assembly.

Figure 2:
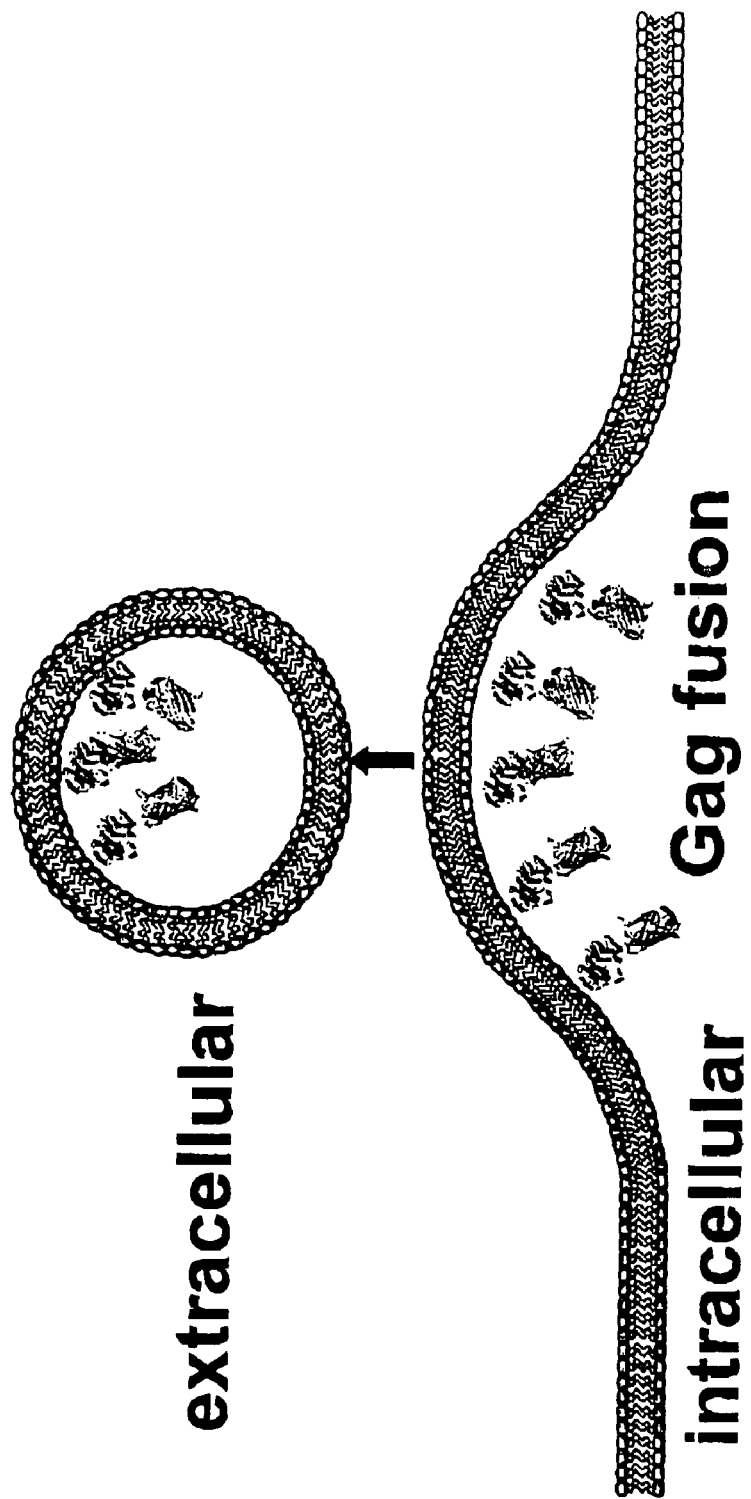

FIG. 2 shows a diagrammatic representation of the principle of VLP encapsulation of target molecules (non-membrane associated). The specificity of the incorporation of the respective target protein within the capsid of the VLPs is the result of either strong specific interaction of a molecular peptide tag covalently attached to the C-terminus of the signal protein (Gag) with a complementary specific peptide tag associated with the target of Interest or by direct covalent fusion of the Gag protein with the target protein/peptide of interest. The Gag-tag fusion protein is co-expressed in a cellular system with the respective molecule of interest which also carries a specific peptide tag either within the molecule or at either the N- or C-terminus. Expression of the modified Gag protein in the respective host cells results in the accumulation of the Gag protein at the plasma membrane due to signals present within the N-terminal portion of the Gag protein. High concentrations of this protein at the plasma membrane results in a budding process in which VLPs are released into the extracellular milieu. If the target protein carrying the complementary tag is expressed in the same cell and is concentrated in the intracellular compartments then the specific interaction with the tagged Gag protein results in the co-transport of the target to the plasma membrane and subsequent incorporation into the released VLPs.

Figure 3:
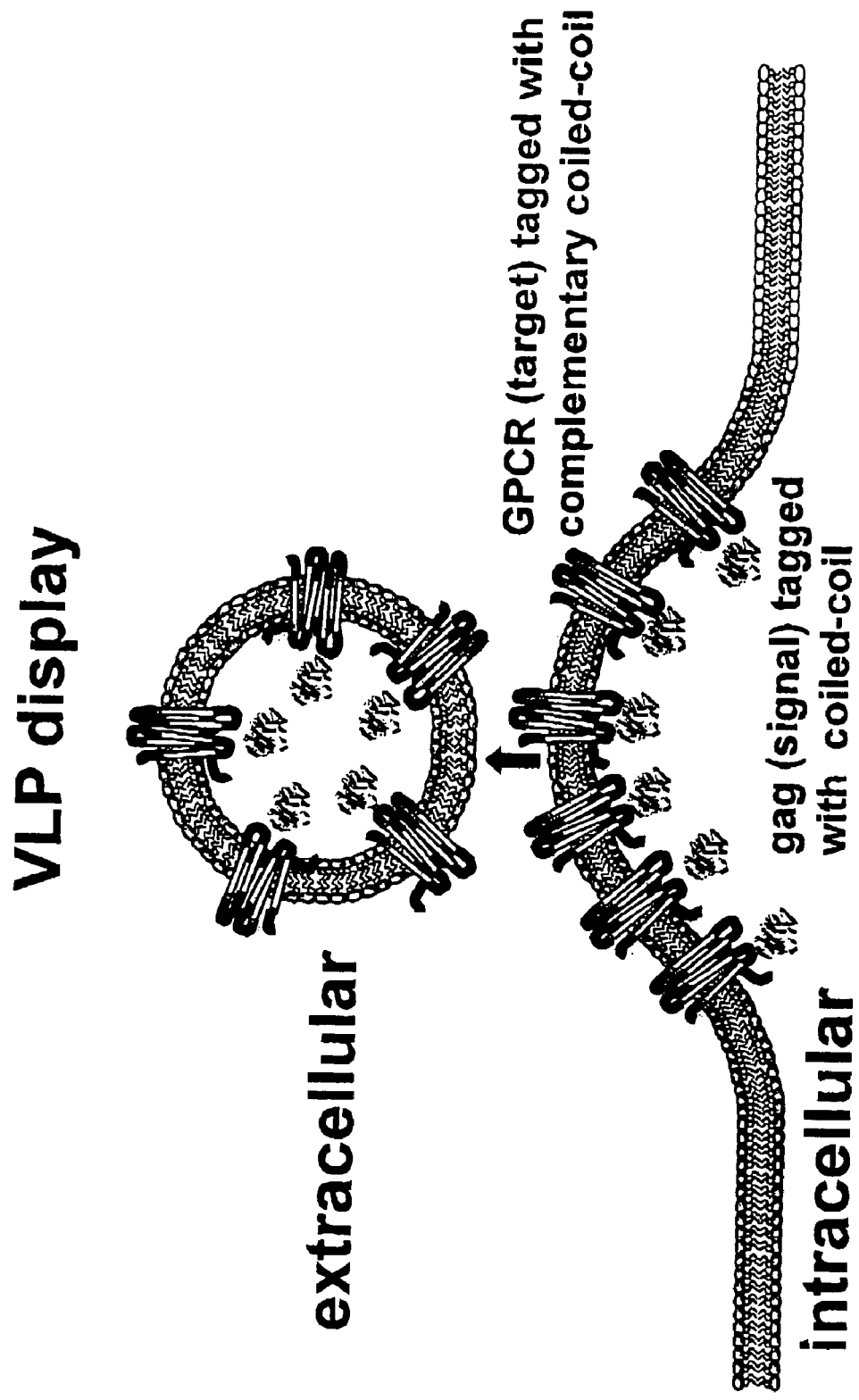

FIG. 3 depicts a diagrammatic representation of the principle of VLP display for target molecules associated with the plasma membrane (in this case G-protein coupled receptors). The specificity of the incorporation of the respective target protein within the envelope of the VLPs is the result of either a strong specific interaction of a molecular peptide tag covalently attached to the C-terminus of the signal protein (Gag) with a complementary specific peptide tag associated with the target of interest or by direct covalent fusion of the Gag protein with the target protein/peptide of interest. The Gag-tag fusion protein is co-expressed in a cellular system with the respective molecule of interest which also carries a specific peptide tag either within the molecule or at either the N- or C-terminus. Expression of the modified Gag protein in the respective host cells results in the accumulation of the Gag protein at the plasma membrane due to signals present within the N-terminal portion of the Gag protein. High concentrations of this protein at the plasma membrane results in a budding process in which VLPs are released into the extracellular milieu. If the target protein carrying the complementary tag is expressed in the same cell and is concentrated either in the intracellular compartments of the cell or preferably at high concentration in the plasma membrane then the specific interaction with the tagged Gag protein results in the subsequent incorporation into the released VLPs.

Figure 4:
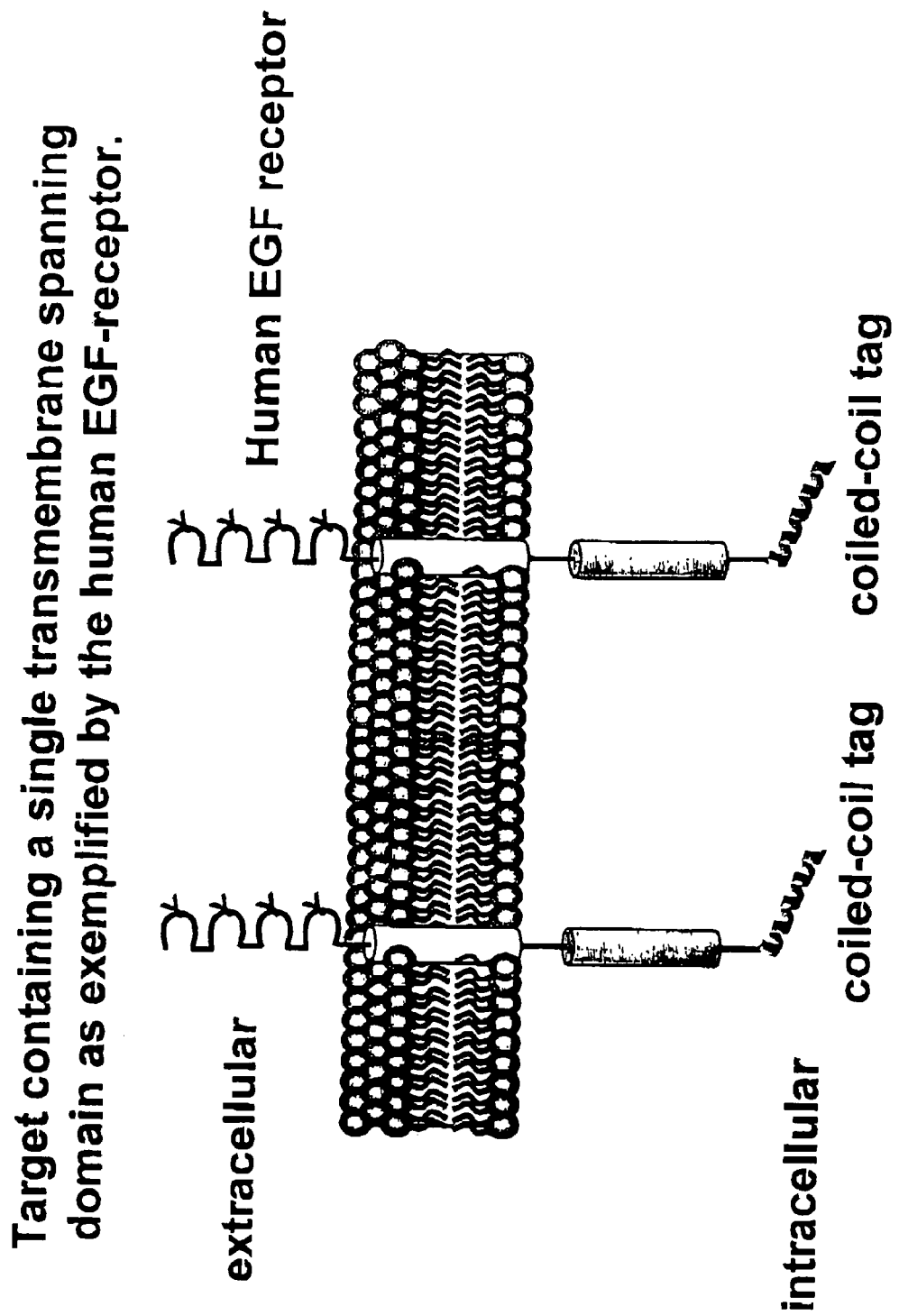
Figure 5:
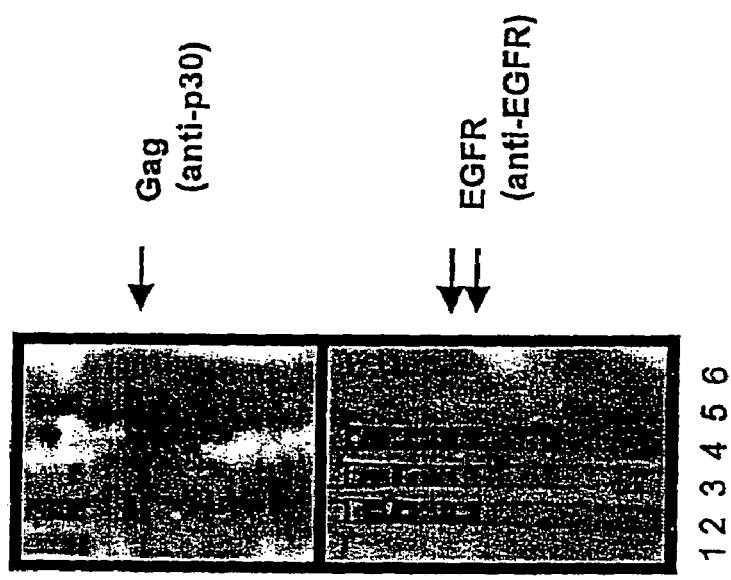
Figure 6:
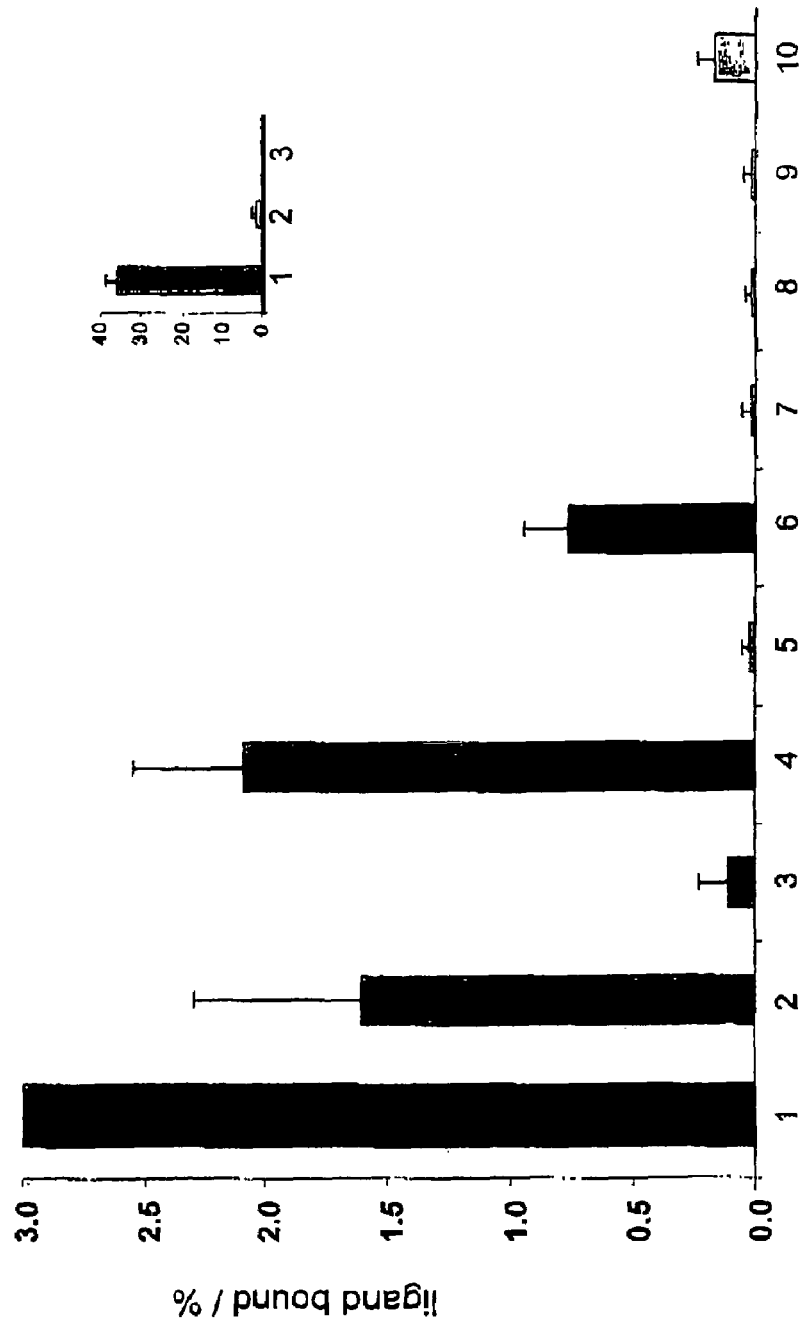
Figure 7:
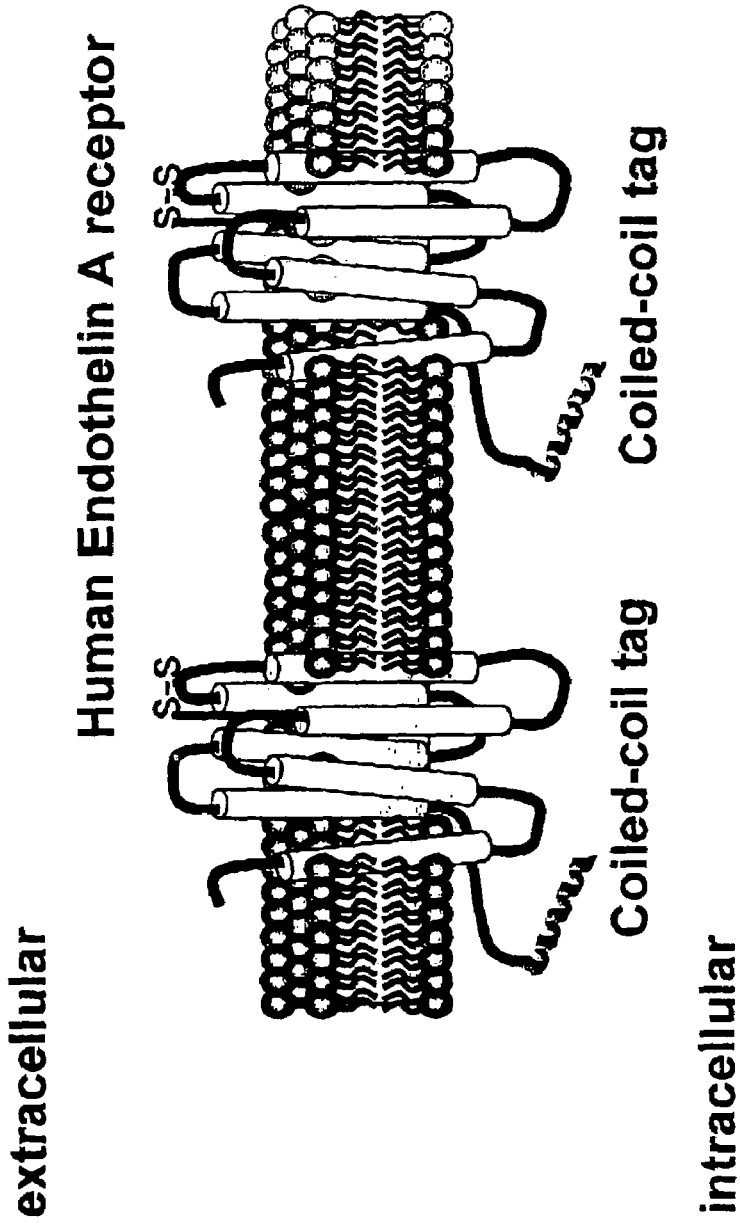

FIG. 4 shows the principle of VLP display for a membrane inserted protein containing a single transmembrane spanning domain as exemplified by the human epidermal growth factor (EGF) receptor (EGFR). The model system uses a target molecule containing a single transmembrane spanning segment and in particular the human EGF receptor which has been modified to express a specific coiled coil sequence at the carboxyl terminus of the protein, in this case the K-coil. Co-expression of a K-coil tagged EGF receptor (target) with E-coil tagged Gag (signal) in host cells would result in the release of VLPs containing the human EGF receptor integrated in the membrane envelope of the respective particles.

FIG. 5 depicts a Western blot analysis of the human EGF-receptor (EGFR) expressed on the surface of VLPs released from host cells co-expressing the tagged signal and target molecules. In this experiment Sf9 cells were infected for 48 hours with recombinant virus expressing the signal Gag-E-coil protein and/or the target EGFR-K-coil protein. A constant quantity of virus for the target (EGFR) was used throughout the whole experiment (m.o.i 10) and different amounts of signal Gag virus were used to co-infect the cells (m.o.i. 10-0.1). The cell culture supernatants were harvested and the VLPs were pelleted at 100 000 g for 30 minutes at 4° C. The resulting pellet was resuspended in PBS and an aliquot was separated on SDS PAGE and blotted. The resulting blots were probed with antibodies directed against the signal (Gag, upper panel) and the target (EGFR, lower panel). The results demonstrate the co-segregation of Gag and EGFR in the released VLPs.

Lane #1. EGFR-Kcoil virus m.o.i. 10.
Gag-Ecoil virus m.o.i. 10.
Lane #2. EGFR-Kcoil virus m.o.i. 10.
Gag-Ecoil virus m.o.i. 5.
Lane #3. EGFR-Kcoil virus m.o.i. 10.
Gag-Ecoil virus m.o.i. 1.
Lane #4. EGFR-Kcoil virus m.o.i. 10.
Gag-Ecoil virus m.o.i. 0.1.
Lane #5. Gag-Ecoil virus m.o.i. 10.
Lane #6. EGFR-Kcoil virus m.o.i. 10.

FIG. 6 shows a receptor binding analysis of the human EGF-receptor expressed on membrane vesicles and on the surface of VLPs released from host cells co-expressing the tagged signal and target molecules. In this experiment Sf9 cells were infected for 48 hours with recombinant virus expressing the signal Gag-E-coil protein and/or the target EGFR-K-coil protein. A constant quantity of virus for the target (EGFR) was used throughout the whole experiment (m.o.i. 10) and different amounts of signal Gag virus were used to co-infect the cells (m.o.i. 10-0.1), The cell culture supernatants were harvested and the VLPs were pelleted at 100 000 g for 30 minutes at 4° C. The resulting pellet was resuspended in PBS and an aliquot was analysed for the binding of TAMRA-labelled EGF. The ligand TAMRA-labelled EGF (L) was incubated with vesicles (V) prepared from A431 cells or with VLPs derived from Sf9 cells co-expressing Gag-E-coil and the EGF receptor tagged with K-coil in the presence or absence of 1 μM EGF (C). Fluorescent ligand bound to vesicles or VLPs was analysed by FIDA (for details see materials and methods). The results demonstrate the expression of functional EGF receptor molecules on the surface of the released VLPs. The insert demonstrates the results of the EGFR binding assay using the vesicle preparation from the A431 cells as shown in 1-3 in this diagram but expressed on a different scale for % of bound ligand.

1: L+V
2: L+C+V
3 L
4: L+VLP (compare FIG. 5, lane 2)
5: L+C+VLP (compare FIG. 5, lane 2)
6: L+VLP (compare FIG. 5, lane 4)
7: L+C+VLP (compare FIG. 5, lane 4)
8: L+VLP (compare FIG. 5, lane 5)
9: L+C+VLP (compare FIG. 5, lane 5)
10: L (see #3)

FIG. 7 depicts a VLP display strategy for a membrane inserted protein containing multiple transmembrane spanning domains as exemplified by the human Endothelin A receptor. The model system uses a target molecule containing multiple transmembrane spanning segments and in particular the human Endothelin A receptor ($ET_A$ receptor) as a member of the G-protein coupled receptor family (GPCR) which has been modified to express a specific coiled coil sequence at the carboxyl terminus of the protein, in this case the E-coil. Co-expression of a E-coil tagged $ET_A$ receptor (target) with K-coil tagged Gag (signal) in host cells would result in the release of VLPs containing the human $ET_A$ receptor integrated in the membrane envelope of the respective particles.

FIG. 8 shows a Western blot analysis of the human Endothelin A receptor expressed on the surface of VLPs released from host cells co-expressing the tagged signal and target molecules. In this experiment Sf9 cells were infected for 48 hours with recombinant virus expressing the signal Gag-K-coil protein and/or the target $ET_A$ receptor E-coil protein. A constant quantity of virus for the target ($ET_A$ receptor) was used throughout the whole experiment (m.o.i. 10) and different amounts of signal Gag virus were used to co-infect the cells (m.o.i. 10-0.1). The cell culture supernatants were harvested and the VLPs were pelleted at 100 000 G for 30 minutes at 4° C. The resulting pellet was resuspended in PBS and an aliquot was separated on SDS PAGE and blotted. The resulting blots were probed with antibodies directed against the signal (Gag, lower panel) and the target ($ET_A$ receptor, upper panel). The results demonstrate the co-segregation of Gag and $ET_A$ receptor in the released VLPs.

Lane #1. $ET_A$ Receptor-Ecoil (clone #18) virus m.o.i. 10.
Gag-Kcoil virus m.o.i. 10.
Lane #2. $ET_A$ Receptor-Ecoil (clone #18) virus m.o.i. 10.
Gag-Kcoil virus m.o.i. 5.
Lane #3. $ET_A$ Receptor-Ecoil (clone #18) virus m.o.i. 10.
Gag-Kcoil virus m.o.i. 1.
Lane #4. $ET_A$ Receptor-Ecoil (done #18) virus m.o.i. 10.
Gag-Kcoil virus m.o.i. 0.1.
Lane #5. Gag-Kcoil virus m.o.i. 10.
Lane #6. $ET_A$ Receptor-Ecoil (clone #18) virus m.o.i. 10.
Lane #7. $ET_A$ Receptor-Ecoil (clone #20) virus m.o.i. 10.
Gag-Kcoil virus m.o.i. 10.
Lane #8. $ET_A$ Receptor-Ecoil (clone #20) virus m.o.i. 10.
Gag-Kcoil virus m.o.i. 5.
Lane #9. $ET_A$ Receptor-Ecoil (clone #20) virus m.o.i. 10.
Gag-Kcoil virus m.o.i. 1.
Lane #10. $ET_A$ Receptor-Ecoil (clone #20) virus m.o.i. 10.
Gag-Kcoil virus m.o.i. 0.1.
Lane #11. Gag-Kcoil virus m.o.i. 10.
Lane #12. $ET_A$ Receptor-Ecoil (clone #20) virus m.o.i. 10.

FIG. 9 shows a receptor binding analysis of the human $ET_A$ expressed on membrane vesicles and on the surface of VLPs released from host cells co-expressing the tagged signal and target molecules. In this experiment Sf9 cells were infected for 48 hours with recombinant virus expressing the signal Gag-K-coil protein and/or the target $ET_A$ receptor-E-coll protein. A constant quantity of virus for the target ($ET_A$ receptor) was used throughout the whole experiment (m.o.i. 10) and different amounts of signal Gag virus were used to co-infect the cells (m.o.i. 10-0.1). The cell culture supernatants were harvested and the VLPs were pelleted at 100 000 g for 30 minutes at 4° C. The resulting pellet was re-suspended in PBS and an aliquot was analysed for the binding of TAMRA-labeled endothelin-1. Ligand TAMRA labelled Endothelin-1 (L) was incubated with vesicles (V) prepared from recombinant CHO cells expressing the $ET_A$ receptor or with VLPs derived from Sf9 cells co-expressing Gag-K-coil and the $ET_A$ receptor tagged with Flag and E-coil in the presence or absence of 1 µM endothelin-1 (C). Fluorescent ligand bound to vesicles or VLPs was analysed by FIDA (for details see materials and methods). The insert demonstrates the vesicle based binding analysis represented on a different scale with respect to the percentage of bound ligand. The data corresponds to samples 1-3 on the large diagram. The results demonstrate the expression of functional $ET_A$ receptor molecules on the surface of the released VLPs.

Figure 8:
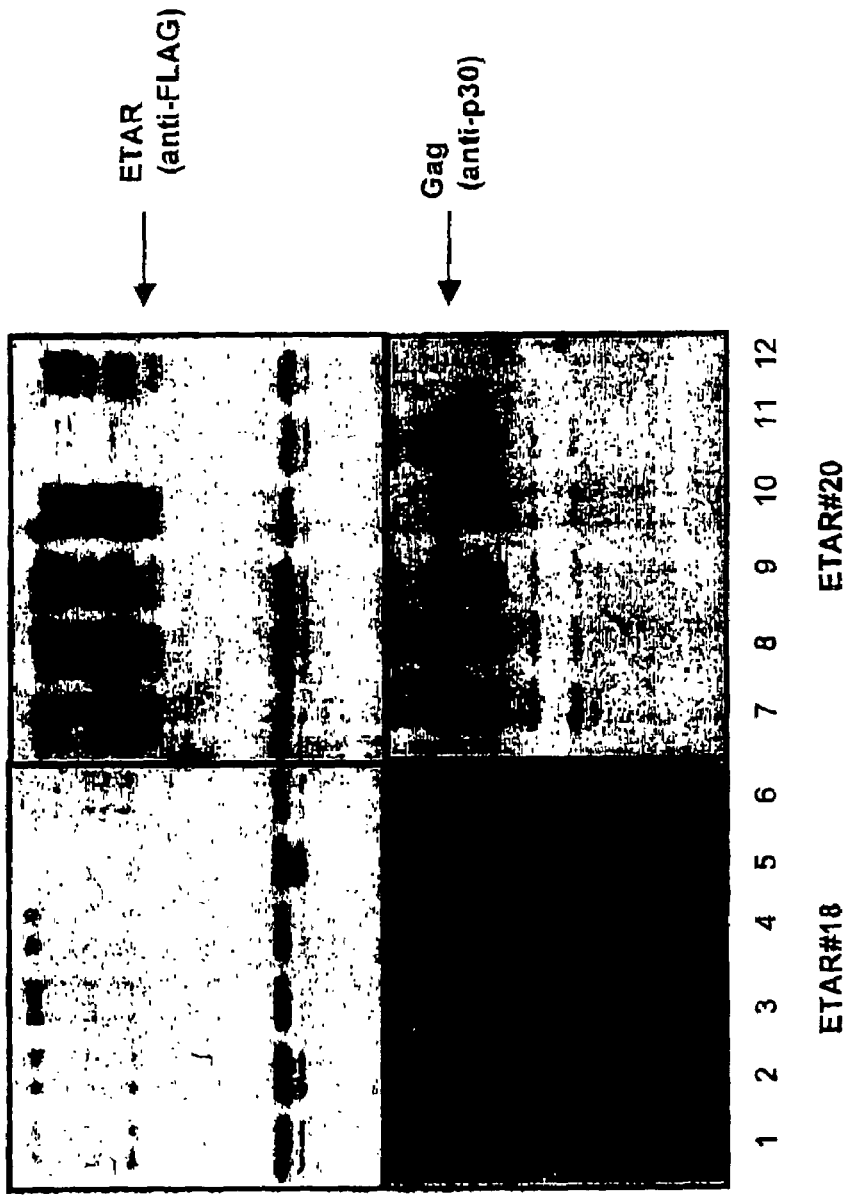

1: L+V
2: L+C+V
3 L
4, L+VLP (compare FIG. 8, lane 1)
5: L+C+VLP (compare FIG. 8, lane 1)
6: L+VLP (compare FIG. 8, lane 2)
7: L+C+VLP (compare FIG. 8, lane 2)
8: L+VLP (compare FIG. 8, lane 5)
9; L+C+VLP (compare FIG. 8, lane 5)

Figure 10:
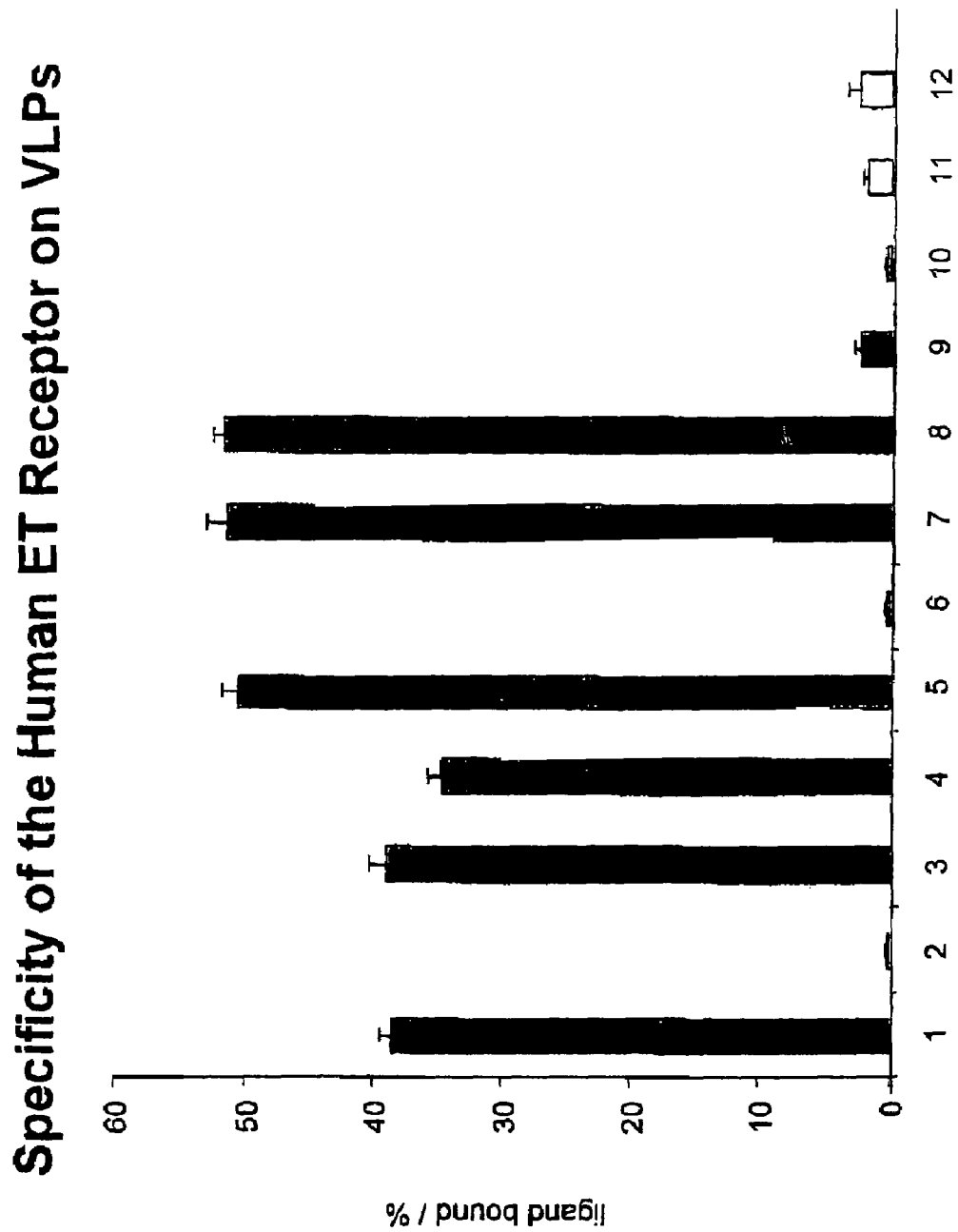

FIG. 10 depicts the specificity of the human $ET_A$ receptor on membrane vesicles and VLPs. TAMRA-labelled endothelin-1 (L) was incubated with VLPs derived from Sf9 cells co-expressing Gag-K-coil and the $ET_A$ receptor tagged with E-coil in the presence or absence of 1 µM endothelin-1 (Er-1) or big endothelin-1 (Big ET-1) or somatostatin-14 (SRIF-14). Fluorescent ligand bound to vesicles or VLPs was analysed by FIDA (for details see materials and methods).

1: L+VLP (compare FIG. 8, lane 1)
2: L+ET-1+VLP (compare FIG. 8, lane 1)
3: L+Big ET-1+VLP (compare FIG. 8, lane 1)
4: L+SRIF-14+VLP (compare FIG. 8, lane 1)
5: L+VLP (compare FIG. 8, lane 2)
6: L+ET-1+VLP (compare FIG. 8, lane 2)
7: L+Big ET-1+VLP (compare FIG. 8, lane 2)
8: L+SRIF-14+VLP (compare FIG. 8, lane 2)
9: L+VLP (compare FIG. 8, lane 5)
10: L+ET-1+VLP (compare FIG. 8, lane 5)
11: L+Big ET-1+VLP (compare FIG. 8, lane 5)
12: L+SRIF-14+VLP (compare FIG. 8, lane 5)

Figure 11:
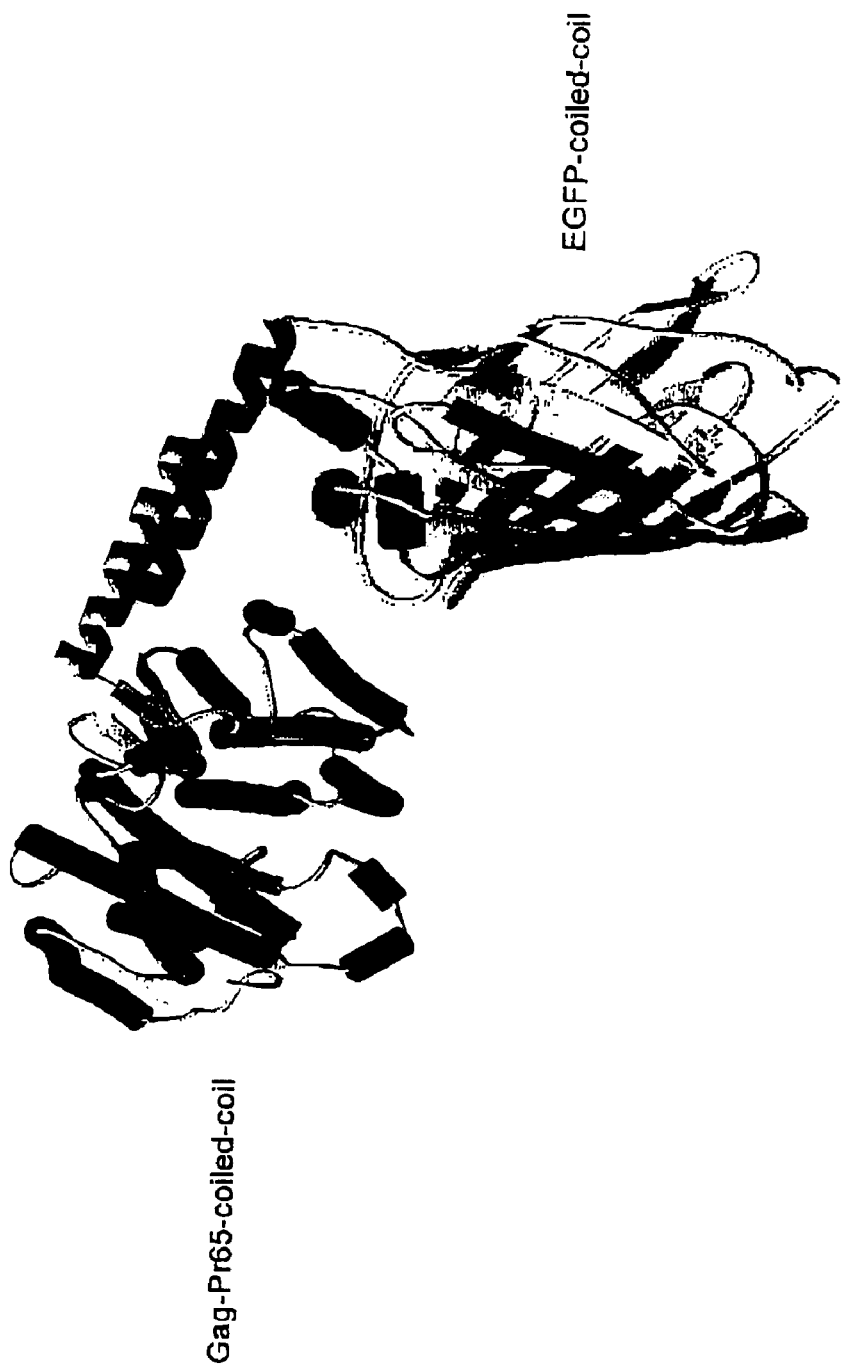

FIG. 11 shows the VLP encapsulation of non-membrane associated target for proteins found within the cytoplasm as exemplified by the EGFP molecule (Enhanced GFP molecule). The model system uses a target molecule which is found as a soluble molecule in the cytoplasm of cells and is not naturally associated with membranes, in particular the EGFP molecule which has been modified to express a specific coiled coil sequence at the carboxyl terminus of the protein, in this case the E-coil, Co-expression of a E-coil tagged EGFP (target) with K-coil tagged Gag (signal) in host cells would result in the release of VLPs containing the EGFP molecule encapsulated within the capsid structure of the respective particles.

Figure 12:
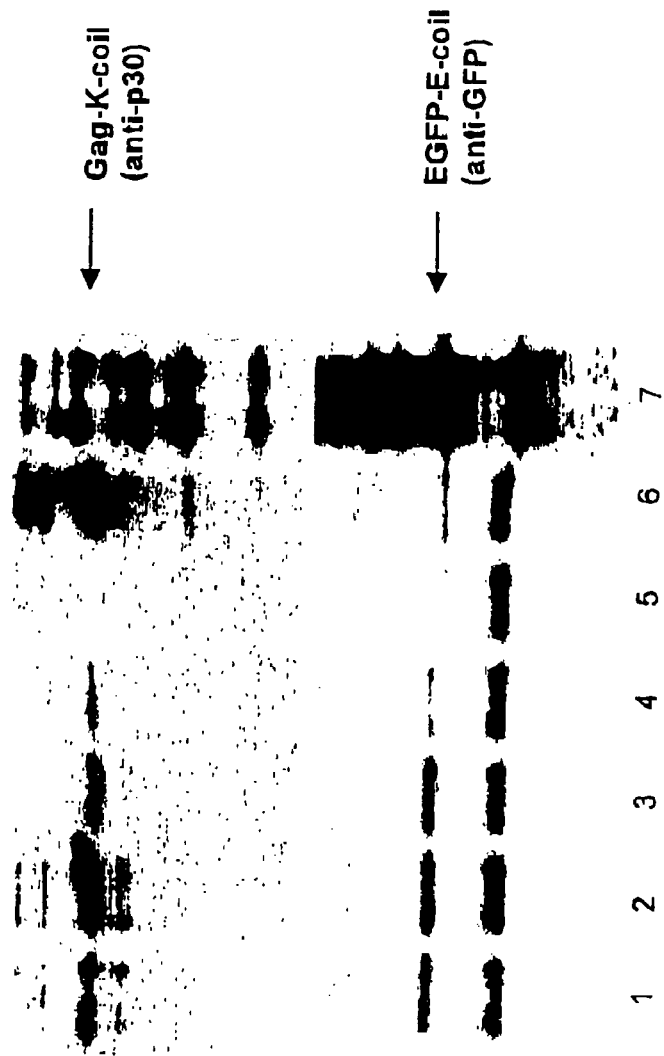

FIG. 12 shows a Western blot analysis of EGFP expressed within the capsid of VLPs released from host cells co-expressing the tagged signal and target molecules. In this experiment Sf9 cells were infected for 48 hours with recombinant virus expressing the signal Gag-K-coil protein and/or the target EGFP E-coil protein. A constant quantity of virus for the target (EGFP) was used throughout the whole experiment (m.o.i. 10) and different amounts of signal Gag virus were used to co-infect the cells (m.o.i. 10-0.1). The cell culture supernatants were harvested and the VLPs were pelleted at 100 000 g for 30 minutes at 4° C. The resulting pellet was re-suspended in PBS and an aliquot was separated on SDS PAGE and blotted. The resulting blots were probed with antibodies directed against the signal (Gag) and the target (EGFP). The results demonstrate the co-segregation of Gag and EGFP in the released VLPs.

Lane #1. EGFP-Ecoil virus m.o.i. 10.
   Gag-Kcoil virus m.o.i. 10.
Lane #2. EGFP-Ecoil virus m.o.i. 10.
   Gag-Kcoil virus m.o.i. 5.
Lane #3. EGFP-Ecoil virus m.o.i. 10.
   Gag-Kcoil virus m.o.i. 2.5.
Lane #4. EGFP-Ecoil virus m.o.i. 10.
   Gag-Kcoil virus m.o.i. 1.
Lane #5. EGFP-Ecoil virus m.o.i. 10.
   Gag-Kcoil virus m.o.i. 0.1.
Lane #6. EGFP-Ecoil virus m.o.i. 10.
Lane #7. Gag-Kcoil virus m.o.i. 10.

Figure 13:
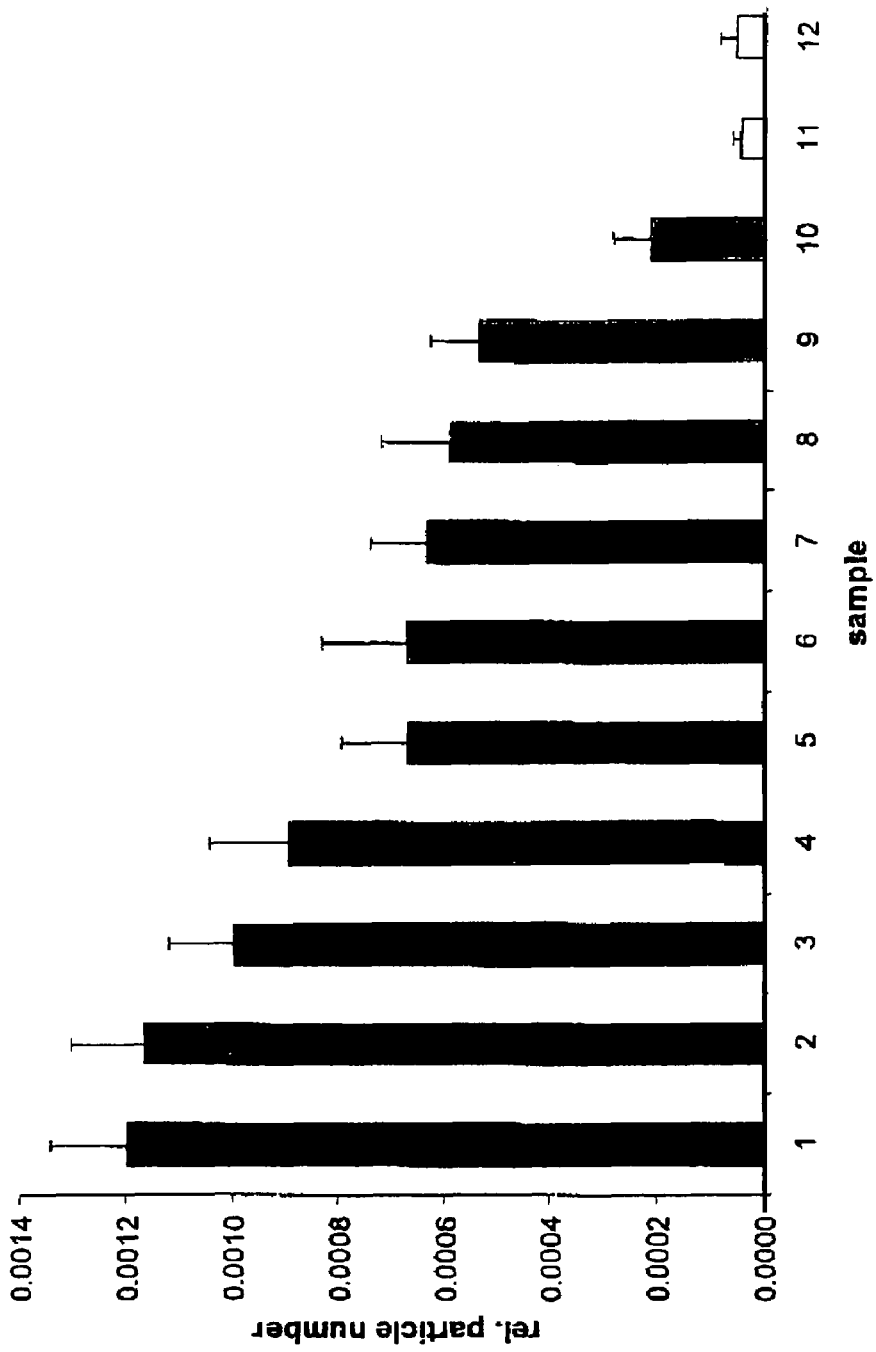

FIG. 13 depicts FIDA detection and quantitative analysis of fluorescent VLPs released from host cells co-expressing the tagged signal and target molecules. In this experiment Sf9 cells were infected for 48 hours with recombinant virus expressing the signal Gag-K-coil protein and/or the target EGFP-E-coil protein. A constant quantity of virus for the target (EGFP) was used throughout the whole experiment (m.o.i. 10) and different amounts of signal Gag virus were used to co-infect the cells (m.o.i. 10-0.1). The cell culture supernatants were harvested filtered (0.45 µM) and the VLPs were pelleted at 100 000 g for 30 minutes at 4° C. The resulting pellet was re-suspended in PBS and the mixture was analysed by FIDA (for details see materials and methods). The VLP preparations were diluted with the medium from which they had been pelleted (VLP supernatant). A relative particle number was determined corresponding to the VLP particle number in suspension.

Figure 14:
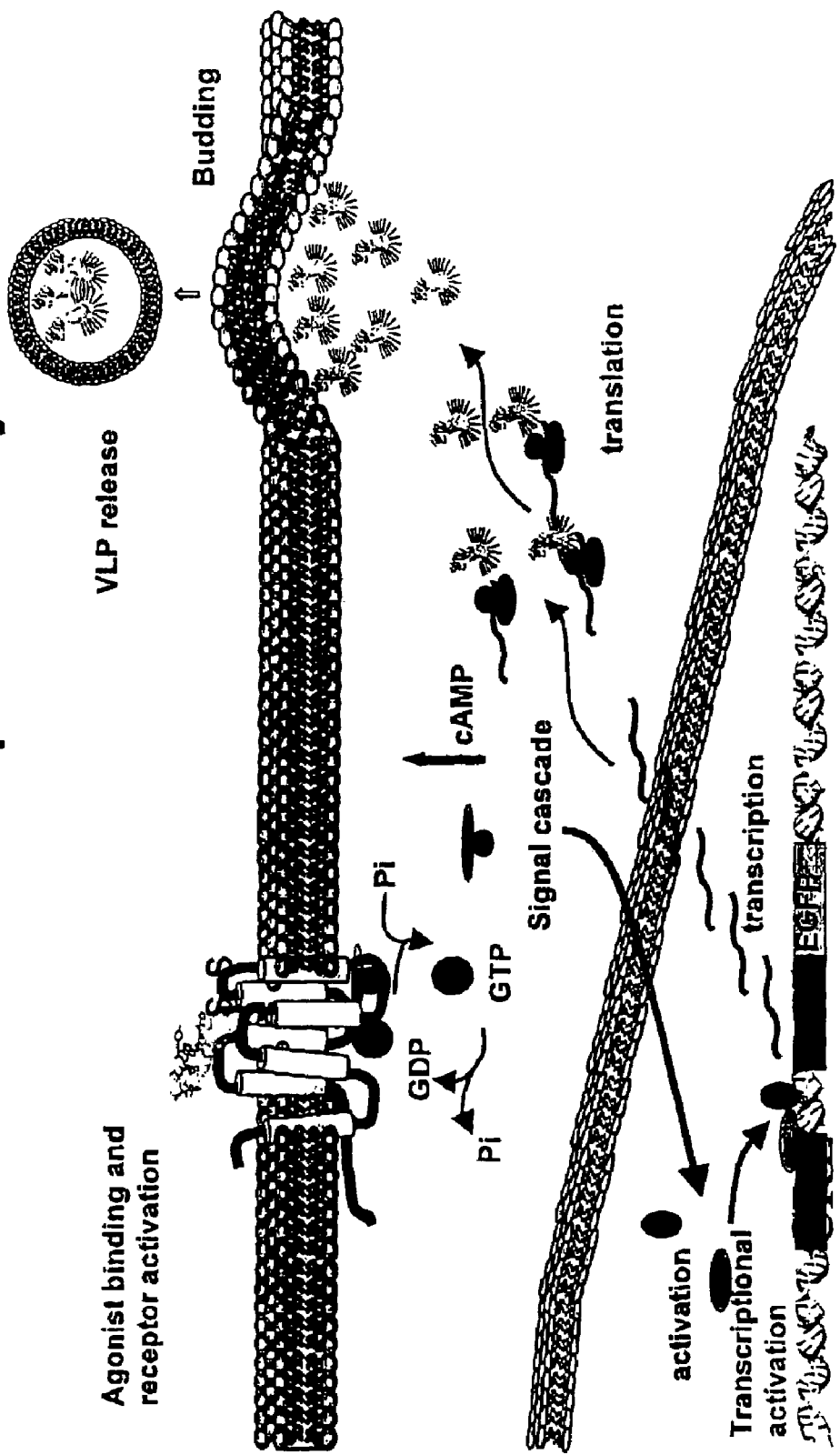

1: undiluted VLP suspension
2: 9 vol. VLP suspension+1 vol. VLP supernatant
3: 8 vol. VLP suspension+2 vol. VLP supernatant
4: 7 vol. VLP suspension+3 vol. VLP supernatant
5: 6 vol. VLP suspension+4 vol. VLP supernatant
6: 5 vol. VLP suspension+5 vol. VLP supernatant
7: 4 vol. VLP suspension+6 vol. VLP supernatant
8: 3 vol. VLP suspension+7 vol. VLP supernatant
9: 2 vol. VLP suspension+8 vol. VLP supernatant
10; 1 vol. VLP suspension+9 vol. VLP supernatant
11: VLP supernatant
12: sterile cell culture medium FIG. 14 shows the principle of a VLP based reporter assays for the detection of agonist induced stimulation of a membrane based receptor. Stimulation of a membrane bound receptor or ion channel (in the diagram a GPCR) results in the stimulation of a second messenger system which subsequently transfers this stimulative information to the cell nucleus. Transcription factors are activated and bind to specific DNA sequences (responsive elements) and transcriptional activation of the respective reporter gene which has been engineered to be under control of this responsive element is then initiated. The translation product of the reporter gene, in this case a Gag-EGFP fusion protein then accumulates within the cell and subsequently at the membrane surface of the cell. Concentration of the Gag-EGFP fusion at the plasma membrane induces the formation and release of VLPs into the extracellular medium where they can be harvested and subsequently quantified or where they can be detected directly, e.g. by confocal microscopy/spectroscopy.

Figure 15:
Figure 15:

FIG. 15 demonstrates the effect of Forskolin induced accumulation of intracellular CAMP that results in the synthesis of the Gag fusion reporter gene product. CHO cells stabely transfected with a construct consisting of a CAMP responsive element in conjunction with a thymidine kinase basal promoter (without an enhancer) regulating the transcription of the reporter gene fusion were cultured either in the presence or absence of 2 μforskolin for 24 hours before being analysed by fluorescence microscopy. The top row of each panel represents the fluorescence detectable in the cells whereas the bottom row in each panel represents the illuminated field analysed by fluorescence. Each of the panels represents a representative view from a number of independent cultures analysed.

Figure 16:
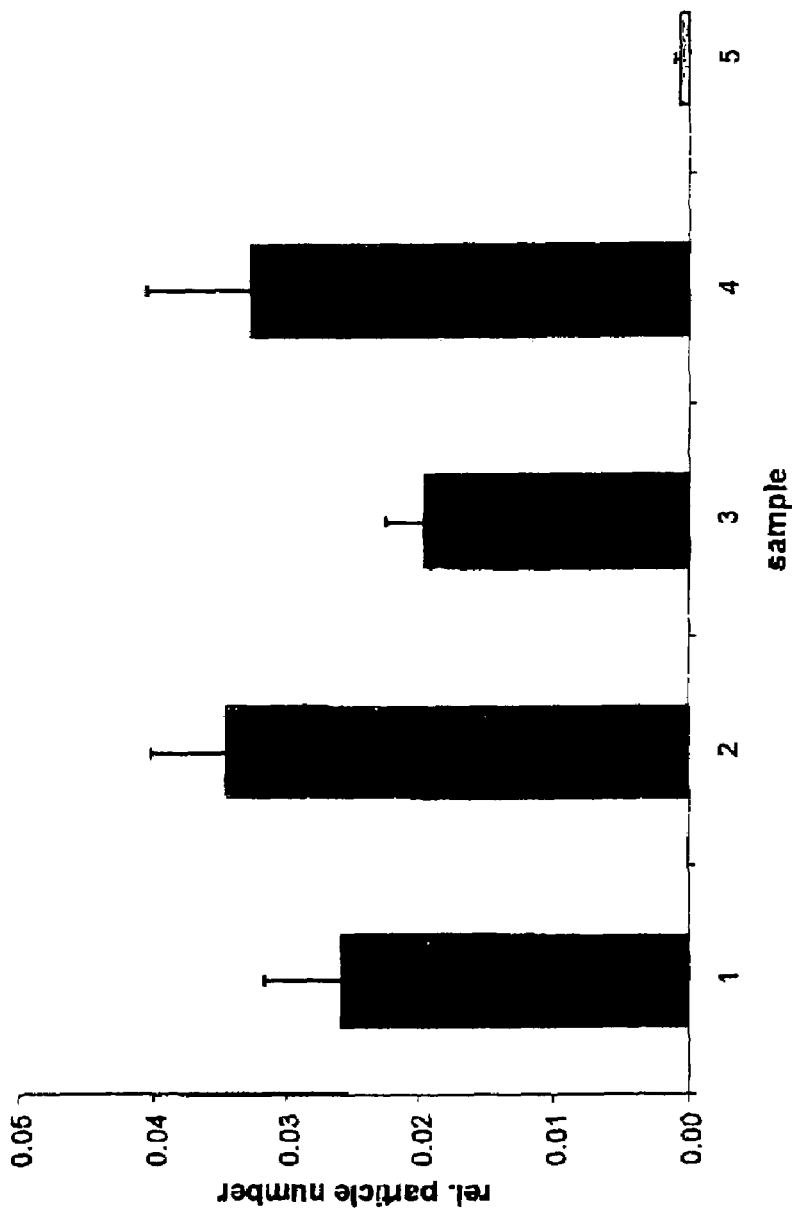
Figure 17:
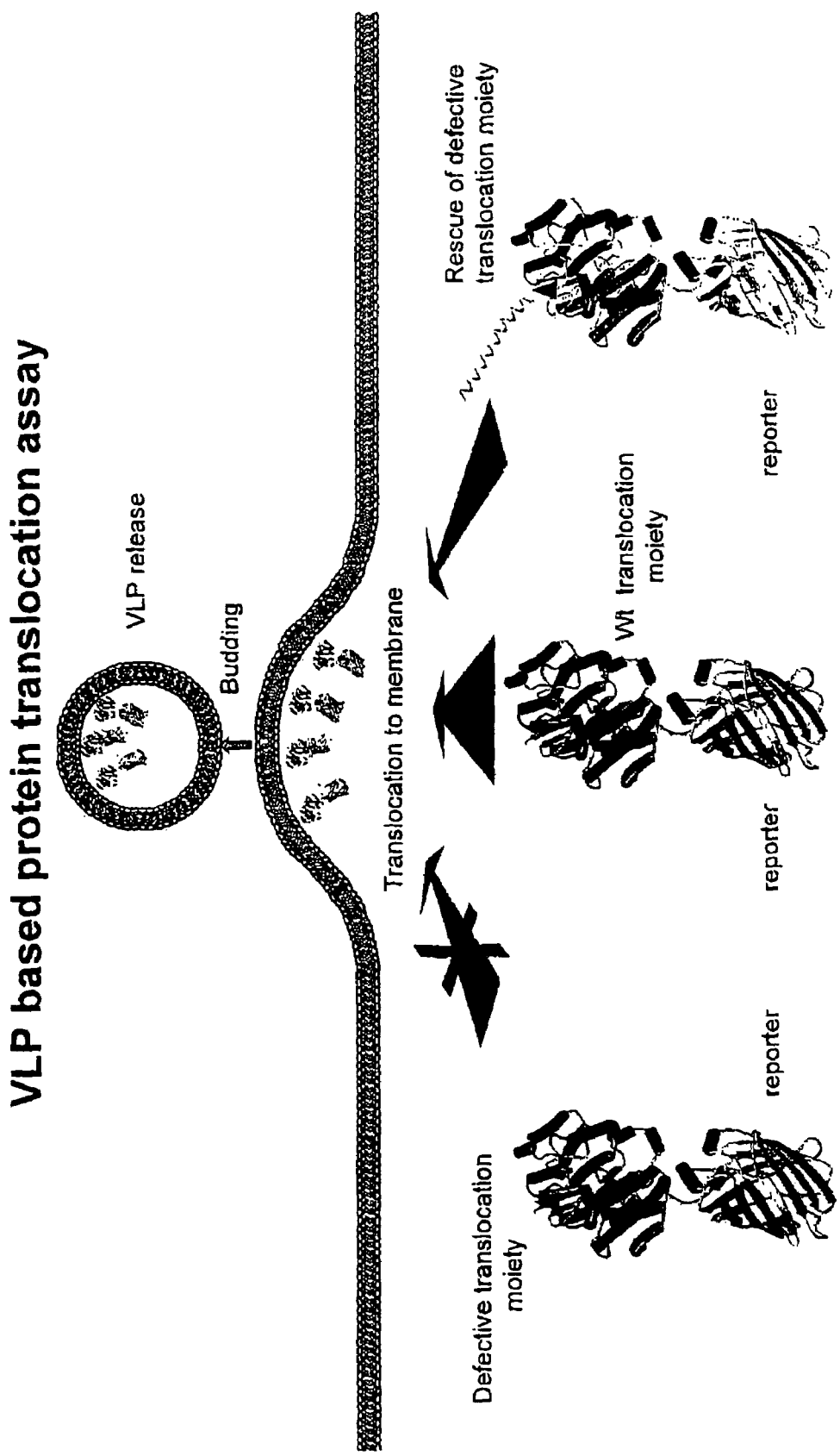

FIG. 16 depicts the FIDA analysis of the Gag-EGFP reporter assay demonstrated above. CHO cells stabely transfected with a construct consisting of a CAMP responsive element in conjunction with a thymidine kinase basal promoter (without an enhancer) regulating the transcription of the reporter gene fusion were cultured either in the presence or absence of 2 μM forskolin for 48, hours. Cell culture supernatants were filtered (0.45 μm) and analysed by FIDA (for details see materials and methods). A relative particle number was determined corresponding to the VLP particle number released into the culture medium.
1: non-induced
2: induced with 2 μM forskolin
3: non-induced
4: induced with 2 μM forskolin
5: sterile cell culture medium FIG. 17 demonstrates the principle of the VLP based translocation assay. The figure describes the principle of the assay which can be utilised to identify sequences from a plurality of sequences (cDNA library) which are capable of translocating a defective signal sequence which is normally able to potentiate the formation and release of VLPs into the cell culture medium. In the primary assay concept the defective signal molecule (e.g. Gag mutated at position two after the initiation codon) which is unable to target the signal molecule to the plasma membrane, is operationally associated either covalently or non-covalently to a reporter molecule (in the diagram a green fluorescent protein). This hybrid molecule when comprised of a functional signal molecule is able to translocate to the plasma membrane and VLPs are released into the extracellular environment where they can be measured and quantified by a number of detection methodologies. When the defective signal molecule comprising a reporter molecule hybrid is modified at its amino terminus by the addition of a specific translocation signal specific for secreted and membrane associated proteins then this translocation defect is alleviated and VLPs are released into the extracellular medium.

Figure 18:
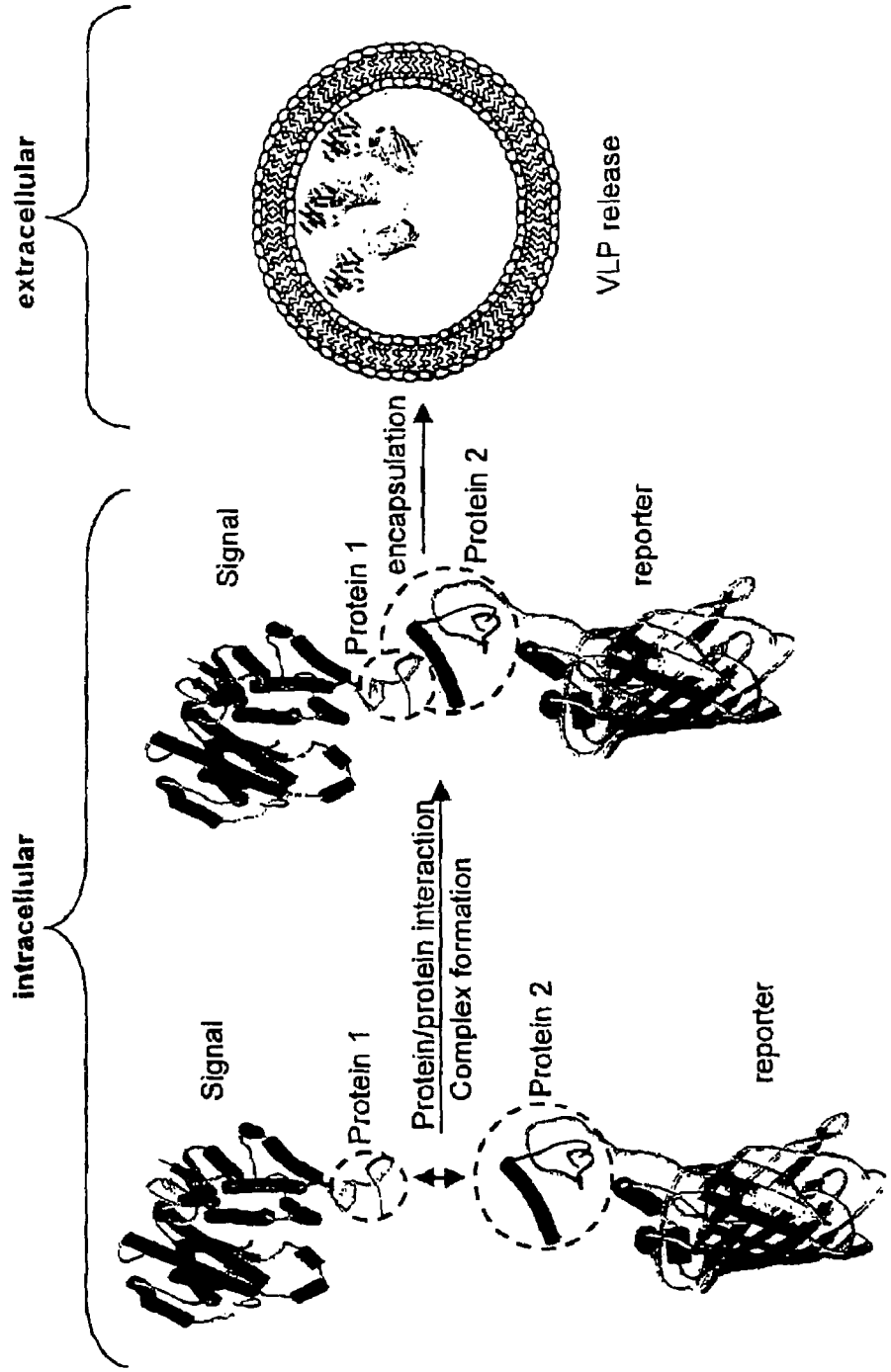

FIG. 18 depicts the principle of the VLP based protein-protein interaction assay. The diagram demonstrates the principle of this assay format in which protein-protein interactions occurring within cells can be monitored. In the first instance a functional signal molecule (Gag) capable of inducing the formation and the release of VLPs into the extracellular medium comprises—in either covalently or non-covalently manner—the first partner of the protein-protein interaction of interest. In the following instance the second partner of the protein-protein interaction of interest is fused/attached either covalently or non-covalently to a reporter molecule, in particular and as depicted in the diagram a luminescent protein. If the first and the second partner interact then a complex including these molecules is formed which is then capable of forming VLPs structures resulting in their subsequent release into the extracellular environment where they can be detected and quantified by a number of methodologies. To further analyse the protein-protein interaction in situ, compounds under study are applied to the cells and if they are able to cross the plasma membrane and modify this interaction then the release of luminescent VLPs into the extracellular environment will be influenced and may be subsequently quantified.

Figure 19:
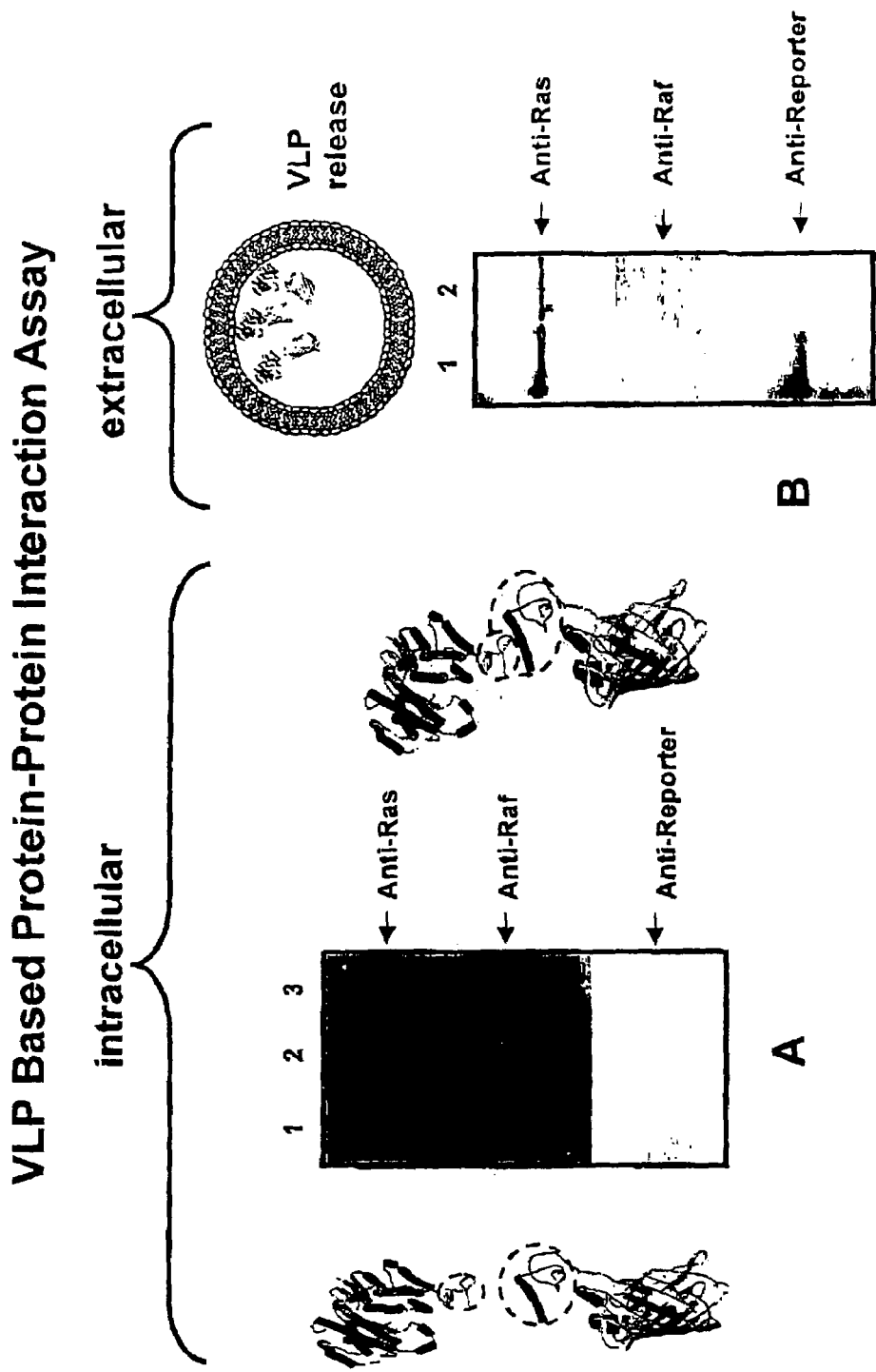

FIG. 19 shows a Western blot analysis of proteins expressed both intracellularly and proteins incorporated within VLPs released from host cells co-expressing signal and target-fusion molecules. In this experiment Sf9 cells were transiently transfected with constructs expressing either a Gag-Ras fusion, full length Raf or a Raf-EGFP fusion. 96 hours post transfection the cell culture supernatants were harvested and the VLPs were pelleted at 100 000 g for 30 minutes at 4° C. The transfected cells were washed once with PBS before being lysed in 50 mM Tris-HCl, 150 mM NaCl, 1% NP40, pH7.8 and protease inhibitors on ice for 20 minutes. The lysed cells were then centrifuged for 10 minutes at 10 000 g and the soluble protein fraction was then used for SDS PAGE analysis. Aliquots of either VLPs or the soluble protein lysates were resuspended in 2×SDS PAGE sample buffer (20 mM Tris-HcCl pH 6.8.2% SDS, 20 mM DTT, 2% βME, 10% glycerol) and boiled for 1 minute to denature the samples. Protein samples were then separated on 12% SDS PAGE gels according to standard molecular biological methods. The resulting blots were probed with antibodies directed against the Gag-Ras fusion (anti-Ras), the full length Raf (anti-Raf) and the Raf-EGFP fusion (anti-GFP). The results demonstrate the intracellular co-expression and co-segregation of Gag-Ras and either the full length Raf or the Raf-EGFP fusion in the released VLPs.

A: Protein Analysis in Sf9 Whole Cell Lysates.

Lane #1, Co-expression of full length Raf and Raf-EGFP

Lane #2. Co-expression of full length Raf, Raf-EGFP and Gag-Ras

Lane #3. Expression of Gag-Ras.

B: Protein Analysis of Pelleted VLP Released from Transfected Cells.

Lane #1. VLPs released from cells transfected with Gag-Ras and Raf-

Lane #5. VLPs released from cells transfected with Gag-Ras and full length Raf.

The results demonstrate that intracellularly all of the respective proteins are being expressed at detectable levels and are of the correct integrity. Furthermore VLPs released after co-expression of Gag-Ras and either the full length Raf or the Raf-EGFP fusion incorporate the Raf/reporter proteins as a result of protein protein interactions between the said Raf molecules and the Gag-Ras partner, thus demonstrating the principle.

Figure 20:
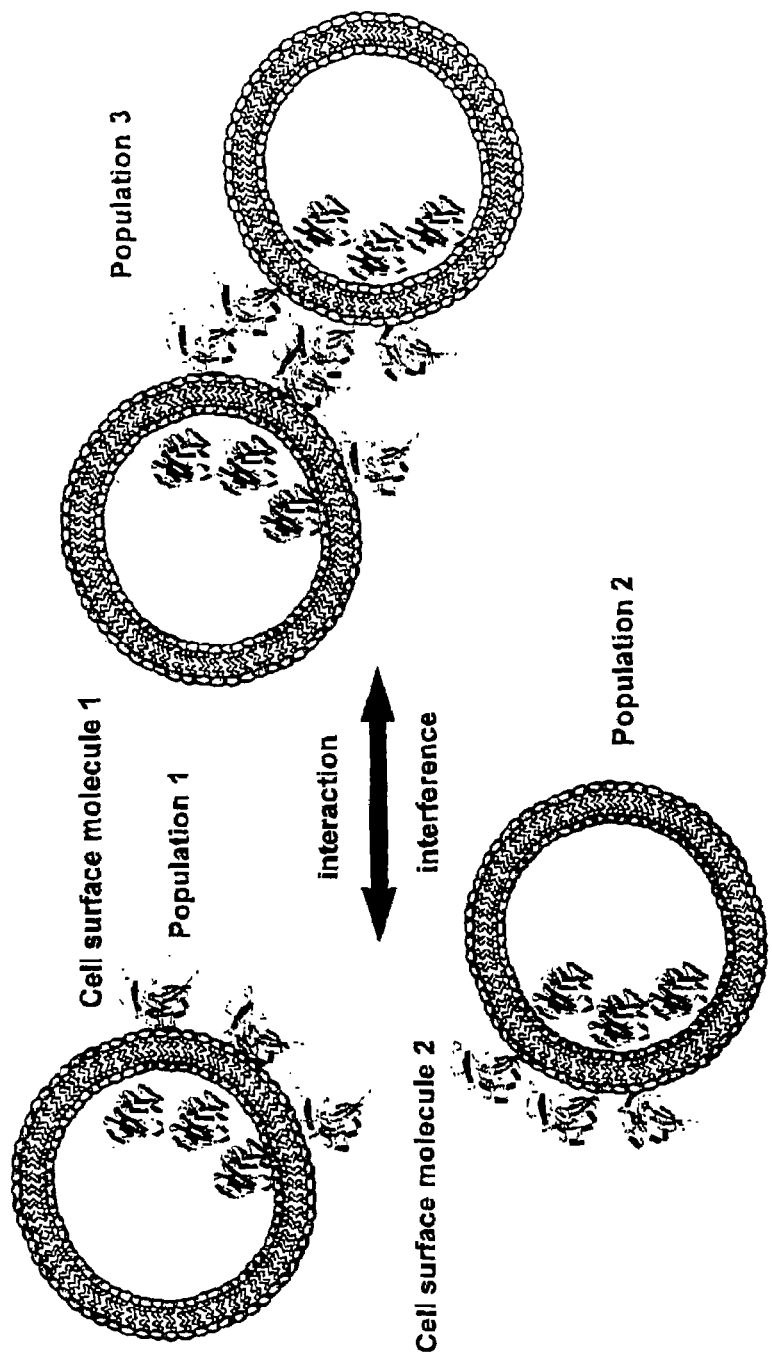

FIG. 20 demonstrates the principle of the VLP based cell-cell interaction assay. Homologous or heterologous interactions. The figure shows the principle underlining this assay format. The interactive cell surface molecules under study are attached to the surface of two different VLP populations, using the methodologies described above. The resulting two populations which carry the functional molecules of interest are then mixed in predefined ratios and allowed to interact. If the interaction is specific then aggregates will form which can be distinguished from non-aggregated VLP populations. Compounds which interfere with these target interactions are then added to the mixture and the dissociation of the aggregates as compared to controls is then quantified by a variety of methodologies resulting in an index of target-target inhibition.

Figure 21:
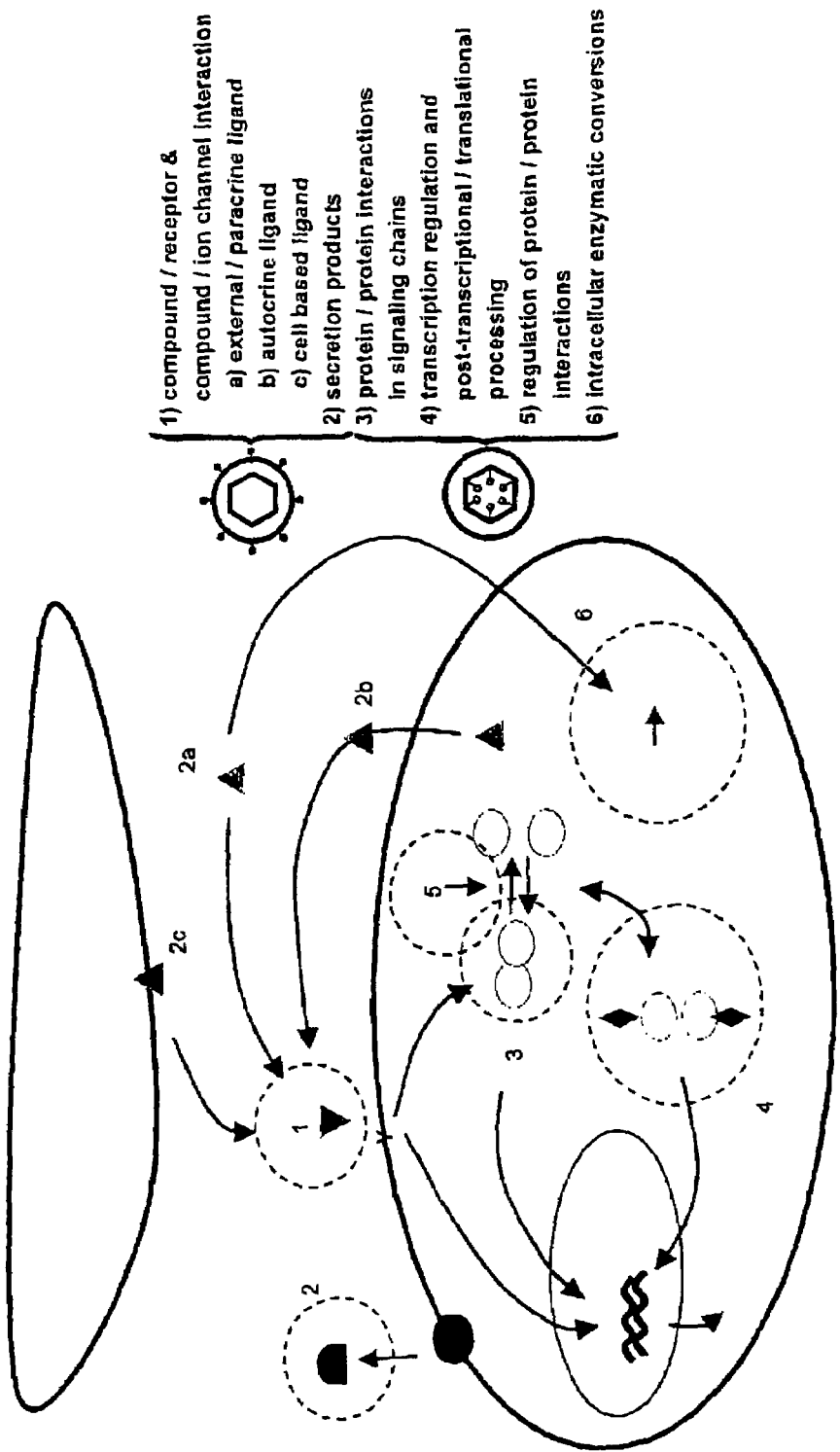

FIG. 21 depicts an overview of the VLP based assay technologies. Overview of the applications for the technologies described in the preceding assay formats. Assays described above or variants thereof are shown in this diagram and the respective VLP system utilised is also symbolised either by incorporation into the lipid envelope of the released VLP (1-3) or by encapsulation within the released VLP (4-6). Assay format 1 represents a cell surface—compound interaction (where the cell surface molecule can be a receptor or an ion channel and is the target) in which the target is incorporated in the lipid envelope membrane of the mature VLP, analogous to its normal location in the cell plasma membrane. The compounds may be represented as external molecules either of synthetic origin or of natural origin either obtained from cell/tissue extracts or molecules secreted from natural sources. Furthermore the release of such VLPs into the extracellular medium may also be mediated by the stimulation of either external compounds or by paracrine and or autocrine regulatory mechanisms. Cell-cell interactions as depicted in (2) can be analysed by utilising two independent VLP preparations carrying the cell surface molecules of interest (receptor-ligand, adhesion molecule Interaction both homologous and heterologous). The secretory pathway can also be analysed with a VLP based assay (2) in which the encapsulation of a target-signal fusion capable of rescuing a defective signal molecule results in the formation and release of detectable VLPs into the extracellular medium. Protein-protein interactions (3) form the basis of a further VLP based system in which the positive interaction of two known/unknown, polypeptides/peptide domains results in the co-localisation of a signal and a reporter molecule and the subsequent release of chimeric detectable VLPs into the extracellular medium. A further variation of this assay is the analysis of post-transcriptional/post-translational assays in which the protein-protein interaction is essential for efficient functioning (4-5). In a further assay format a signal-reporter fusion when under the control of a responsive DNA element e.g. CRE or ERE etc is synthesised in response to a signal influencing this element (elevation in transcription as compared to non-stimulated cells). Transcription and subsequent translation results in the formation (after encapsulation) and release of detectable VLPs (4). Finally encapsulation of active enzymes into VLPs results in a homogeneous preparation of membrane enveloped active protein whose activity can be determined towards compounds that are not only able to influence this activity but are also able to cross biological membrane barriers.

Figure 22:
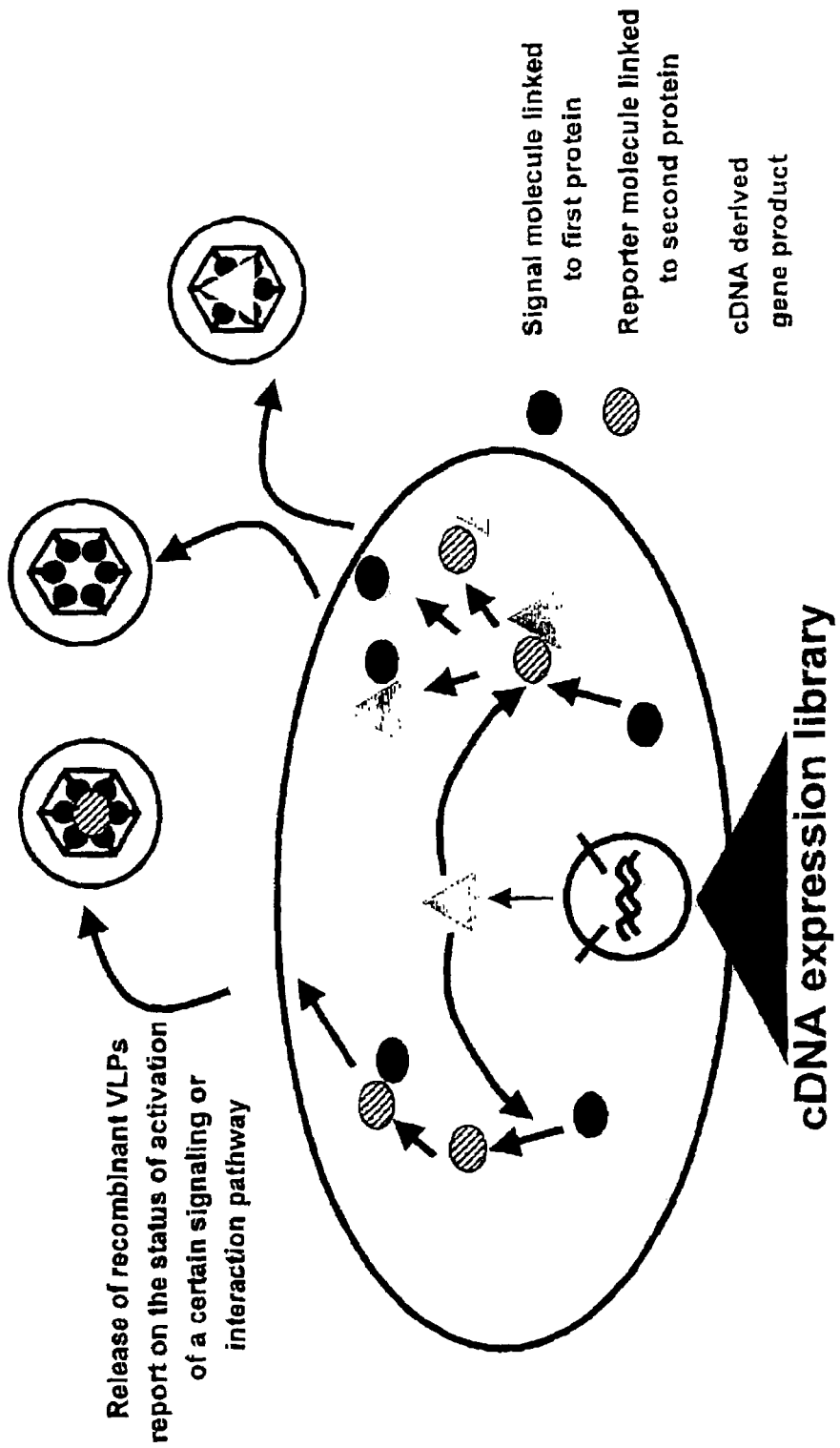

FIG. 22 depicts a preferred embodiment of the present invention. This assay regimen can be used for the identification of gene products interfering with protein-protein interactions within the cell. Before addition of the cDNA library, a transformed cell expresses the constructs in which the signal molecule comprises a covalently or non-covalently linked primary protein molecule of choice and the reporter molecule is covalently or non-covalently linked to the second protein molecule of choice. The interaction of these proteins results in the release of detectable VLPs. By transfecting the cell with a single or plurality of cDNA molecules capable of expressing a third protein product then this additional protein product when capable of interacting with one of said primary or second protein molecules will affect the release of detectable VLPs. In this way, molecules capable of influencing this interaction between the first and the second protein molecule can be identified. These molecules might only interfere with the binding between first and second protein molecule, or they might constitute even new binding partners for one of said first or second protein molecules. Included in this model are a number of scenarios:

a) The introduced cDNA codes for a protein that interacts with the protein molecule fused to the reporter molecule thus inhibiting the interaction between the signal fusion and the reporter fusion. The result is that VLPs are released that do not carry a reporter molecule. Nevertheless, these VLPs can be distinguished from VLPs carrying the reporter molecule.

b) The introduced cDNA codes for a protein that interacts with the studied protein molecule comprised in a signal molecule thus inhibiting the interaction between the reporter fusion and the signal fusion. The result is that VLPs are released that do not carry a reporter molecule but encapsulate the introduced gene product of said cDNA, whose presence or activity can be assayed for directly in the released population of VLPs. These VLPs can also be distinguished from VLPs carrying the reporter molecule.

c) There is no interaction between the introduced cDNA product and either the signal or the reporter fusion products. Thus the release of VLPs carrying a detectable reporter is not hindered.

Figure 23:
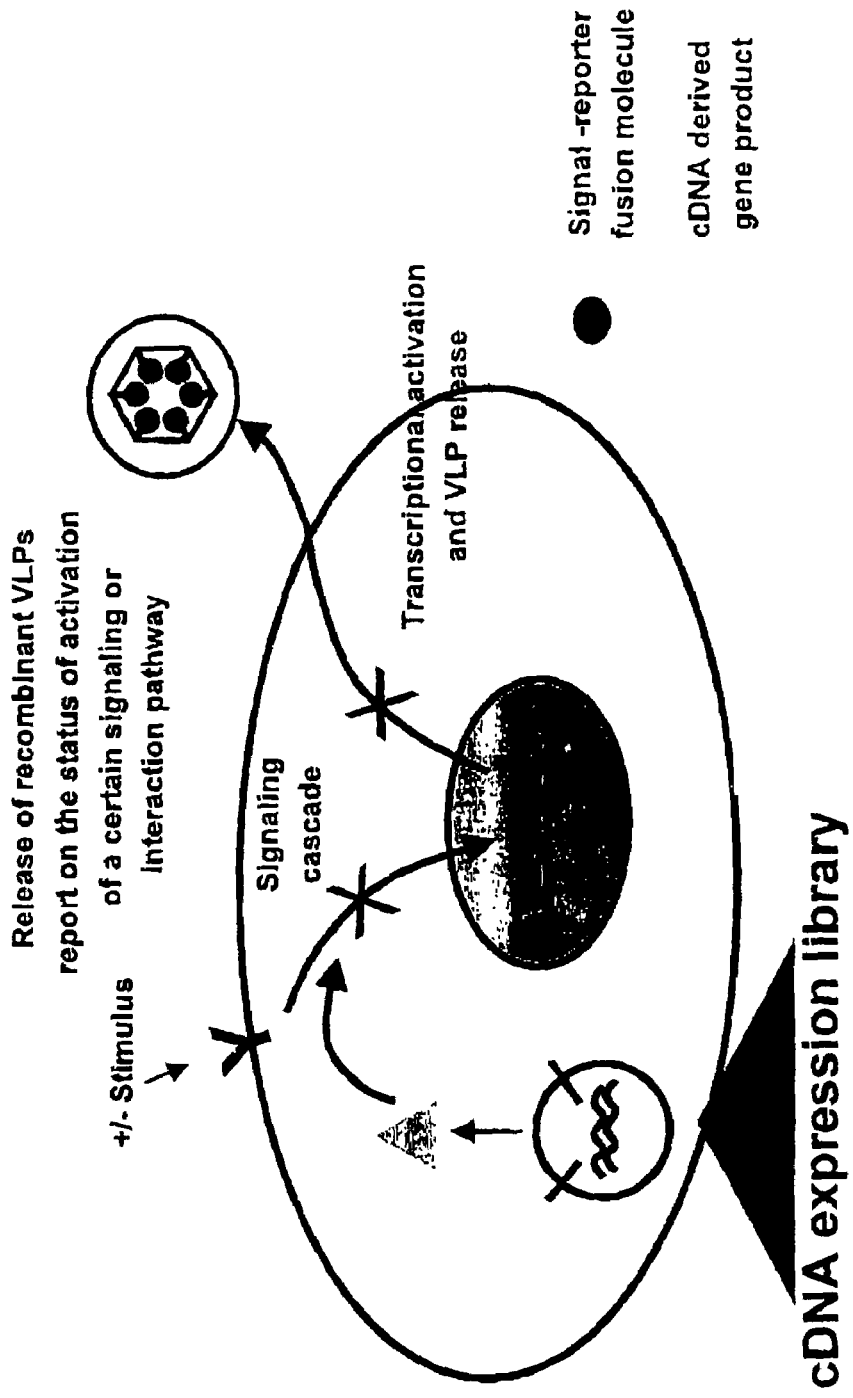

FIG. 23 depicts another preferred embodiment of the present invention. This assay regimen allows the identification of gene products interfering with signal cascades within a cell. A transformed cell line expresses a reporter construct under the control of a specific promoter. When the signal cascade connected to this reporter is stimulated then the release of VLPs can be monitored and quantified. Transfection of such cells with either a single or plurality of cDNA molecules capable of expressing a protein product results in influencing the release of VLPs in a stimulated cell if this additional protein product is capable of modulating said signal transduction pathway. Different read-out scenarios are possible:

1. Interaction of the introduced cDNA product with an element involved in the signal transduction cascade stimulated by an agonist results in the abrogation of production and release of detectable VLPs.

2. Interaction of the introduced cDNA product with an element involved in the signal cascade stimulated by an agonist results in an enhancement of production and release of detectable VLPs.

Figure 24:
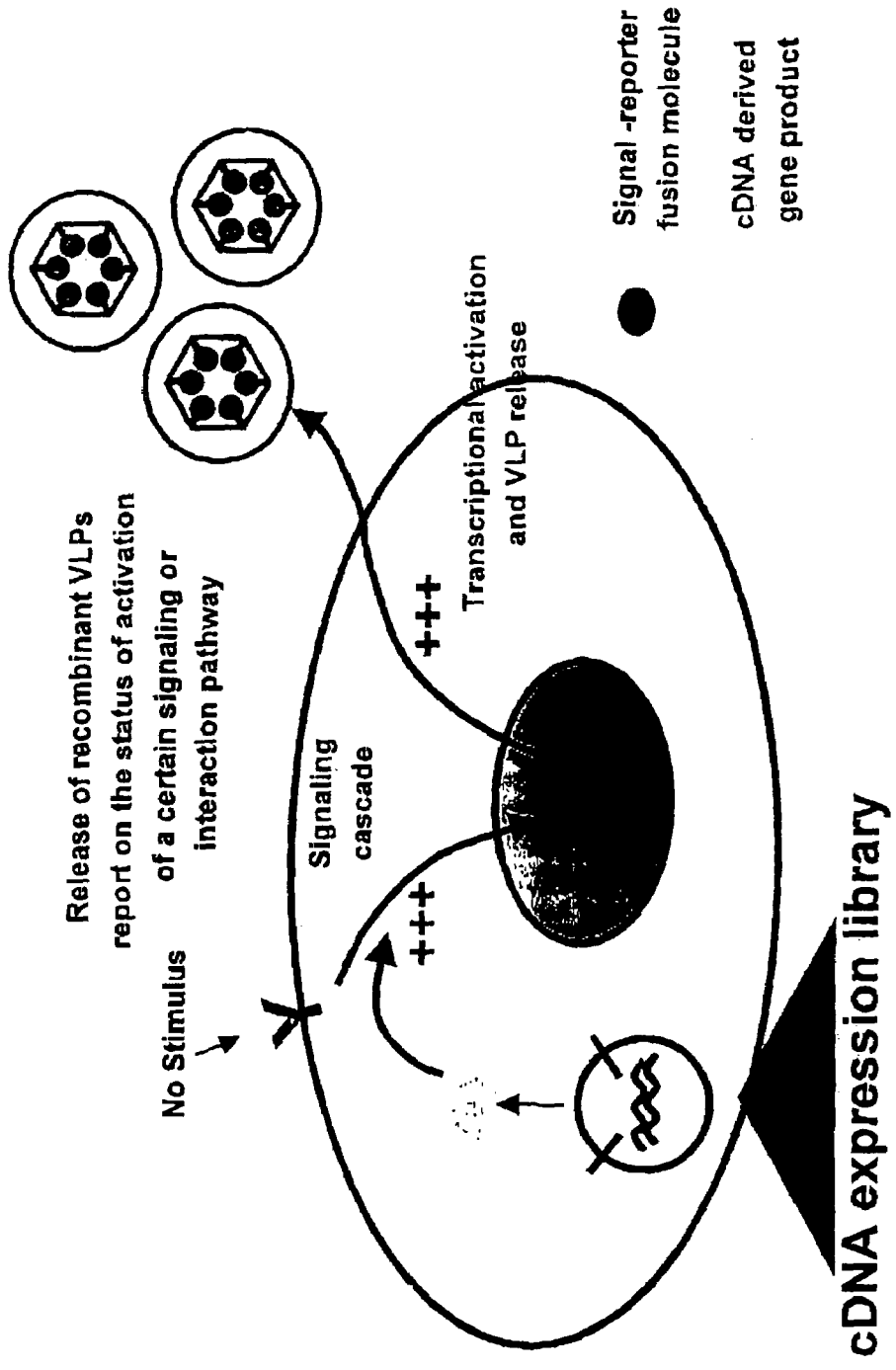

FIG. 24 depicts the interaction of the introduced cDNA product with an element involved in the signal cascade in the absence of an agonist. This interaction results in a stimulation of production and release of VLPs.

FIG. 25 illustrates the principle of complexing of molecules in virus like particeles. The figure depicts a Western blot analysis of the endogenous Gs-α protein derived from the insect host cells and found in VLPs expressing the tagged human Endothelin A receptor and being released from host cells co-expressing the tagged signal and target molecules. In this experiment Sf9 cells were infected for 48 hours with recombinant virus expressing the signal Gag-K-coil protein and/or the target ETAR-E-coil protein. Cells were infected with a constant quantity of virus for the target (ETAR) and the Gag virus (m.o.i. 5 and 2 respectively). The cell culture supernatants were harvested and the VLPs were pelleted at 100 000 g for 30 minutes at 4° C. The resulting pellet was re-suspended in PBS and an aliquot was separated on SDS PAGE and blotted. The resulting blot was probed with an antibody directed against the Insect Gs-α G-protein The results demonstrate the co-segregation of Gs-α and ETAR in the released VLPs.

Lane #1. 5 µl of pelleted ETAR VLPs
Lane #2. 10 µl pelleted ETAR VLPs
Lane #3. 15 µl pelleted ETAR VLPs

MATERIALS AND METHODS

Cell Culture.

Sf9 cells were grown in Grace's insect medium with supplements and 10% insect cell culture certified FBS at 27° C. In a humid atmosphere. Cells were either grown in plastic culture flasks or spinner culture vessels of various sizes (50-500 ml culture volume) with constant stirring. Cells were grown to densities of $1-2\times10^6$ cells/ml before sub-culturing at a starting density of $5\times10^5$ cells/ml. Alternatively the cells were cultivated in serum free Insect Express culture medium as above.

CHO cells were grown in DMEM with glutamine (2 mM) and 10% FCS at 37° C. in a 5% $CO_2$ atmosphere. Cells grown in plastic culture vessels were sub-cultured at 80% confluence. CHO cells were transfected with a construct in which five repeat sequences corresponding to a CRE (cAMP responsive element) originating from the human Somatostatin receptor promoter together with a basal Thymidine kinase (TK) promoter were positioned 5' to a MoMuLV Gag-EGFP fusion gene. Stable cell lines were selected with G418 (400 µg/ml) and individual clones were stimulated with forskolin (as described below) and fluorescent clones (as compared to non-stimulated conditions) were picked for further study. Stimulation of cells with forskolin (2 µM) was performed in CHO formulated serum free medium without phenol red. Cells were analysed by direct fluorescence using a Fluorescence microscope with respective filters to detect fluorescence emitted by stimulated EGFP. For VLP detection the cells were stimulated for varying periods with forskolin and cell culture supernatants were removed and filtered through a 0.45 µM filter before being analysed directly by FIDA (fluorescence intensity distribution analysis as described in EPA 99 112 104,7 and 97 945 816.3, the contents of which are herein incorporated by reference).

Transient Expression in Insect Cells.

Sf9 cells were seeded at $2\times10^6$ in Insect Express serum free medium in a 60 mm dish and the cells were rocked gently from side to side for 2 to 3 minutes to evenly distribute the cells. After this incubation the cells were 50 to 60% confluent. The cells were further incubated for at least 15 minutes without rocking to allow the cells to fully attach to the bottom of the dish to form a monolayer of cells.

To prepare each transfection mixture, a 1.5 ml microcentrifuge tube was used and the reagents were added in the following order.
1 ml Insect Express medium (Biowhittaker Corp.)
plasmid construct (1 µg/µl in TE, pH 8) 10 µl (10 µg)
Insectin-Plus™ Liposomes 20 µl (InVitrogene Corp.)

The mixture was mixed thoroughly and vigorously for 10 seconds and allowed to incubate at room temperature for 15 minutes. After this period the medium was carefully removed from the cells without disrupting the monolayer and the entire transfection mix was added dropwise into the 60 mm dish. The dishes were incubated at room temperature for 4 hours on a side-to-side, rocking platform. Following the 4-hour incubation period, 1-2 ml of Insect Express was added to each 60 mm dish, which were then placed in a sealed plastic bag with moist paper towels to prevent evaporation and incubated at 27° C. Cells were harvested at specific time post transfection Production of Recombinant Baculovirus and High Titre Virus Stocks.

Genes of interest (target and signal molecules) were cloned into the multiple cloning sites of standard Baculovirus transfer vectors and recombinant virus populations were selected also to standard molecular biological procedures. High titre virus stocks were produced by the infection of Sf9 cultures at a cell density of $1\times10^6$ cells/ml at a multiplicity of infection (m.o.i.) of 0.1. Cultures were incubated for 72-96 hours before harvesting of the virus by centrifugation of the cells at 500 g to remove the cell debris. The virus stock was filtered through a 0.45 µM filter and stored at 4° C. in aliquots. Virus titre was determined by plaque titration on Sf9 cells according to standard methods.

Construction of Coiled Coil Tagged Target and Signal Molecules.

To induce the interaction of the target and the signal molecules two peptide sequences capable of forming coiled-coil structures were used which were demonstrated to form specific interactions with each other with high affinity. The peptide sequences in question were:

1) $_{NH2}$-E-V-S-A-L-E-K-$_{COOH}$ E-coil      SEQ ID NO: 1

2) $_{NH2}$-K-V-S-A-L-K-E-$_{COOH}$ K-coil      SEQ ID NO: 2

These heptamers were constructed as pentameric repeat sequences after mammalian back translation and concatamerisation of the respective nucleotide sequences.

```
                                         SEQ ID NO: 3
1) 5'-GAG GTG TCC GCC CTG GAG AAG-3' E-coil SEQ ID NO: 4
2) 5'-AAG GTG TCC GCC CTG AAG GAG-3' K-coil
```

The respective tags were separated from the rest of the molecule via a small glycine linker:

E-coil tag
                                   SEQ ID NO: 5
$_{NH2}$-GGGEVSALEKEVSALEKEVSALEKEVSALEKEVSALEK-$_{COOH}$ K-coil tag
                                   SEQ ID NO: 6
$_{NH2}$-GGGKVSALKEKVSALKEKVSALKEKVSALKEKVSALKE-$_{COOH}$ Oligonucleotides corresponding to the heptameric sequence with a 5' sequence corresponding to the Glycine linker were constructed and the double stranded annealed product was cloned via standard molecular procedures and the sequence was subsequently verified by ds DNA sequencing. Correct sequences were then amplified and ligated onto the respective target and signal molecules at the 3' ends of the molecule.

EXPERIMENTAL PROTOCOLS

Example #1

(Gag-kcoil/EGFP-ecoil)

Western Blot Analysis:

Recombinant Baculovirus containing the carboxyl terminal tagged MoMuLV gag gene (Gag-Kcoil, signal molecule) and a carboxyl terminus tailed EGFP molecule (EGFP-Ecoil, target molecule) were used to infect Sf9 cells as follows. The cells were plated in 35 mm dishes in 2 ml of Grace's insect medium with supplements and 10% insect cell culture certified FBS at 27° C. in a humid atmosphere at a density of $5 \times 10^5$ cells/ml. After the cells had adhered (one hour at room temperature) the medium was removed and both viruses were added at the corresponding m.o.i. in a total volume of 1 ml. Cells were incubated for 48 hour at 27° C. in a humid atmosphere, Cells were harvested in that the cell culture supernatant was carefully removed and centrifuged at 1000 g for 5 minutes at 4° C. to remove cells and debris. The supernatant was decanted and filtered through a 0.45 µM filter. VLPs were concentrated by centrifugation of the filtered cell culture supernatant at 100 000 g for 30 minutes at 4° C. Pelleted VLPs were re-suspended in PBS and stored at 4° C. The infected cells were washed once with PBS before being lysed in 50 mM Tris-HCl, 150 mM NaCl, 1% NP40, pH7.8 and protease inhibitors on ice for 20 minutes. The lysed cells were then centrifuged for 10 minutes at 10 000 g and the soluble protein fraction was then used for SDS PAGE analysis. Aliquots of either VLPs or the soluble protein lysates were re-suspended in 2×SDS PAGE sample buffer (20 mM Tris-HcCl pH 6.8.2% SDS, 20 mM DTT, 2% BME, 10% glycerol) and boiled for 1 minute to denature the samples. Protein samples were then separated on 12% SDS PAGE gels according to standard molecular biological methods. The separated proteins were then transferred to PVDF membranes using a semi-dry blotting apparatus at 150 mA for one hour in (48 mM Tris, 39 mM Glycin, 20% Methanol, 0.037% SDS). Blots were then processed as follows. The membranes were incubated for 1 hour in a blocking solution (TBST; 20 mM TRIS-HCl, pH 7.6, 137 mM NaCl, 0.05% TWEEN 20, containing 0.1% Casein-Hydrolysate). Following this incubation the filters were washed for 5 minutes in TBST before addition of 10 ml of blocking solution containing the primary antibody either directed against the signal molecule (rabbit anti-Gag, 1:10 000 final dilution) or the target molecule (rabbit anti-GFP, 1:5000 final dilution). The filters were incubated in this solution for one hour at room temperature with constant agitation before being washed three times for 5 minutes with TBST. Then 10 ml of blocking solution containing the peroxidase conjugated secondary antibody (goat anti-rabbit antibody conjugated with horse radish peroxidase, 1:2500) was incubated with the membrane for one hour at room temperature with constant agitation before being washed three times for 5 minutes with TBST. The filters were then rinsed briefly with distilled water and developed by addition of ECL detection reagents 1 and 2 and 3% BSA (end concentration) for 60 seconds. The filters were removed from the detection solution and dried between two paper towels before being exposed to ECL detection films. The strength of the signal was dependent upon the exposure time.

FIDA Analysis

Quantitative Analysis of Fluorescent VLPs by FIDA

The supernatant of Sf9 cells co-expressing Gag-Kcoil and EGFP-Ecoil was filtered (0.45 µm) and directly used for FIDA analysis (a) or centrifuged (100000 g, 4° C., 30 min) in order to harvest the VLPs (b). The supernatant was removed and the pellet resuspended in PBS. Prior to FIDA analysis the samples were homogenised briefly by sonication in the presence of 0.01% (v/v) Tween-20 and diluted with sterile cell culture medium (a) or PBS (b), containing 0.01% (v/v) Tween-20, respectively. The VLPs were analysed by FIDA using a beam scanner as disclosed in PCT/EP97/03022 (the contents of which are herein incorporated by reference) and 488 nm laser light for excitation.

Example #2

(Gag-ecoil/EGFR-kcoil)

Western Blot Analysis

Recombinant Baculovirus containing the carboxyl terminal tagged MoMuLV gag gene (Gag-Ecoil, signal molecule) and a carboxyl terminus tailed EGFR molecule (EGFR-Kcoil, target molecule) were used to infect Sf9 cells as follows. The cells were plated in 35 mm dishes In 2 ml of Grace's insect medium with supplements and 10% insect cell culture certified FBS at 27° C. in a humid atmosphere at a density of $5 \times 10^5$ cells/ml. After the cells had adhered (one hour at room temperature) the medium was removed and both viruses were added at the corresponding m.o.i. in a total volume of 1 ml. Cells were Incubated for 48 hour at 27° C. in a humid atmosphere. Cells were harvested in that the cell culture supernatant was carefully removed and centrifuged at 1000 g for 5 minutes at 4° C. to remove cells and debris. The supernatant was decanted and filtered through a 0.45 µM filter. VLPs were concentrated by centrifugation of the filtered cell culture supernatant at 100 000 g for 30 minutes at 4° C. Pelleted VLPs were re-suspended in PBS and stored at 4° C. The infected cells were washed once with PBS before being lysed in 50 mM Tris-HCl, 150 mM NaCl, 1% NP40, pH7.8 and protease inhibitors on ice for 20 minutes. The lysed cells were then centrifuged for 10 minutes at 10 000 g and the soluble protein fraction was then used for SDS PAGE analysis. Aliquots of either VLPs or the soluble protein lysates were re-suspended in 2×SDS PAGE sample buffer (20 mM Tris-HcCl pH 6.8.2% SDS, 20mM DTT, 2% βME, 10% glycerol) and boiled for 1 minute to denature the samples. Protein samples were then separated on 12% SDS PAGE gels according to standard molecular biological methods. The separated proteins were then transferred to PVDF membranes using a semi-dry blotting apparatus at 150 mA for one hour in (48 mM Tris, 39 mM Glycin, 20% Methanol, 0.037% SDS). Blots were then processed as follows. The membranes were incubated for 1 hour in a blocking solution (TBST; 20 mM TRIS-HCl, pH 7.6, 137 mM NaCl, 0.05% TWEEN 20, containing 0.1% Casein-Hydrolysate). Following this incubation the filters were washed for 5 minutes in TBST before addition of 10 ml of blocking solution containing the primary antibody either directed against the signal molecule (rabbit anti-Gag, 1:10 000 final dilution) or the target molecule (rabbit anti-EGFR, 1:1000 final dilution), The filters were incubated in this solution for one hour at room temperature with constant agitation before being washed three times for 5 minutes with TBST. Then 10 ml of blocking solution containing the peroxidase conjugated secondary antibody (goat anti-rabbit antibody conjugated with horse radish peroxidase, 1:2500) was incubated with the membrane for one hour at room temperature with constant agitation before being washed three times for 5 minutes With TBST. The filters were then rinsed briefly with distilled water and developed by addition of ECL detection reagents 1 and 2 and 3% BSA (end concentration) for 60 seconds. The filters were removed from the detection solution and dried between two paper towels before being exposed to ECL detection films. The strength of the signal was dependent upon the exposure time.

FIDA Analysis

EGF Receptor Binding Assay and FIDA Analysis:

5 nM TAMRA-labelled EGF was incubated with membrane vesicles prepared from A431 cells or with VLPs derived from Sf9 cells co-expressing Gag-E-coil and the EGF receptor tagged with K-coil in assay buffer [20 mM HEPES, 140 mM NaCl, 5 mM KCl, 1.2 mM $MgCl_2$, 1.8 mM $CaCl_2$, 0.35 g/l $NaHCO_3$, 1 g/l glucose, 0.01% (w/v) Pluronic F-127, pH 7.4] in the presence or absence of 1 µM non-labelled EGF. After 30 minutes incubation at room temperature the mixture was analysed by FIDA using a beam scanner and 543 nm laser light for excitation.

Example #3

(Gag-Kcoil/$ET_A$ Receptor-ecoil)

Western Blot Analysis

Recombinant Baculovirus containing the carboxyl terminal tagged MoMuLV gag gene (Gag-Kcoil, signal molecule) and a carboxyl terminus tailed $ET_A$ receptor molecule ($ET_A$ receptor-Ecoil, target molecule) were used to infect Sf9 cells as followed. The cells were plated in 35 mm dishes in 2 ml of Grace's insect medium with supplements and 10% insect cell culture certified FBS at 27° C. in a humid atmosphere at a density of $5\times10^5$ cells/ml. After the cells had adhered (one hour at room temperature) the medium was removed and both viruses were added at the corresponding m.o.i. in a total volume of 1 ml. Cells were incubated for 48 hour at 27° C. in a humid atmosphere. Cells were harvested in that the cell culture supernatant was carefully removed and centrifuged at 1000 g for 5 minutes at 4° C. to remove cells and debris. The supernatant was decanted and filtered through a 0.45 µM filter. VLPs were concentrated by centrifugation of the filtered cell culture supernatant at 100 000 g for 30 minutes at 4° C. Pelleted VLPs were re-suspended in PBS and stored at 4° C. The infected cells were washed once with PBS before being lysed in 50 mM Tris-HCl, 150 mM NaCl, 1% NP40, pH7.8 and protease Inhibitors on ice for 20 minutes. The lysed cells were then centrifuged for 10 minutes at 10 000 g and the soluble protein fraction was then used for SDS PAGE analysis. Aliquots of either VLPs or the soluble protein lysates were re-suspended in 2×SDS PAGE sample buffer (20 mM Tris-HcCl pH 6.8.2% SDS, 20 mM DTT, 2% βME, 10% glycerol) and boiled for 1 minute to denature the samples. Protein samples were then separated on 12% SDS PAGE gels according to standard molecular biological methods. The separated proteins were then transferred to PVDF membranes using a semi-dry blotting apparatus at 150 mA for one hour in (48 mM Tris, 39 mM Glycin, 20% Methanol, 0.037% SDS). Blots were then processed as follows. The membranes were incubated for 1 hour in a blocking solution (TBST; 20 mM TRIS-HCl, pH 7.6, 137 mM NaCl, 0.05% TWEEN 20, containing 0.1% Casein-Hydrolysate). Following this Incubation the filters were washed for 5 minutes in TBST before addition of 10 ml of blocking solution containing the primary antibody either directed against the signal molecule (rabbit anti-Gag, 1:10 000 final dilution) or the target molecule (rabbit anti-$ET_A$ receptor, 1:1000 final dilution). The filters were incubated in this solution for one hour at room temperature with constant agitation before being washed three times for 5 minutes with TBST. Then 10 ml of blocking solution containing the peroxidase conjugated secondary antibody (goat anti-rabbit antibody conjugated with horse radish peroxidase, 1:2500) was incubated with the membrane for one hour at room temperature with constant agitation before being washed three times for 5 minutes with TBST. The filters were then rinsed briefly with distilled water and developed by addition of ECL detection reagents 1 and 2 and 3% BSA (end concentration) for 60 seconds. The filters were removed from the detection solution and dried between two paper towels before being exposed to ECL detection films. The strength of the signal was dependent upon the exposure time.

FIDA Analysis $ET_A$ Receptor Binding Assay and FIDA Analysis:

2 nM TAMRA-labeled endothelin-1 was incubated with membrane vesicles prepared from recombinant CHO cells expressing the $ET_A$ receptor or with VLPs derived from Sf9 cells co-expressing Gag-K-coil and the $ET_A$ receptor tagged with Flag and E-coil in assay buffer [50 mM Tris-HCl, pH 7.4, 1 mM $CaCl_2$, 0.1% (w/v) BSA, 0.05% (v/v) Tween-20] in the presence or absence of 1 µM non-labelled endothelin-1 (competing ligand) or big endothelin-1 (non-competing ligand) or somatostatin-14 (non-competing ligand). After 30 minutes incubation at room temperature the mixture was analysed by FIDA using a beam scanner and 543 nm laser light for excitation.

Example #4

Gag-EGFP Reporter System

Fluorescence Microscopy Analysis

CHO cells stably transfected with a construct carrying the MoMuLV Gag-EGFP fusion gene downstream of a promoter constituting of a basal TK promoter and five consecutive CREs originating from the human somatostatin receptor were grown in DMEM with glutamine (2 mM) and 10% FCS and 400 µg/ml G418 at 37° C. In a 5% $CO_2$ atmosphere. Stimulation of cells with foskolin (2 µM) was performed in CHO formulated serum free medium without phenol red. Cells were analysed by direct fluorescence using a Fluorescence microscope with respective filters to detect fluorescence emitted by stimulated EGFP. For VLP detection the cells were stimulated for varying periods with forskolin and cell culture supernatants were removed and filtered through a 0.45 µM filter before being analysed directly by FIDA.

Quantitative Analysis of Fluorescent VLPs by FIDA

The supernatant of CHO cells expressing Gag-EGFP fusion gene was filtered (0.45 µm) and directly used for FIDA analysis. Prior to FIDA analysis the samples were homogenised briefly by sonication in the presence of 0.01% (v/v) Tween-20. The VLPs were analysed by FIDA using a beam scanner and 488 nm laser light for excitation.

Example #5

Protein-protein Interactions Interaction of Ras and Raf Fusion Proteins

Sf9 cells grown in Insect Express serum free medium were transiently transfected (using a liposome based transfection reagent, InVitrogen) with constructs expressing either the Gag-human Ras fusion, a full length human Raf or a Raf-EGFP fusion. After 96 hours the cells were harvested in that the cell culture supernatant was carefully removed and centrifuged at 10 000 g for 5 minutes at 4° C. to remove cells and debris. The supernatant was decanted and filtered through a 0.4 µM filter. VLPs were concentrated by centrifugation of the filtered cell culture supernatant at 100 000 g for 30 minutes at 4° C. Pelleted VLPs were re-suspended in PBS and stored at 4° C. The transfected cells were washed once with PBS before being lysed in 50 mM Tris-HCl, 150 mM NaCl, 1% NP40, pH7.8 and protease inhibitors on ice for 20 minutes. The lysed cells were then centrifuged for 10 minutes at 10 000 g and the soluble protein fraction was then used for SDS PAGE analysis. Aliquots of either VLPs or the soluble protein lysates were re-suspended in 2×SDS PAGE sample buffer (20 mM Tris-HcCl pH 6,8.2% SDS, 20 mM DTT, 2% βME, 10% glycerol) and boiled for 1 minute to denature the samples. Protein samples were then separated on 12% SDS PAGE gels according to standard molecular biological methods. The separated proteins were then transferred to PVDF membranes using a semi-dry blotting apparatus at 150 mA for one hour in (48 mM Tris, 39 mM Glycin, 20% Methanol, 0.037% SDS). Blots were then processed as follows. The membranes were incubated for 1 hour in a blocking solution (TBST; 20 mM TRIS-HCl, pH 7.6, 137 mM NaCl, 0.05% TWEEN 20, containing 0.1% Casein-Hydrolysate). Following this incubation the filters were washed for 5 minutes in TBST before addition of 10 ml of blocking solution containing the primary antibody either directed against the Gag-Ras fusion molecule (rabbit anti-Ras, 1:1000 final dilution), the full length Raf molecule (rabbit anti-Raf, 1:1000 final dilution) or the Raf-EGFP fusion molecule (rabbit anti-GFP, 1:1000). The filters were incubated in this solution for one hour at room temperature with constant agitation before being washed three times for 5 minutes with TBST. Then 10 ml of blocking solution containing the peroxidase conjugated secondary antibody (goat anti-rabbit antibody conjugated with horse radish peroxidase, 1:2500) was incubated with the membrane for one hour at room temperature with constant agitation before being washed three times for 5 minutes with TBST. The filters were then rinsed briefly with distilled water and developed by addition of ECL detection reagents 1 and 2 and 3% BSA (end concentration) for 60 seconds. The filters were removed from the detection solution and dried between two paper towels before being exposed to ECL detection films. The strength of the signal was dependent upon the exposure time.

The invention claimed is:

1. A method to selectively incorporate or encapsulate a proteinaceous target molecule complex, comprising a target molecule and one or more complexing components, into a virus like particle comprising the steps of:
   expressing in cells
      a) a target molecule, said target molecule comprising a coiled-coil sequence fused to a G-protein coupled receptor, and
      b) a complexing component comprising a G-protein, and
      c) a signal molecule comprising a coiled-coil sequence fused to a retroviral capsid sequence, wherein said retroviral capsid sequence confers on the signal molecule the ability to assemble into virus like particles,
   incorporating or encapsulating a target molecule complex into virus like particles through the interaction of said coiled-coil sequence of said target molecule with said coiled-coil sequence of said signal molecule, wherein said coiled-coil interaction is between a K-coil and an E-coil, and wherein said target molecule complex is an association between said target molecule and said complexing component.

2. A method according to claim 1 wherein the association of said target molecule and said complexing component effects formation of hetero-dimers or hetero-oligomers.

3. A method according to claim 1 wherein the association of said target molecule and said complexing component is between a G-protein coupled receptor and a G protein.

4. A method according to claim 3 wherein said G-protein coupled receptor is a human endothelin A receptor.

5. The method according to claim 3 wherein said G-protein coupled receptor is a human epidermal growth factor receptor.

6. The method according to claim 1 wherein said G-protein is the alpha G-protein subunit (Gs-a protein).

7. The method according to claim 1 comprising endogenous expression of said G-protein.

8. The method according to claim 1 comprising encoding said retroviral capsid sequence of said signal molecule by a retroviral gag-gene.

9. The method according to claim 8 comprising encoding a gag poly-protein precursor Gag Pr65 by said retroviral gag-gene.

10. The method according to claim 1 wherein said coiled-coil interaction comprises physical forces selected from the group consisting of electrostatic forces, van der Waals forces, stacking interactions, hydrogen bonding and steric fit.

11. The method according to claim 1 further comprising releasing the virus like particles from said cells into an extracellular environment.

12. The method according to claim 11 comprising releasing the virus like particles from said cells into an extracellular environment by a mechanism of budding through a cellular membrane.

13. A virus like particle obtainable by the method according to claim 1.

* * * * *

SEQUENCE LISTING

```
<160> NUMBER OF SEQ ID NOS: 6

<210> SEQ ID NO 1
<211> LENGTH: 7
<212> TYPE: PRT
<213> ORGANISM: Artificial
<220> FEATURE:
<223> OTHER INFORMATION: coiled-coil forming sequence

<400> SEQUENCE: 1

Glu Val Ser Ala Leu Glu Lys
1               5

<210> SEQ ID NO 2
<211> LENGTH: 7
<212> TYPE: PRT
<213> ORGANISM: Artificial
<220> FEATURE:
<223> OTHER INFORMATION: coiled-coil forming sequence

<400> SEQUENCE: 2

Glu Val Ser Ala Leu Lys Glu
1               5

<210> SEQ ID NO 3
<211> LENGTH: 21
<212> TYPE: DNA
<213> ORGANISM: Artificial
<220> FEATURE:
<223> OTHER INFORMATION: coiled-coil peptide encoding sequence

<400> SEQUENCE: 3
gaggtgtccg ccctggagaa g                                              21

<210> SEQ ID NO 4
<211> LENGTH: 21
<212> TYPE: DNA
<213> ORGANISM: Artificial
<220> FEATURE:
<223> OTHER INFORMATION: coiled-coil peptide encoding sequence

<400> SEQUENCE: 4
aaggtgtccg ccctgaagga g                                              21
```

```
<210> SEQ ID NO 5
<211> LENGTH: 38
<212> TYPE: PRT
<213> ORGANISM: Artificial
<220> FEATURE:
<223> OTHER INFORMATION: E-coil tag

<400> SEQUENCE: 5

Gly Gly Gly Glu Val Ser Ala Leu Glu Lys Glu Val Ser Ala Leu Glu
1               5                   10                  15

Lys Glu Val Ser Ala Leu Glu Lys Glu Val Ser Ala Leu Glu Lys Glu
            20                  25                  30

Val Ser Ala Leu Glu Lys
        35

<210> SEQ ID NO 6
<211> LENGTH: 38
<212> TYPE: PRT
<213> ORGANISM: Artificial
<220> FEATURE:
<223> OTHER INFORMATION: K-coil tag

<400> SEQUENCE: 6

Gly Gly Gly Glu Val Ser Ala Leu Lys Glu Val Ser Ala Leu Lys
1               5                   10                  15

Glu Glu Val Ser Ala Leu Lys Glu Val Ser Ala Leu Lys Glu Glu
            20                  25                  30

Val Ser Ala Leu Lys Glu
        35
```